(12) United States Patent
Auras et al.

(10) Patent No.: US 10,259,768 B2
(45) Date of Patent: Apr. 16, 2019

(54) METHOD OF RECYCLING A POLYESTER

(71) Applicant: Board of Trustees of Michigan State University, East Lansing, MI (US)

(72) Inventors: Rafael Auras, Okemos, MI (US); Fabiola Maria Iñiguez-Franco, East Lansing, MI (US); Maria Rubino, East Lansing, MI (US); Daniel Holmes, DeWitt, MI (US); Susan E. Selke, East Lansing, MI (US); Xiaoyi Fang, Hudson, OH (US)

(73) Assignee: BOARD OF TRUSTEES OF MICHIGAN STATE UNIVERSITY, Ease Lansing, MI (US)

( * ) Notice: Subject to any disclaimer, the term of this patent is extended or adjusted under 35 U.S.C. 154(b) by 0 days.

(21) Appl. No.: 15/986,930

(22) Filed: May 23, 2018

(65) Prior Publication Data

US 2018/0339957 A1    Nov. 29, 2018

Related U.S. Application Data

(60) Provisional application No. 62/510,563, filed on May 24, 2017.

(51) Int. Cl.
*C07C 51/09* (2006.01)
*C08J 5/18* (2006.01)

(52) U.S. Cl.
CPC ............... *C07C 51/09* (2013.01); *C08J 5/18* (2013.01); *C08J 2367/04* (2013.01)

(58) Field of Classification Search
CPC .............................. C07C 51/09; C08J 2367/04
See application file for complete search history.

(56) References Cited

U.S. PATENT DOCUMENTS

| | | | |
|---|---|---|---|
| 6,984,694 B2 | 1/2006 | Blasius, Jr. et al. | |
| 8,431,683 B2 * | 4/2013 | Coszach | C07C 51/09 528/480 |
| 8,481,675 B2 | 7/2013 | Coszach et al. | |
| 8,614,338 B2 | 12/2013 | Coszach et al. | |

FOREIGN PATENT DOCUMENTS

WO        2015112098 A1    7/2015

OTHER PUBLICATIONS

Iniguez-Franco et al (Polymer, Concurrent solvent induced crystallization and hydrolytic degradation of PLA by water-ethanol solutions, 2016, 99, pp. 315-323, includes supplementary info pp. 1-30). (Year: 2016).*
Gironi et al, Journal of Polymers and the Environment, PLA Chemical Recycling Process Optimization: PLA Solubilization in Organic Solvents, 2016, 24, pp. 328-333. (Year: 2016).*
Hoogsteen, W. et al., "Crystal Structure, Conformation, and Morphology of Solution-Spun Poly(L-lactide) Fibers", Macromolecules, vol. 23, 1990, pp. 634-642.
ICIS, "Indicative Chemical Prices A-Z", Sep. 2017, http://www.icis.com/chemicals/channel-info-chemicals-a-z/, 6 pages.
Ikada, Yoshito et al., "Biodegradable Polyesters for Medical and Ecological Applications", Macromol. Rapid Commun., vol. 21, 2000, pp. 117-132.
Iniquez-Franco, Fabiola et al., "Concurrent Solvent Induced Crystallization and Hydrolytic Degradatioin of PLA by Water-Ethanol Solutions", Polymer, 2016, pp. 1-9.
Iniguez-Franco, Fabiola et al., "Effect of Nanoparticles on the Release of Lactic Acid and From Poly(lactic acid) Bionanocomposites", Gorden Research Conference, Waltham, MA, USA, Jun. 2015, 1 page.
Iniguez, Franco, Fabiola et al., "Effect of Food Stimulants in the Hydrolytic Degradation of Poly(lactic acid) Films", 3rd International Meeting on Material/Bioproduct Interaction, Zaragoza, Spain, Jun. 2015, pp. 1-22.
Iniguez-Franco, Fabiola et al., "Effect of Nanoparticles on the Release of Lactic Acid and Surfactant from Poly (lactic acid)-Bionanocomposites", 2nd International Conference on Food and Beverage Packaging, Rome, Italy, Jun. 2016, pp. 1.22.
Iniguez-Franco, Fabioloa et al., "Effect of Nanoparticles on the Hydrolytic Degradation of PLA-Nanocomposites by Water-Ethanol Solutions", Polymer Degradation and Stability, vol. 146, 2017, pp. 287-297.
Jamshidian, Majid et al., "Poly-Lactic Acid: Production, Applications, Nanocomposites and Release Studies", Comprehensive Reviews in Food Science and Food Safety vol. 9, 2010, pp. 552-571.
Jamshidi, K. et al., "Thermal Characterization of Polylactides", Polymer, vol. 29, Dec. 1988, pp. 2229-2234.
Japon, Sonia et al., "Molecular Characterization and Rheological Properties of Modified Poly(Ethylene Terephthalate) Obtained by Reactive Extrusion", Polymer Engineering and Science, vol. 41, No. 8, Aug. 2001, pp. 1299-1309.
Japon, S., "Reactive Processing of Poly(ethylene terephthalate) Modified with Multifunctional Epoxy-Based Additives", Polymer, vol. 41, 2000, pp. 5809-5818.
Ju, Shiaw T. et al., "Influence of Temperature on the Diffusion of Solvents in Polymers Above the Glass Transition Temperature", Ind. Eng. Chem. Prod. Dev., vol. 20, 1981, pp. 330-335.
Jung, Jae Hwan et al., "Acid- and Base-Catalyzed Hydrolyses of Aliphatic Polycarbonates and Polyesters", Catalysis Today, vol. 115, 2006, pp. 283-287.
Kale Gaurav et al., "Biodegradability of Polylactide Bottles in Real and Simulated Composting Conditions", Polymer Testing, vol. 26, 2007, pp. 1049-1061.
Kale, Gaurav et al., "Degradation of Commercial Biodegradable Packages Under Real Composting and Ambient Exposure Conditions", J. Polym. Environ., vol. 14, 2006, pp. 317-334.

(Continued)

*Primary Examiner* — Paul A Zucker
(74) *Attorney, Agent, or Firm* — Howard & Howard Attorneys PLLC

(57) ABSTRACT

A method of recycling a polyester includes the steps of providing the polyester, preparing a solution containing water and an alcohol, submerging the polyester in the solution, and hydrolytically depolymerizing the polyester while the polyester is submerged in the solution.

18 Claims, 35 Drawing Sheets

(56) References Cited

OTHER PUBLICATIONS

Kalkar, A.K. et al., "Isothermal Crystallization Kinetics of Poly(phenylene sulfide)/TLCP Composites", Polymer Engineering and Science, 2009, pp. 397-417.

Kawai, Takahiko et al., "Crystallization and Melting Behavior of Poly (L-lactic acid)", Macromolecules, vol. 40, pp. 9463-9469.

Ke, Tianyi et al., "Melting Behavior and Crystallization Kinetics of Starch and Poly(lactic acid) Composites", Journal of Applied Polymer Science, vol. 89, 2003, pp. 1203-1210.

Kijchavengkul, Thitisilp et al., "Atmospheric and Soil Degradation of Aliphatic—Aromatic Polyester Films", Polymer Degradation and Stability, vol. 95, 2010, pp. 99-107.

Lai, M.-K. et al., "Microencapsulation of Acetaminophen into Poly(L-lactide) by Three Defferent Emulsion Solvent-Evaporation Methods", Journal of Microencapsulation, vol. 22, No. 3, May 2005, pp. 261-274.

Lee, Sanboh, "Fourteen-Year-Old Aging Study of the Effect of Thickness on Methanol Transport in Crosslinked Poly (methyl Methacrylate)", J. Mater. Res., vol. 11, No. 10, Oct. 1996, pp. 2403-2405.

Lee, Wen-Hao et al., "Kinetics of Solvent-Induced Crystallization of Polyy(ethylene terephthalate) at the Final Stage", Journal of Polymer Research, vol. 10, 2003, pp. 133-137.

Lyu, SuPing et al., "Kinetics and Time-Temperature Equivalence of Polymer Degradation", Biomacromolecules, vol. 8, 2007, pp. 2301-2310.

Makino, Kimiko et al., "Mechanism of Hydrolytic Degradation of Poly(L-lactide) Microcapsules: Effects of pH, Ionic Strength and Buffer Concentration", Microencapsulation, vol. 3, No. 3, 1986, pp. 213-218.

Marubayashi, Hironori et al., "Complex Crystal Formation of Poly(L-lactide) with Solvent Molecules", Macromolecules, vol. 45, 2012, pp. 1364-1397.

Meng, Qingkai et al., "Control of Thermal Degradation of Polylactide/Clay Nanocomposites During Melt Processing by Chain Extension Reaction", Polymer Degradation and Stability, vol. 97, 2012, pp. 2010-2020.

Meng, Q.-K. et al., "Effects of a Multifunctional Polymeric Chain Extender on the Propeties of Polylactide and olylactide/Clay Nanocomposites", Intern. Polymer Processing, vol. XXVII, No. 5, 2012, pp. 505-516.

Mihai, Mihaela et al., "Rheology and Extrusion Foaming of Chain-Branched Poly(lactic acid)", Polymer Engineering and Science, 2010, pp. 629-642.

Mitchell, Mary K., "Degradation of PLA Fibers at Elevated Temperature and Humidity", Polymer Engineering and Science, 2014, pp. 1-9.

Mohd-Adnan, Ahmad-Faris et al., "Evaluation of Kinetics Parameters for Poly(L-lactic acid) Hydrolysis Under High-Pressure Steam", Polymer Degradation and Stability, vol. 93, 2008, pp. 1053-1058.

Muñoz, Ivan et al., "Life Cycle Assessment of Bio-Based Ethanol Produced From Different Agricultural Feedstocks", Int. J. Life Cycle Assess., vol. 19, 2014, pp. 109-119.

Mutsuga, M. et al., "Migration of Lactic Acid, Lactide and Oligomers from Polylactide Food-Contact Materials", Food Additives & Contaminants: Part A, vol. 25, No. 10, Oct. 2008, pp. 1283-1290.

Najafi, N. et al., "Control of Thermal Degradation of Polylactide (PLA)-Clay Nanocomposites Usign Chain Extenders", Polymer Degradation and Stability, vol. 97, 2012, pp. 554-565.

Nampoothiri, K. Madhaven et al., "An Overview of the Recent Developments in Polylactide (PLA) Research", Bioresource Technology, vol. 101, 2010, pp. 8493-8501.

Nofar, Mohammadreza et al., "Crystallatin Kinetics of Linear and Long-Chain-Branched Polylactide", Ind. Eng. Chem. Res., vol. 50, 2011, pp. 13789-13798.

Ojijo, Vincent et al., "Super Toughened Biodegradable Polylactide Blends with Non-Linear Copolymer Interfacial Architecture Obtained via Facile In-Situ Reactive Compatibilization", Polymer, vol. 80, 2015, pp. 1-17.

Okamoto, Kohei et al., "Degradation of Poly(lactic acid) Into Repolymerizable Oligomer Using Montmorillonite K10 for Chemical Recycling", Macromol. Biosci., vol. 5, 2005, pp. 813-820.

Ouyang, Hao et al.., "Solvent-Induced Crystallation in Poly(ethylene terephthalate) During Mass Transport: Mechanism and Boundary Condition", Macromolecules, vol. 37, 2004, pp. 7719-7723.

Ouyang, Hao et al., "Three Stages of Crystallation in Poly(ethylene terephthalate) During Mass Transport", Macromolecules, vol. 35, 2002, pp. 8248-8432.

Pan, Zhen et al., "Poly(lactide-co-glycolide) Porous Scaffolds for Tissue Engineering and Regenerative Medicine", Interface Focus, vol. 2, 2012, pp. 366-377.

Papageorgiou, G.Z. et al., "PLA Nanocomposites: Effect of Filler Type on Non-Isothermal Crystallization", Thermochimica Acta, vol. 511, 2010, pp. 129-139.

Park, Ju-Young et al., "Controlled Release of Ketoprofen from Electrospun Porous Polylactic Acid (PLA) Nanofibers", J. Polym. Res., vol., 18, 2011, pp. 1287-1291.

Perejón, Antonio et al, "Kinetic Analysis of Complex Solid-State Reactions, A New Deconvolution Procedure", J. Phys. Chem. B., vol. 115, 2011, pp. 1780-1791.

Piemonte, V. et al., "Chemical Recycling of PLA: A Great Opportunity Towards the Sustainable Development?", J. Polym. Environ., vol. 21, 2013, pp. 640-647.

Piemonte, V. et al., "Kinetics of Hydrolytic Degradation of PLA", J. Polym. Environ., vol. 21, 2013, pp. 313-318.

Pitt, Colin G. et al., "Modification of the Rates of Chain Cleavage of Poly(e-Caprolactone) and Related Polyesters in the Solid State", Journal of Controlled Release, vol. 4, 1987, pp. 283-292.

Pritchard, D.J. et al., "Statistical Assessment of Chemical Kinetic Models", Chemical Engineering Science, vol. 30, 1975, pp. 567-574.

Ray, Suprakas Sinha et al., "New Polylactide/Layered Silicate Nanocomposites. 1. Preparation, Characterization, and Properties", Macromolecules, vol. 35, 2002, pp. 3104-3110.

Samsudin, Hayati et al., "Migration of Antioxidants from Polylactic Acid Films: A Parameter Estimation Approach and an Overview of the Current Mass Transfer Models", Food Research International, vol. 103, 2018, pp. 515-528.

Agarwal, Anil K. et al,, "Sequential Experiemental Design for Precise Parameter Estimation. 1. Use of Reparameterization", Ind. Eng. Chem. Process Des. Dev., vol. 24, 1985, pp. 203-207.

Agarwal, Anil K. et al., "Sequential Experimental Design for Precise Paramter Estimation. 2. Design Criteria", Ind. Eng. Chem. Process Des. Dev., vol. 24, 1985, pp. 207-210.

Aharoni, Shaul M. et al., "Effects of Solvent-Induced Crystallation on the Amorphous Phase of Polycarbonate of Bisphenol A)", International Journal of Polymeric Materials and Polymeric Biomaterials, vol. 42, 1998, Pates 275-283.

Ahmed, Maqsood et al., "Effects of Sterilization Treatments on Bulk and Surface Properties of Nanocomposite Biomaterials", Journal of Biomiedical Materials Reserach Part B: Applied Biomaterials, Wiley Periodicals, Inc., 2013, pp. 1182-1190.

Ahmad-Farts, Mohd-Adnan et al., "Evaluation of Kinetics Parameters for poly(L-lactic Acid) Under High-Pressure Steam", Polymer Degradation and Stability, vol. 93, 2008, pp. 1053-1058.

Ahmed, Jasim et al., "Handbook of Food Process Design—Chapter 6—Chemical Reaction Kinetics Pertaining to Foods", First Edition, Blackwell Publishing Ltd., 2012, pp. 113-166.

Al-Itry, Racha et al., "Improvement of Thermal Stability, Rheological and Mechanical Properties of PLA, PBAT and Their Blends by Reactive Extrusion with Functionalized Epoxy", Polymer Degradation and Stability, vol. 97, 2012, pp. 1898-1914.

Al-Itry, Racha et al., "Reactive Extrusion of PLA, PBAT with a Multi-Functional Epoxide: Physico-Chemical and Rheological Properties", European Polymer Journal, vol. 58, 2014, pp. 90-102.

Alvarez, V.A. et al., "Thermal Degradation of Cellulose Derivatives/Starch Blends and Sisal Fibre Biocomposites", Polymer Degradation and Stability, vol. 84, 2004, pp. 13-21.

ASTM International, "Designation: D4754-11, Standard Test Method for Two-Sided Liquid Extraction of Plastic Materials Using FDA Migration Cell", 2013, 5 pages.

(56) References Cited

OTHER PUBLICATIONS

Auras, Rafael et al., "An Overview of Polylactides as Packaging Materials", Macromed. Biosci., vol. 4, 2004, pp. 835-864.

Auras, Rafael et al., "Evaluation of Oriented Poly(lactide) Polymers with Existing PET and Oriented PS for Fresh Food Service Containers", School of Packaging, MSU, East Lansing, MI; California Polytechnic University, San Luis Obispo, CA, Packag. Technol. Sci., vol. 18, 2005, pp. 207-216.

Auras, Rafael et al., "Abstract of Poly(Lactic Acid): Synthesis, Structures, Properties, Processing, and Applications", Wiley & Sons, Inc., 2010, 6 pages.

Balat, Mustafa et al., "Recent Trends in Global Production and Utilization of Bio-Ethanol Fuel", Applied Energy, vol. 86, 2009, pp. 2273-2282.

Beck, James V. et al., "Parameter Estimation in Engineering and Science—Chapter 6 (Now Chapter 5)", Wiliey & Sons, NY, 1977, republished Feb. 1999 and Mar. 2007, pp. 5.1-5.81.

Bernard, Samuel et al., "Kinetic Modeling of the Polymer-Derived Ceramics Route: Investigation of the Thermal Decomposition Kinetics of Poly [B-(methylamino)borazine] Precursors Into Boron Nitride", J. Phys. Chem. B, vol. 110, 2006, pp. 9048-9060.

Bikiaris, Demetris N. et al., "Chain Extension of Polyesters PET and PBT with Two New Diimiododiepoxides. II", Journal of Polymer Science: Part A: Polymer Chemistry, vol. 34, 1996, pp. 1337-1342.

Bleach, N.C. et al., "Effect of Filler Type on the Mechanical Properties of Self-Reinforced Polylactide-Calcium Phosphate Composites", Journal of Materials Science: Materials in Medicine, vol. 12, 2001, pp. 911-915.

Box, George E.P., "Fittig Empirical Data" Annals of New York Academy Science, vol. 86, 1960, pp. 792-816.

Cai, Jie et al., "Isothermal Crystallization Kinetics of Thermoplastic Starch/Poly(lactic acid) Composites", Carbohydrate Polymers, vol. 86, 2011, pp. 941-947.

Cailloux, J. et al., "Sheets of Branched Poly(lactic acid) Obtained by One Step Reactive Extrusion Calendarig Process: Melt Rheology Analysis", eXpress Polymer Letters, vol. 7, No. 3, 2013, pp. 304-318.

Canevarolo, Sebastiao, "Chain Scission Distribution Functin for Polypropylene Degradation During Multiple Extrusions", Polymer Degradation and Stability, vol. 709, 2000, pp. 71-76.

Castro-Aguirre, Edgar et al., "Impact of Nanoclays on the Biodegradaton of Poly(lactic acid) Nanocomposites", Polymers, vol. 10, No. 202, 2018, pp. 1-21.

Castro-Aguirre, Edgar et al., "Poly(lactic acid)—Mass Production, Processing, Industrial Applications, and End of Life", Advanced Drug Delivery Reviews, 2016, pp. 1-34.

Chang, Yaw-Nan et al., "Use of Low MW Polylactic Acid and Lactide to Stimulate Growth and Yield of Soybeans", Plant Growth Regulation, vol. 19, 1996, pp. 223-232.

Chariyachotilert, Chaiyatas et al., "Assessment of the Properties of poly(L-lactic acid) Sheets Produced with Differing Amounts of Postconsumer Recycled poly(L-lactic acid)", Journal of Plastic Film & Sheeting, vol. 28, No. 4, 2012, pp. 315-335.

Chen, Hai-Ming et al., "Molecular Ordering and x'-form Formation of poly(L-lactide) During the Hydrolytic Degradation", Polymer, vol. 54, 2013, pp. 6644-6653.

Codari, F. et al., "Kinetics of the Hydrolytic Degradation of Poly(lactic acid)", Polymer Degradation and Stability, vol. 97, 2012, pp. 2460-2466.

Corre, Yves-Marie et al., "Melt Strengthening of Poly(lactic acid) Through Reactive Extrusion with Epoxy-Functionalized Chains", Rheol. Acta., vol. 50, 2011, pp. 613-629.

Chu, C.C., "Hydrolytic Degradation of Polyglycolic Acid: Tensile Strength and Crystallinity Study", Journal of Applied Polymer Science, vol. 26, 1981, pp. 1727-1734.

De Jong, S.J. et al., "New Insights into the Hydrolytic Degradation of Poly(lactic acid): Participation of the Alcohol Terminus", Polymer, vol. 42, 2001, pp. 2795-2802.

Dolan, K.D., "Estimation of Kinetic Parameters for Nonisothermal Food Processes", Journal of Food Science, vol. 68, No. 3, 2003, pp. 728-741.

Dolan, Kirk D. et al., "Parameter Estimation in Food Science", Annu. Rev. Food Sci. Technol., vol. 4, 2013, pp. 401-422.

Dubois, Ph. et al., "Macromolecular Engineering of Polylactone and Polylactides. 19. Kinetics of Ring-Opening Polymerization of e-Caprolactone Initiated with Functional Aluminum Alkoxides", Macromolecules, vol. 29, 1996, pp. 1965-1975.

Fang, Xiaoyi et al., "Diffusion of Aromatic Solutes in Aliphatic Polymers Above Glass Transition Temperature", Macromolecules, 2012, pp. a-o.

Fischer, E.W. et al., "Investigation of the Structure of Solution Grown Crystals of Lactide Copolymers by Means of Chemical Reactions", Institute of Physical Chemistry, Polymers, vol. 251, 1973, pp. 980-990.

Fleury, Guillaume et al., "Non Linear Rheology for Long Chain Branching Characterization, Comparision of Two Methoodologies: Fourier Transform Rheology and Relaxation", Rheol. Acta., vol. 44, 2004, pp. 174-187.

Fu, Chunhua et al., "Improved Hydrolytic Stability of Poly(DL-lactide) with Epoxidized Soybean Oil", Polymer Degradation and Stability, vol. 95, pp. 485-490.

Fukushima, K. et al., "Biodegradation of Poly(lactic acid) and its Nanocomposites", Polymer Degradation and Stability, vol. 94, 2009, pp. 1646-1655.

Fukushima, K. et al., "Nanocomposites of PLA and PCL Based on Montmorillonite and Sepiolite", Materials Science and Engineering, vol. 29, 2009, pp. 1433-1441.

Fulmer, Gregory R. et al., "NMR Chemical Shifts of Trace Impurities: Common Laboratory Solvents, Organics, and Gases in Deuterated Solvents Relevant to the Organometallic Chemist", Organometallics vol. 29, 2010, pp. 2176-2179.

Gao, Jian et al., "Manipulating Poly(lactic acid) Surface Morphology by Solvent-Induced Crystallization", Applied Surface Science, vol. 261, 2012, pp. 528-535.

Gironi, F. et al., "PLA Chemical Recycling Process Optimization: PLA Solubilization in Organic Solvents", J. Polym. Environ., vol. 24, 2016, pp. 328-333.

Gualandi, Chiara et al., "Ethanol Disinfection Affects Physical Properties and Cell Response of Electrospun Poly(L-lactic acid) Scaffolds", European Polymer Journal, vol. 48, 2012, pp. 2008-2018.

Hagerdal, B. Hahn et al., "Bio-Ethanol—The Fuel of Tomorrow form the Residues of Today", Trends in Biotechnology, vol. 24, No. 12, 2006, pp. 549-556.

Hamad, Kotiba et al., "Recycling of Waste from Polymer Materials: An Overview of the Recent Works", Polymer Degradation and Stability, vol. 98, 2013, pp. 2801-2812.

Haralabakopoulos, A.A. et al., "Chain Extension of Poly(ethylene terephthalate) by Reactive Blending Using Diepoxides", Journal of Applied Polymer Science, vol. 71, 1999, pp. 2121-2127.

Hatzikiriakos, Savvas G., "Long Chain Branching and Polydispersity Effects on the Rheological Properties of Polyethylenes", Polymer Engineering and Science, vol. 40, No. 11, Nov. 2000, pp. 2279-2287.

Helmrotih, Erika et al., "Predictive Modelling of Migration From Packaging Materials into Food Products for Regulatory Purposes", Trends in Food Science & Techology, vol. 13, 2002, pp. 102-109.

Hine, Jack et al., "The Rate of Deuterium Exchange Between Ethanol and Water. A Reinvestigation", Notes, vol. 75, Oct. 9, 1952, pp. 739-740.

Sasaki, S. et al., "Helix Distortion and Crystal Structure of the a-Form of Poly(L-lactide)", Macromolecules, vol. 36, 2003, pp. 8385-8390.

Sato, Shuichi et al., "Effects of Various Liquid Organic Solvents on Solvent-Induced Crystallation of Amorphous Poly (lactic acid) Film", J. Appl. Polym. Sci., 2013, pp. 1607-1617.

Schwaab, Marcia et al., "Optimum Reference Temperature for Reparameterization of the Arrhenius Equation. Part 1: Problems Involving One-Kinetic Constant" Chemical Engineering Science, vol. 62, 2007, pp. 2750-2764.

(56) References Cited

OTHER PUBLICATIONS

Schwaab, Marcia et al., "Optimum Reference Temperature for Reparameterization of the Arrhenius Equation. Part 2: Problems Involving Multiple Reparameterizations", Chemical Engineering Science, vol. 63, 2008, pp. 2895-2906.
Sinclair, Richard G., "Slow-Release Pesticide System", Environmental Science and Technology, vol. 7, No. 10, Oct. 1973, pp. 955-956.
Siparsky, Gerogette L. et al., "Water Transport in Polylactic Acid (PLA), PLA/Polycaprolactone Copolymers, and PLA/Polyethylene Glycol Blends", Journal of Environmental Polymer Degradation, vol. 5, No. 3, 1997, pp. 125-136.
Smith, Danielle F. et al., "Modeling the Effect of Temperature and Water Activity on theThermal Resistance of Salmonella enteritidis PT 30 in Wheat Flour", Journal of Food Protection, vol. 79, No. 12, 2016, pp. 2058-2065.
Sorarú, Gian Domenico et al., "Pyrolysis Kinetics for the Conversion of a Polymer Into an Amorphous Silicon Oxycarbide Ceramic", J. Am. Ceram. Soc., vol. 85, No. 9, 2002, pp. 2181-2187.
Tashiro, Kohji et al., "Molecular Mechanism of Solvent-Induced Crystallation of Syndiotactic Polystyrene Glass. 1. Time-Resolved Measurements of Infrared/Raman Spectra and X-Ray Diffraction", Macromolecules, vol. 34, 2001, pp. 310-315.
Tashiro, Kohji et al., "Molecular Mechanism of Solvent-Induced Crystallation of Syndiotactic Polystyrene Glass. 2. Detection of Enhanced Motion of the Amorphous Chains in the Induction Perod of Crystallization", Macromolecules, vol. 35, 2002, pp. 410-414.
Tham, W. L. et al., "Water Absorption Kinetics and Hygrothermal Aging of Poly(lactic acid) Contaiing Halloysite Nanoclay and Maleated Rubber", J. Polym. Environ., vol. 23, 2015, pp. 242-250.
Tolgyessy, "3. The Chemistry of Water", Elsevier Science Publisher, Amsterdam, The Netherlands, 1993, pp. 14-19.
Tsai, W.-C. et al., "Physical Changes and Sorption/Desportion Behaviour of Amorphous and Semi-Crystalline PLLA Exposed to Water, Methanol and Ethanol", European Polymer Journal, vol. 76, pp. 278-293.
Tsuji, Hideto et al., "Blends of Crystalline and Amorphous Poly(lactide). III. Hydrolysis of Solution-Cast Blend Films", Wiley & Sons, 1997, pp. 855-863.
Tsuji, Hideto et al., "Comparative Study on Hydrolytic Degradation and Monomer Recovery of Poly(L-lactic acid) in the Solid and in the Melt", Polymer Degradation and Stability, vol. 93, 2008, pp. 1956-1963.
Tsuji, Hideto et al., "In Vitro Hydrolysis of Poly(L-lactide) Crystalline Residues as Extended-Chain Crystallites. Part I: Long-Term Hydrolysis in Phospate-Buffered Solution at 37 Degrees Celcius", Biomaterials, vol. 25, 2004, pp. 5549-5455.
Tsuji, Hideto et al., "In Vitro Hydrolysis of Poly(L-lactide) Crystalline Residues as Extended-Chain Crystallites: II. Effects of Hydrolysis Temperature", Biomacromolecules, vol. 5, 2004, pp. 1021-1028.
Tsuji, Hideto et al., "Poly(L-lactide): XII. Formation, Growth, and Morphology of Crystalline Residues as Extended-Chain Crystallites Through Hydrolysis of Poly(L-lactide) Films in Phosphate-Buffered Solution", Polymer Degradation and Stability, vol. 84, 2004, pp. 515-523.
Tsuji, Hideto et al., "Ploy(L-lactide), 8a-High-Temperature Hydrolysis of Poly(L-lactide) Films with Different Crystallinities and Crystalline Thicknesses in Phosphate-Buffered Solution", Macromol. Mater. Eng., vol. 286, 2001, pp. 398-406.
Tsuji, Hideto et al., "Hydrolytic Degradation of Linear 2-Arm and Branched 4-Arm Poly(DL-lactide)s: Effects of Branching and Terminal Hydroxyl Groups", Polymer Degradation and Stabilty, vol. 102, 2014, pp. 59-66.
Tsuji, Hideto et al., "A New Strategy for Recycling and Preparation of Poly(L-lactic acid): Hydrolysis in the Melt", Biomacromolecules, vol. 4, 2003, pp. 835-840.
Tsuji, Hideto et al., "Poly(L-lactide): V. Effects of Storage in Swelling Solvents on Physical Properties and Structure of Poly(L-lactide)", Wiley & Sons, Journal of Applied Polymer Science, vol. 79, 2001, pp. 1582-1589.
Tsuji, Hideto et al., "Properties and Morphology of Poly(L-lactide). II Hydrolysis in Alkaline Solution", Wiley & Sons, Journal of Polymer Science, Part A: Polymer Chemistry, vol. 36, 1998, pp. 59-66.
Tsuneizumi, Yota et al., "Chemical Recycling of Poly(lactic acid)-Based Polymer Blends Using Environmentally Benign Cayalysts", Polymer Degradation and Stability, vol. 95, 2010, pp. 1387-1393.
Villalobos, M. et al., "Oligomeric ChainExtenders for Economic Reprocessing and Recycling of Condensation Plastics", Energy, vol. 31 2006, pp. 3227-3234.
Vinckler, Inge et al., "Manifestation of Phase Separation Processes in Oscillatory Shear: Droplet-Matrix Systems Versus Co-Continuous Morphologies", Rheol. Acta, vol. 38, 1999, pp. 274-286.
Vink, Erwin T.H. et al., "Life Cycle Inventory and Impact Assessment Data for 2014 Ingeo Polylactide Production", Industrial Biotechnology, vol. 11, No. 3, Jun. 2015, pp. 167-183.
Vrentas, J.S. et al., "Energy Effects for Solvent-Diffusion in Polymer-Solvent Systems", Macromolecules, vol. 26, 1993, pp. 1277-1281.
Vrentas, J.S. et al., "Fickian Diffusion in Glassy Polymer-Solvent Systems", Journal of Polymer Science, Part B: Polymer Physics, vol. 30, 1992, pp. 1005-1011.
Verentas, J.S. et al., "Predictive Methods for Self-Diffusion and Mutual Diffusion Coefficients in Polymer-Solvent Systems", Eur. Polym. J., vol. 14, No. 5/6, 1998, pp. 797-803.
Vrentas J.S. et al., "Solvent Self-Diffusion in Glassy Polmer-Solvent Systems", Macromolecules, vol. 27, 1994, pp. 5570-5576.
Wachsen, O. et al., "Thermal Decomposition of Biodegradable Polyesters—III. Studies on the Mechanisms of Thermal Degradation of Oligo-L-Lactide Using SEC, LACC and MALDI-TOP-MS", Polymer Degradation and Stability, vol. 55, 1997, pp. 225-231.
Wachsen, O. et al., "Thermal Degradation of Poly-L-Lactide-Studies on Kinetics, Modelling and Melt Stabilisation", Polymer Degradation and Stability, vol. 57, 1997, pp. 87-94.
Wagner, C. et al., "A Theoretical Method for Resolving Overlapping Peaks in Differential Scanning Calorimetry", Materials Letters, vol. 18, 1994, pp. 280-285.
Wang, Liangyan et al., "Blends of Linear and Long-Chain Branched Poly(L-lactide)s with High Melt Strength and Fast Crystallation Rate", Ind. Eng. Chem. Res., vol. 51, 2012, pp. 10088-10099.
Weir, N.A. et al., "Degradation of Poly-L-Lactide. Part 2: Increased Temperature Accelerated Degradation", Proc. Instn. Mech. Engrs., vol. 218, Part H: J. Engineering in Medicine, Mar. 2004, pp. 321-330.
Wojdyr, Marcin, "Fityk: A General-Purpose Peak Fitting Program", J. Appl. Cryst., vol. 43, 2010, pp. 1126-1128.
Wu, Ningjine et al., "Solvent-Induced Crystallation Behaviors of PLLA Ultrathin Films Investigated by RAIR Spectroscopy and AFM Measurements", J. Phys. Chem. B., vol. 8, 2014, pp. 12652-12659.
Xiang, Chunhui et al., "Controlled Release of Nonionic Compounds from Poly(lactic acid)/Cellulose Nanocrystal Nanocomposite Fibers", J. Appl. Polym. Sci., 2013, pp. 79-86.
Yang, Xiaoyi et al., "Kinetic Studies of Overlapping Pyrolysis Reactions in Industrial Waste Activated Sludge", Bioresource Techology, vol. 100, 2000, pp. 3663-3668.
You, Jinxiu et al., "The Preparation and Crystallization of Long Chain Branching Polylactide Made by Melt Radicals Reaction", J. Appl. Polym. Sci., 2013, pp. 1959-1970.
Yuan, Xiaoyan et al., "In Vitro Degradatin of Poly(L-lactic acid) Fibers in Phosphate Buffered Saline", Journal of Applied Polymer Science, vol. 85, 2002, pp. 936-943.
Yuan, Xiaoyan et al., "Surface Degradation of Poly(L-lactic acid) Fibres in a Concentrated Alkaline Solution", Polymer Degradation and Stability, vol. 79, 2003, pp. 45-52.
Zhang, Lijuan et al., "A Dissolution-Diffusion Model and Quantitative Analysis of Drug Controlled Release from Biodegradable Polymer Microspheres", The Canadian Journal of Chemical Engineering, vol. 84, Oct. 2006, pp. 558-566.

(56) References Cited

OTHER PUBLICATIONS

Zhang, Xiaoqing et al., "Morphological Behaviour of Poly(lactic acid) During Hydrolytic Degradation", Polymer Degradation and Stability, vol. 93, 2008, pp. 1964-1979.

Zhou, Q. et al., "Nanoclay and Crystallinity Effects on the Hydrolytic Degradation of Polylactides", Polymer Degradation and Stability, vol. 93, 2008, pp. 1450-1459.

Thou, Huajun et al., "The Thermal Effects on Electrospinning of Polylactic Acid Melts", Polymer, vol. 47, 2006, pp. 7497-7505.

\* cited by examiner

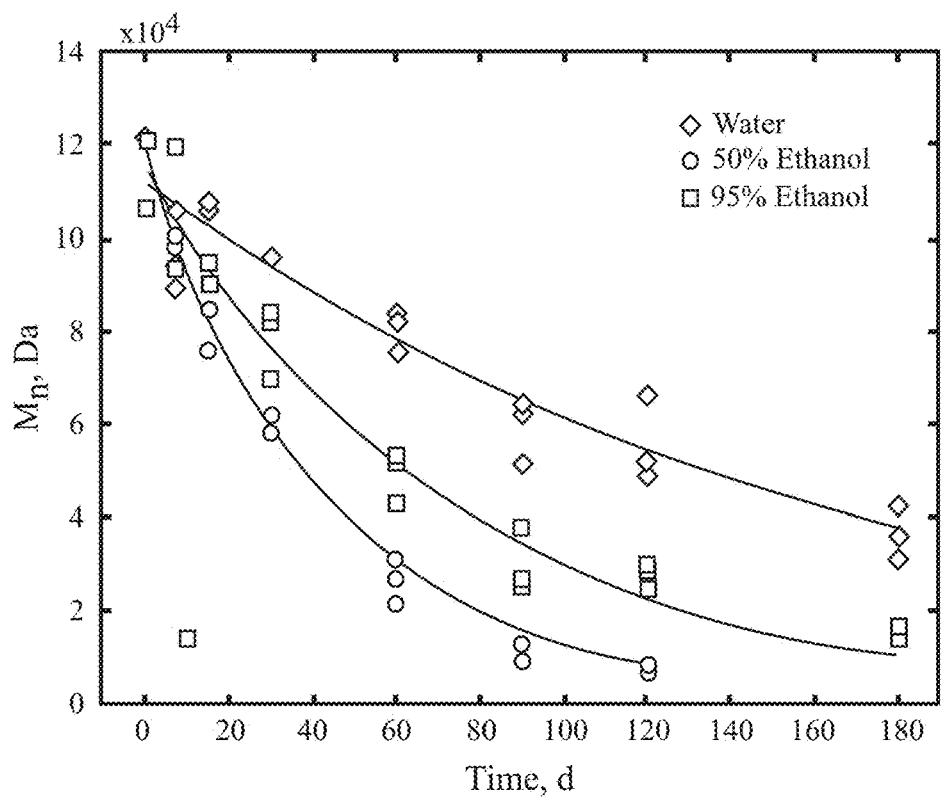

FIG. 4

| | k (d⁻¹) for H₂O or D₂O/ethanol solutions | | |
|---|---|---|---|
| Solvent solution | H₂O* | H₂O** | D₂O*** |
| Water | 0.0059 ± 0.0004[a] | 0.0059 | 0.0020 ± 0.0002[a] |
| 50% Ethanol | 0.0223 ± 0.0010[b] | 0.0230 | 0.0124 ± 0.0007[b] |
| 95% Ethanol | 0.0133 ± 0.0004[c] | 0.0115 | 0.0111 ± 0.0012[b] |

*Fitting of first order reaction: $M_n = M_{no}\exp(-kt)$, where $M_n$ is the number average molecular weight at time $t$ and $M_{no}$ is the initial $M_n$.
**Fitting of first order reaction with $k$ from Eq. 3
***Fitting of first order reaction kinetic. Synthetic data was used for calculations assuming a first order reaction since only the first and last points were measured.
Values with different lower case letters in the same column are statistically different ($a$=0.05 Tukey-Kramer Test)

FIG. 5

| Vapor | $D \times 10^{13}$ (m²/s) |
|---|---|
| H$_2$O | 5.09 ± 0.07[a] |
| D$_2$O | 4.75 ± 0.30[a] |

Values with the same letter are not statistically different ($a$=0.05 Tukey-Kramer Test)
Note: D values were calculated using $D = l^2/7.2\, t_{1/2}$ where $l$ is thickness and $t_{1/2}$ is the half time

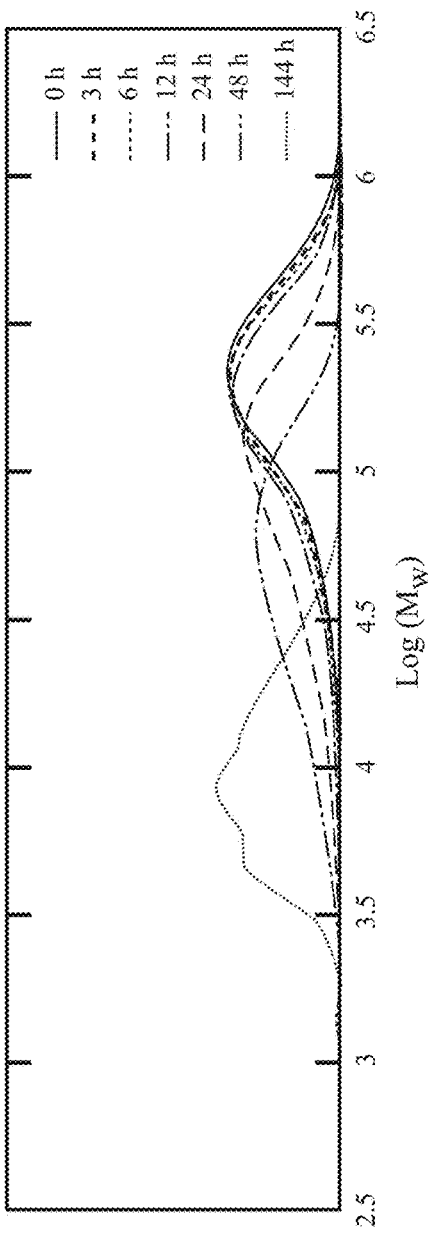
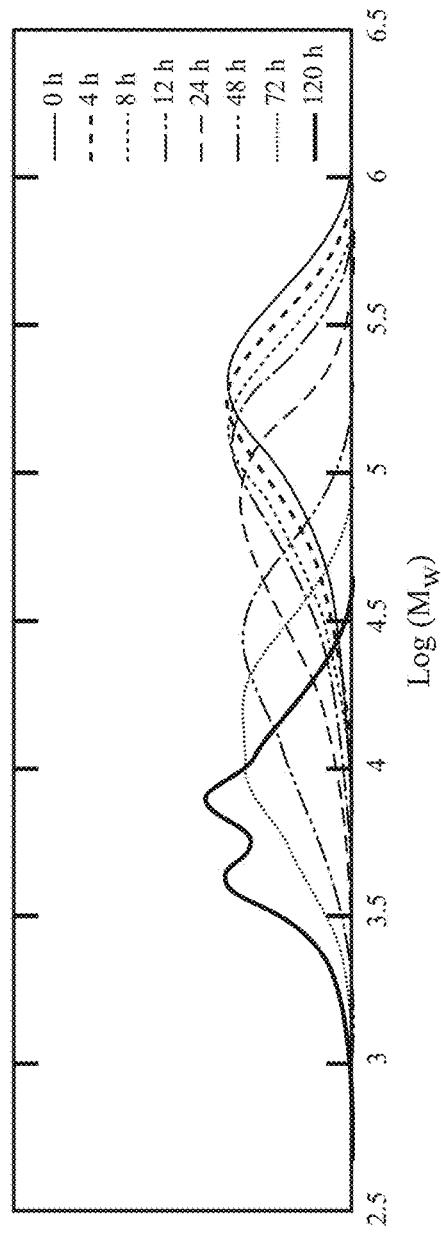
FIG. 21C
FIG. 21D

| Temperature (°C) | $n^*$ | | $k\ (h^{-1})^{**}$ | |
| --- | --- | --- | --- | --- |
| | 50% Ethanol | Water | 50% Ethanol | Water |
| 40 | 1.016 ± 0.050 | nd | 0.0011 ± 0.00004a | nd |
| 60 | 1.056 ± 0.073 | 1.054 ± 0.0977 | 0.0092 ± 0.0006b,A | 0.0043 ± 0.0002a,B |
| 70 | 1.039 ± 0.078 | 1.007 ± 0.0612 | 0.0331 ± 0.0019c,A | 0.0181 ± 0.0007b,B |
| 80 | 1.032 ± 0.042 | 1.043 ± 0.0732 | 0.0553 ± 0.0029d,A | 0.0506 ± 0.0021c,A |
| 90 | nd | 1.048 ± 0.0752 | nd | 0.0916 ± 0.0054d |

*Fitting of general rate law Eq. (1).
**Fitting of first order reaction Eq. (2).
Values with the same lowercase letter within a column and capital letter within a row are not significantly different ($\alpha = 0.05$).
Note: Not determined (nd) since water at 40°C is below the $T_g$ of PLA, and ethanol at 90°C is close to the boiling point of the solution.

FIG. 24

| Parameter | $k_o$ | $E_a$ | Relative error, % |
| --- | --- | --- | --- |
| $k_o$ | 1 | 0.9998 | 328.45 |
| $E_a$ | 0.9998 | 1 | 14.94 |

FIG. 25

| pH | $n$* | $k$ (h$^{-1}$)** |
|---|---|---|
| 4 | 1.002 ± 0.048 | 0.0623 + 0.0032$^a$ |
| 7 | 1.008 ± 0.044 | 0.0530 + 0.0020$^a$ |
| 11 | 1.001 ± 0.039 | 0.2563 + 0.0139$^b$ |

*Fitting of the general rate law Eq. (1).
**Fitting of first order reaction Eq. (2).
Values with different lower case letters are statistically different ($a$ = 0.05 Tukey-Kramer Test).

FIG. 27

| Parameter | Estimates | RMSE, x10$^4$ |
|---|---|---|
| $K_{ref}$, h$^{-1}$ | 0.1004 ± 0.0052 | 1.1737 |
| $M_{no}$, Da | 117,920 ± 2917 | |
| β | 0.2153 ± 0.0148 | |

FIG. 28

| Solution | $T_{ref}$, °C | Parameter | | | RMSE, x$10^3$ |
|---|---|---|---|---|---|
| | | $k_{ref}$, h$^{-1}$ | $M_{no}$, Da | $E_a$, x $10^4$, J/mol | |
| 50% Ethanol, pH correction* | 56.538 | 0.0093 ± 0.00031 | 114,480 ± 1879 | 9.589 ± 0.1559[a] | 8.1062 |
| 50% Ethanol** | 57.688 | 0.0076 ± 0.00027 | 110,840 ± 1625 | 9.341 ± 0.1669[a] | 7.2478 |
| Water** | 75.931 | 0.0276 ± 0.00078 | 115,290 ± 1744 | 10.143 ± 0.2228[b] | 6.4603 |

*Estimated by using Eq. (33).
**Estimated by using Eq. (32).
Values with different lower case letters within a row are different ($a = 0.05$).
Note: $T_{ref}$ values are expressed with three decimals for parameter estimation purposes to get near zero correlation between $k_{ref}$ and $E_a$.

FIG. 29

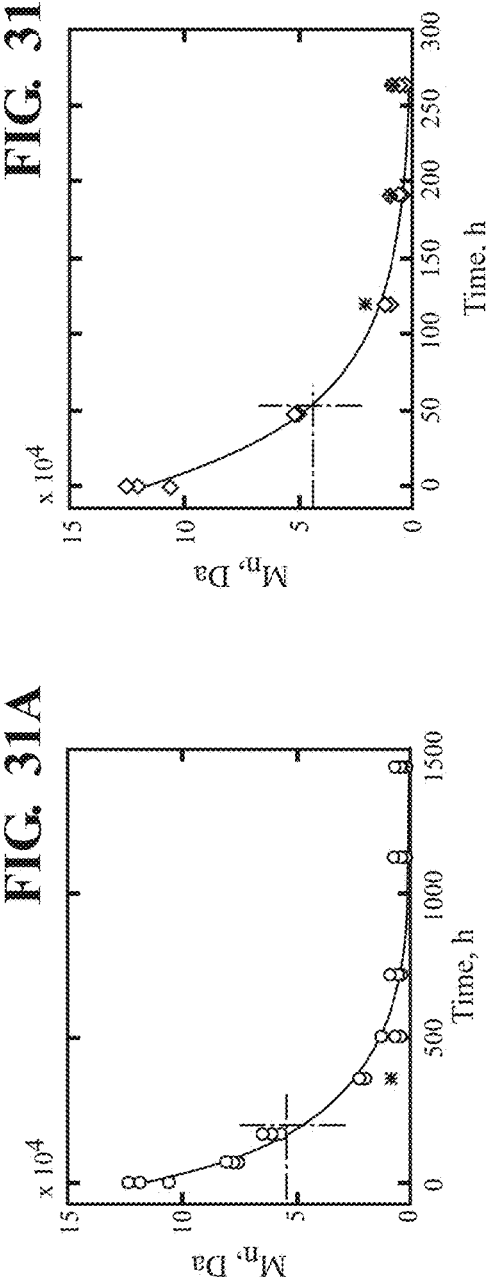
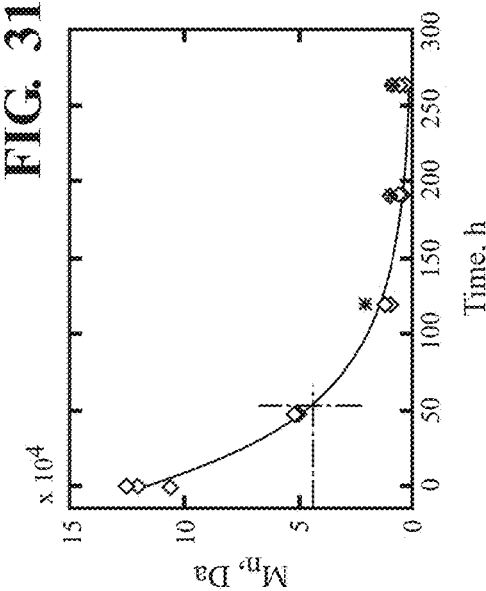
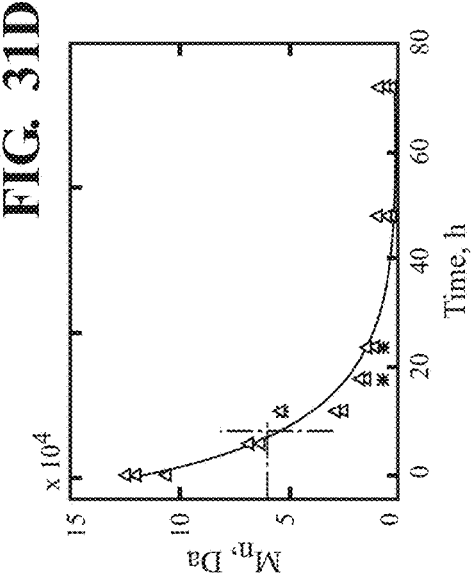
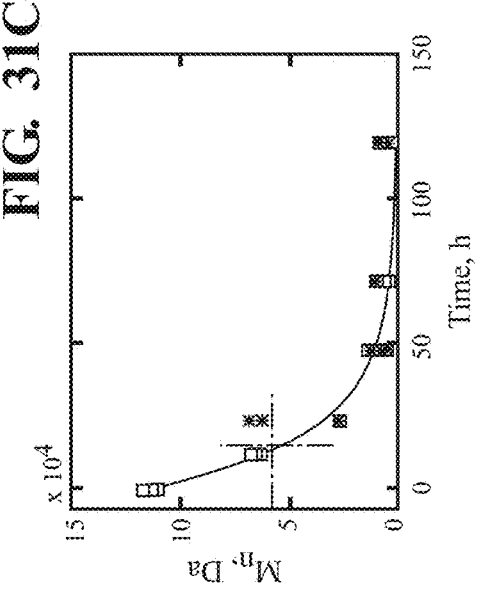
FIG. 31A
FIG. 31B
FIG. 31C
FIG. 31D

| Compound | Group | Chemical Shift (ppm) | Multiplicity, coupling constant, #protons |
|---|---|---|---|
| PLA | -O-CH-CH3-COO- | 5.14 | q, J=7.1 Hz, 1 |
| PLA | -O-CH-CH3-COO- | 1.56 | d, J=7.2 Hz, 3 |
| Ethanol | CH3-CH2-OH | 1.22 | t, J=7.0 Hz, 3 |
| Ethanol | CH3-CH2-OH | 3.70 | q, J=6.9 Hz, 2 |

FIG. 34

| Temperature (°C) | k (h⁻¹)* | time, h |
|---|---|---|
| 40 | 0.000929 ± 0.00004 | 7749 |
| 60 | 0.0075 ± 0.0003 | 919 |
| 70 | 0.0335 ± 0.0036 | 214 |
| 80 | 0.0438 ± 0.0026 | 159 |
| 80, pH 11 | 0.1972 ± 0.0139 | 36 |
| 100, pH 11 | 0.7416 ± 0.0384 | 10 |

*Fitting of first order reaction: $M_n = M_{n0}exp(-kt)$, where $M_n$ is the number average molecular weight at time $t$ and $M_{n0}$ is the initial $M_n$. Values with different lower case letters are statistically different ($\alpha$=0.05 Tukey-Kramer Test).

| Solvent | D x 10$^{14}$ (m$^2$/s) | M$_\infty$ (g-EtOH/g-PLA)* |
|---|---|---|
| 50% Ethanol | 0.64 ± 0.1$^a$ | 0.03 ± 0.0007$^a$ |
| 95% Ethanol | 1.47 ± 0.33$^b$ | 0.08 ± 0.0014$^b$ |

Values with different letter within the same column are statistically different ($a$=0.05 Tukey-Kramer Test)
*Note: grams of ethanol sorbed divided by grams of the PLA disk used for the $^1$H-NMR experiments

FIG. 38

| Solvent | Swelling (wt%) | Boiling Point (°C) | | | Price/ton ($USD) |
|---|---|---|---|---|---|
| | | 40% Alcohol-60% Water | 50% Alcohol-50% Water | 60% Alcohol-40% Water | |
| Ethanol | 8.7 | 94 | 92 | 90 | 950-1000 |
| Methanol | 14 | 79 | 76 | 74 | 500-800 |
| 1-propanol | 7.5 | 88.3 | 88.1 | 87.9 | 1740 |
| 1-butanol | 20.4 | 93.09 | 93.13 | 93.19 | 1000-1500 |

FIG. 39

| Parameter | Value |
|---|---|
| $\hat{V}_1^0(0)$, cm$^3$/mol | 69.2 |
| $\hat{V}_c$, cm$^3$/mol | 259.5 |
| R, J/Kmol | 8.314 |
| $M_1$, g/mol | 90 |
| $\bar{D}_0$, cm$^2$/s | 2.146 x10$^{-9}$ |
| $K_{11}/\gamma_1$, Kcm$^3$/g | 0.0145 |
| $K_{21} - T_{g1}$, K | 10.46 |
| $C_1^g$, K$^{-1}$ | 3.24 |
| $C_2^g$, K | 164.9 |
| $\alpha_2$, C$^{-1}$ | 7.4 x10$^{-4}$ |
| $\hat{V}_2^0(0)$, cm$^3$/g | 0.7214, 0.7116 and 0.7024* |
| $K_{12}/\gamma_2$, cm$^3$/g | 5.863 x10$^{-4}$, 5.783 x10$^{-4}$ and 5.708 x10$^{-4}$* |
| $\hat{V}_2^0(T_{g2})$, cm$^3$/g | 0.8105, 0.7995 and 0.7892* |
| E*, J/mol | 2.4564 x10$^4$ |
| $\omega_1$ | 0 |
| $\omega_2$ | 1 |
| $\xi$ | 0.65 |
| $\alpha$ | 5.5, 4.2 and 3.3* |

*Values for water, 50% and 95% ethanol, respectively.

FIG. 40

METHOD OF RECYCLING A POLYESTER

CROSS-REFERENCE TO RELATED APPLICATION

A method of recycling a polyester is disclosed. The method includes the steps of providing the polyester, preparing a solution containing water and an alcohol, submerging the polyester in the solution, and hydrolytically depolymerizing the polyester while the polyester is submerged in the solution. Depolymerization reduces the polyester to its monomer form for subsequent use in the production of a new polyester.

FIELD OF THE DISCLOSURE

The present disclosure generally relates to a method of recycling a polyester.

BACKGROUND

Recycling of polymers may be accomplished utilizing mechanical or chemical recycling techniques. Mechanical recycling of the polymer typically involves the steps of recovering, sorting, regrinding, and reprocessing of the polymer. While mechanical recycling requires relatively simple technologies and/or techniques, the process(es) often deteriorate(s) the physical properties of the polymer, such as by reducing the molecular weight of the polymer due, at least in part, to mechanical shearing techniques and/or high processing temperature(s). In addition, contaminants available on the polymer and/or produced during mechanical recycling are typically not completely removed.

In chemical recycling, the polymer is depolymerized or converted back into its monomer form utilizing, for example, hydrolysis or alcoholysis techniques. Contaminants produced during the chemical recycling are then separated from the monomer utilizing suitable chemical separation techniques. The monomer can then be used as a raw material to form a new polymer.

Current depolymerization methods for chemical recycling, however, are typically performed at high temperature (such as above the melting temperature of the polymer) utilizing solvents that are typically environmentally harmful, such as toluene, tetrahydrofuran, dichloromethane, and/or chloroform. Additionally, at high temperature, racemization and/or decomposition of the monomer often occurs, which adversely affects the chemical recycling process and/or the chemical and/or physical properties of the new polymer being formed. The present disclosure is aimed at solving the issue(s) identified above.

SUMMARY

This disclosure provides a method of recycling a polyester. The method comprises the steps of: providing the polyester; preparing a solution containing water and an alcohol; submerging the polyester in the solution; and hydrolytically depolymerizing the polyester while the polyester is submerged in the solution.

BRIEF DESCRIPTION OF THE DRAWINGS

The advantages of the present disclosure will be readily appreciated, as the same becomes better understood by reference to the following detailed description when considered in connection with the accompanying drawings.

FIG. 4 is a graph illustrating the $M_n$ as a function of time during hydrolytic degradation of PLA film immersed in water, 50% ethanol, and 95% ethanol at 40° C. in various experiments.

FIG. 5 is a table illustrating the rate constants for PLA films at 40° C. in water-ethanol solutions in various experiments.

FIGS. 21A-21D are graphs illustrating the MWD of PLA films during hydrolytic degradation when in contact with 50% ethanol at 40° C. (FIG. 21A), 60° C. (FIG. 21B), 70° C. (FIG. 21C), and 80° C. (FIG. 21D).

(FIG. 23A), 60° C. (FIG. 23B), 70° C. (FIG. 23C), and 80° C. (FIG. 23D).

FIG. 24 is a table illustrating the order of reaction (n) and the rate constants (k) for PLA films at different temperatures in 50% ethanol solution and water.

FIG. 25 is a table illustrating the correlation matrix of estimated parameters using the Arrhenius equation for the hydrolytic degradation of PLA in 50% ethanol.

FIG. 27 is a table illustrating the order of reaction (n) and rate constants (k) for PLA films at 80° C. and the different pH values in 50% ethanol solution.

FIG. 28 is a graph illustrating final estimated parameters values at an optimum $pH_{ref}$ value of 7.697.

FIG. 29 is a graph illustrating final estimated parameter values at an optimum reference temperature ($T_{ref}$).

(FIG. 30A), 70° C. (FIG. 30B), 80° C. (FIG. 30C), and 90° C. (FIG. 30D).

FIGS. 31A-31D are graphs illustrating $M_n$ as a function of time during hydrolytic degradation of PLA film immersed in water at 60° C. (FIG. 31A), 70° C. (FIG. 31B), 80° C. (FIG. 31C), and 90° C. (FIG. 31D).

FIG. 34 is a table illustrating the $^1$H-NMR peaks and identification of ethanol in PLA in various embodiments.

FIG. 38 is a table illustrating the D and amount of ethanol at equilibrium ($M_\infty$) in PLA films at 40° C. in various embodiments.

FIG. 39 is a table illustrating the boiling point and swelling ratio of different ethanol solutions to be used to hydrolyze PLA to LA in various embodiments.

FIG. 40 is a table illustrating the parameters for predicting the diffusion coefficient of LA and up to five LA-mers in PLA in various embodiments.

DETAILED DESCRIPTION

Figure 1A:
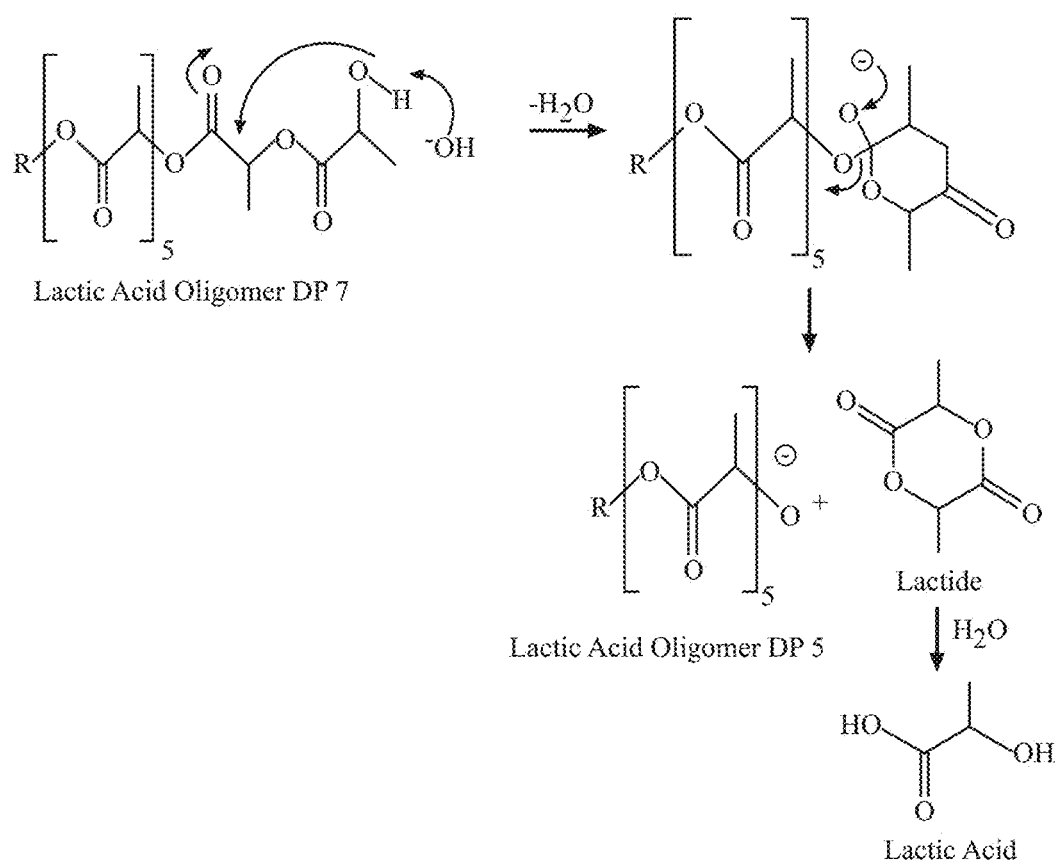
FIGS. 1A and 1B illustrate hydrolytic depolymerization reactions of poly(lactic acid) (PLA) in alkaline (FIG. 1A) and acidic (FIG. 1B) media.

The present disclosure describes a method of recycling a polyester. In the embodiments described in detail below, the method may be described as a chemical recycling method of the polyester utilizing a depolymerization step to reduce the polyester into its monomer form. The monomer formed by the method may then be used as a raw material for the production of a new polyester having the same and/or similar properties as the virgin polyester. The method advantageously reduces or even eliminates the formation of contaminants and/or environmentally harmful byproducts by utilizing one or more "green" solvents, such as an alcohol selected from ethanol, methanol, 1-butanol, and/or 1-propanol, and/or combinations thereof. Additionally, the method may be performed at a low or moderate temperature, such as at a temperature of from about 40 to 80° C., which reduces or even eliminates racemization and/or decomposition of the monomer. This allows for formation of the new polyester having chemical and/or physical properties that are the same/substantially the same and/or similar as the virgin polyester.

Embodiments of the method of recycling the polyester will now be described. The method comprises the step of providing the polyester. The polyester may be any polymer containing an ester group on the primary polymer chain. The polyester may also be any known polyester that swells when contacted with an alcohol. Non-limiting examples of polyesters include thermoplastic polyesters, thermoset polyesters, and polyester resins. In an embodiment, the polyester is further defined as poly(lactic acid) (PLA), and the step of providing the polyester is further defined as providing the poly(lactic acid). In alternative embodiments, the polyester could be further defined as polyglycolic acid (PGA), polycaprolactone (PCL), polyhydroxyalkanoate (PHA), polyethylene terephthalate (PET), polybutylene terephthalate (PBT), and/or the like, and/or combinations thereof.

PLA is a biodegradable thermoplastic aliphatic polyester derived or formed from corn starch or sugar cane utilizing lactic acid (LA) as a precursor. PLA may be used in many different products, including medical products (such as sutures, stents, and drug delivery systems), agricultural products, packaging products (such as film and a rigid thermoforms for containers for food and non-food products), etc. The PLA for the embodiments of the method may be provided by obtaining the PLA from used and/or discarded products, such as used and/or discarded medical, agricultural, and/or packaging products mentioned above. Alternatively, the PLA can be provided by purchasing the PLA from any suitable manufacturer.

In an embodiment, the PLA may be provided in any form, shape, and/or configuration, and the PLA may have suitable any molecular weight and/or molecular size (in terms of monomer units). In a non-limiting example, the PLA has at least 100,000 LA or monomer units. In another non-limiting example, the PLA has from about 100,000 to 150,000 LA or monomer units. In yet another non-limiting example, the PLA has about 130,000 LA or monomer units. It is to be appreciated that the foregoing ranges are not limiting, and the PLA may have a number of monomer units that is larger or smaller than the ranges identified above. Additionally, and in another embodiment, the PLA has a number average molecular weight ($M_n$) of from about $1.21 \times 10^3$ to $1.21 \times 10^6$ Da. In yet another embodiment, the PLA has a weight average molecular weight ($M_w$) of from about $2.5 \times 10^4$ to $2.5 \times 10^6$ Da. The number average molecular weight of the PLA is also non-limiting, and may be larger or smaller than the range identified above.

In an embodiment, the method further includes the step of forming the polyester into a polyester film having a thickness of from about 18 to 38 micrometers. The polyester film may be further defined as a thin film of polyester. The polyester may be formed into the film utilizing any suitable processing technique known in the art including, but not limited to, casting, spraying, extruding, thermoforming, molding, and/or the like.

Once the polyester film has been formed, the method includes the step of reducing the polyester film into a plurality pieces. The step of reducing the polyester film into the plurality of pieces is performed prior to submerging the polyester in a water-alcohol solution, which is described in further detail below. As described in further detail below, reducing the polyester film into the plurality of pieces improves the water-alcohol solution-to-polymer during the depolymerization step. In an embodiment, the step of reducing the polyester film is further defined as cutting the polyester film into a plurality of pieces utilizing any suitable cutting technique. Alternative ways of reducing the polyester film include breaking, trimming, grinding, smashing, etc. the polyester film into the plurality of pieces.

The method further includes the step of preparing a solution containing water and an alcohol. This step of preparing the solution is performed independent of the step of forming the polyester film. In an embodiment, the step of preparing the solution is further defined as combining the water and the alcohol. Combining may be performed by adding the alcohol to the water or by adding the water to the alcohol in a container, vessel, or the like, and mixing the water and alcohol together to form the solution. Mixing may be accomplished utilizing any suitable mixing technique for any suitable time period or duration to form the water-alcohol solution.

In an embodiment, the step of preparing the solution is further defined as preparing the solution containing from about 20 to 70 percent by volume of the alcohol and the balance being water, based on a total of 100 percent by volume of the solution. Without being bound by any particular theory, it has been found hydrolytic degradation of the PLA during the subsequent depolymerization step is faster utilizing a water-alcohol solution with the alcohol present in the amount of from 20 to 70 percent by volume. This is attributed to faster water penetration into the polymer matrix of the PLA starting with chain cleavage or breakage after immediate swelling of the PLA matrix due to the presence of the alcohol molecules. In another embodiment, the step of preparing the solution is further defined as preparing the solution containing from about 40 to 70 percent by volume of the alcohol and the balance being water, based on a total of 100 percent by volume of the solution. In another embodiment, the step of preparing the solution is further defined as preparing the solution containing from about 40 to 50 percent by volume of the alcohol and the balance being water, based on a total of 100 percent by volume of the solution. In another embodiment, the step of preparing the solution is further defined as preparing the solution containing from about 45 to 55 percent by volume of the alcohol and the balance being water, based on a total of 100 percent by volume of the solution. In still another embodiment, the step of preparing the solution is further defined as preparing the solution containing about 50 percent by volume of the alcohol and about 50 percent by volume of the water, based on a total of 100 percent by volume of the solution. Without being bound by any particular theory, it has been found that faster hydrolytic degradation occurs when the PLA is in contact with a solution containing about 50 percent by volume. This is due to a competitive balance between the swelling effect of the alcohol expanding the PLA network, which allows for maximum sorption of the water into the PLA matrix and cleavage of the main chain of the polymer due to hydrolysis. It should be appreciated that the amount of alcohol present in the solution can be any percent by volume falling within the 20 to 70 percent range, with the balance being water.

The alcohol for the solution is not particularly limited. In an embodiment, the alcohol for the solution is selected from ethanol, methanol, 1-butanol, and 1-propanol, and the step of preparing the solution is further defined as preparing a solution of water and an alcohol selected from ethanol, methanol, 1-butanol, and 1-propanol. It should be appreciated that the alcohol may be a combination of two or more of the above-listed alcohols.

In another embodiment, the alcohol is further defined as ethanol and the step of preparing the solution is further defined as preparing the solution containing the ethanol and the water. With the alcohol further defined as ethanol, the step of preparing the solution is further defined as preparing the solution containing from about 40 to 50 percent by volume of ethanol and the balance being water, based on a total of 100 percent by volume of the solution. In yet another embodiment, the alcohol is further defined as 1-butanol and the step of preparing the solution is further defined as preparing the solution containing the 1-butanol and the water. With the alcohol further defined as 1-butanol, the step of preparing the solution is further defined as preparing the solution containing from about 20 to 30 percent by volume of 1-butanol and the balance being water, based on a total of 100 percent by volume of the solution.

In addition, the step of preparing the solution is further defined as preparing a solution of water and an alcohol with the solution having a pH of from 10 to 14. In another embodiment, the step of preparing the solution is further defined as preparing a solution of water and an alcohol with the solution having a pH of about 11. In an alternative embodiment, the pH of the solution could be within the acidic range; however, the inventors of the present disclosure have found that hydrolysis of the subsequent hydrolytic depolymerization step increases when the pH of the solution falls within the basic range, particularly at a pH of about 11.

As previously mentioned, the solution contains water. In one embodiment, the water wholly contains hydrogen oxide ($H_2O$) molecules. In another embodiment, the water is further defined as heavy water and the step of preparing the solution is further defined as preparing the solution containing the heavy water and the alcohol. Heavy water may be described as water in which the hydrogen in the water molecules is partly or wholly replaced by the hydrogen isotope deuterium. Heavy water may also be described as an enriched water mixture containing deuterium oxide ($D_2O$), as well as hydrogen-deuterium oxide (DHO) and hydrogen oxide ($H_2O$) molecules.

Once the solution is prepared, the method further comprises the step of submerging the polyester in the solution. The method further includes the step of hydrolytically depolymerizing the polyester while the polyester is submerged in the solution. In an embodiment, a ratio of polyester to water-ethanol solution is from about 1 g of polyester/10 mL of solution to 4 g of polyester/10 mL of solution. Accordingly, the step of hydrolytically depolymerizing the polyester is performed simultaneously with the step of submerging the polyester in the solution. Typically, hydrolytic depolymerization begins as soon as the polyester is submerged in the solution and continues until the polyester is at least partially depolymerized. In an embodiment, the polyester is completely depolymerized during the hydrolytic depolymerizing step. In an embodiment, the step of submerging the polyester includes submerging the polyester in the solution for a time period of from 6 to 3000 hours. In another embodiment, the step of submerging the polyester includes submerging the polyester in the solution for a time period of from 20 to 150 days. In another embodiment, the step of submerging the polyester includes submerging the polyester in the solution for a period of 6 to 41 hours to achieve 95% of depolymerization of the polyester.

As used herein, the term hydrolytic depolymerization describes the depolymerization of the polyester by hydrolysis reaction(s). In essence, the polymer chain(s) of the polyester is/are broken down due to the cleavage of the ester bonds with the water reducing the polyester down into its monomer form. For example, poly(lactic acid) may be hydrolytically depolymerized to reduce the poly(lactic acid) down into lactic acid (the monomer form of poly(lactic acid)). This is accomplished by breaking down the ester linkage between the polymer units/chains. The hydrolytic depolymerizing step may also be performed utilizing a suitable catalyst such as, but not limit to, at least one of a metal compounds, a cationic compound, and an organic compound. Additionally, the step of hydrolytically depolymerizing the polyester is performed at a moderate temperature. For instance, the step of hydrolytically depolymerizing the polyester is further defined as hydrolytically depolymerizing the polyester while submerged in the solution at a temperature of from about 40 to 80° C. As used herein, a temperature falling within the range of from about 40 to 80° C. is considered to be a moderate temperature. In another embodiment, the depolymerizing step is performed at a temperature of about 40, 50, 60, 70, or 80° C., or any value or range of values there-between. In another embodiment, the depolymerizing step takes place at standard pressure, such as at 1 atm. It should be appreciated that depolymerization can also be performed at higher pressures.

Figure 1B:
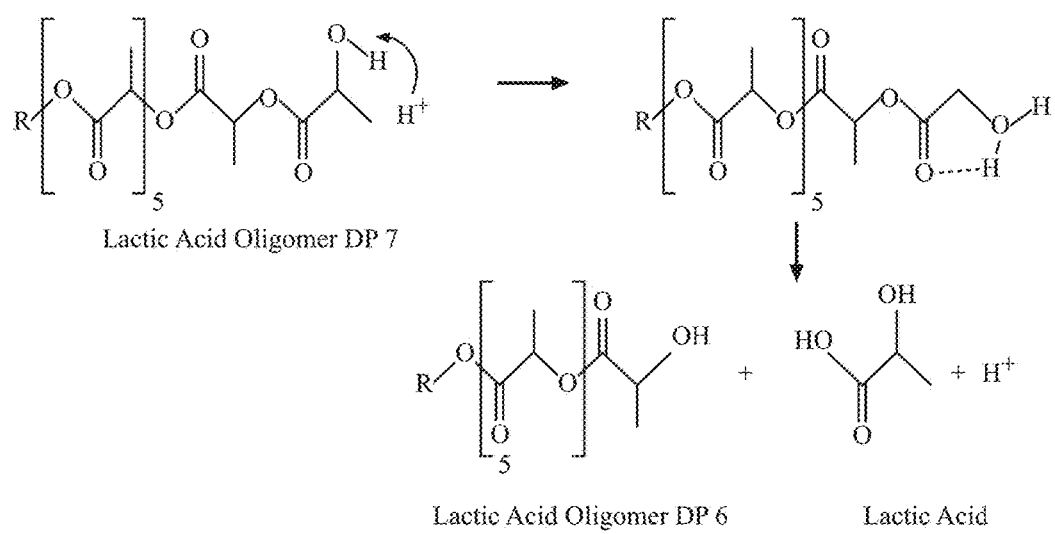

Hydrolytic depolymerization of PLA is illustrated by the chemical reactions shown in FIGS. 1A and 1B. The chemical reaction shown in FIG. 1A illustrates hydrolytic depolymerization or cleavage reaction in alkaline media. The chemical reaction shown in FIG. 1B illustrates hydrolytic depolymerization or cleavage reaction in acidic media. These chemical reactions product lactide, lactic acid, and an oligomer of lactic acid as the main or primary products of PLA hydrolytic depolymerization. Byproducts formed during depolymerization and/or any residual solvent can be separated from the depolymerized polyester (e.g., the monomer) using any standard separation technique, such as membrane separation and distillation.

In an embodiment, the method further comprises the step of analyzing the depolymerized polyester after the step of separating the depolymerized polyester from the solution. Analysis may be formed on the depolymerized polyester, which is or primarily includes the monomer, to determine the suitability of the monomer (such as its purity, etc.) for subsequent processing of the monomer for forming a new polyester having the same/substantially the same chemical and/or physical properties as the virgin polyester. Various known techniques may be used to perform desired analysis/analyses on the monomer.

To further illustrate embodiments of the present disclosure, the following Examples are given herein. It is to be understood that the Examples are provided for illustrative purposes and are not to be construed as limiting the scope of the present disclosure.

EXAMPLES

In various embodiments, PLA films were immersed in pure water, 50% and 95% ethanol solutions for up to 180 days. The change in molecular weight, sorption of water, sorption of ethanol, and lactic acid released were monitored. Glass transition temperature and percent crystallinity as a function of ethanol content were also measured. PLA experienced faster hydrolytic degradation in contact with 50% ethanol than with 95% ethanol or pure water. NMR methodologies were developed to measure sorption of deuterated water and ethanol in PLA. More water was sorbed in 50% ethanol, explaining the higher hydrolysis. During exposure, PLA experienced solvent induced crystallization (SIC). Higher percent crystallinity was found in films exposed to 50% ethanol with the formation of α-form crystals. The hydrolysis of PLA was correlated with the release of lactic acid during exposure. Mathematical models are proposed to explain the concurrent SIC and hydrolytic degradation of PLA.

Figure 2:
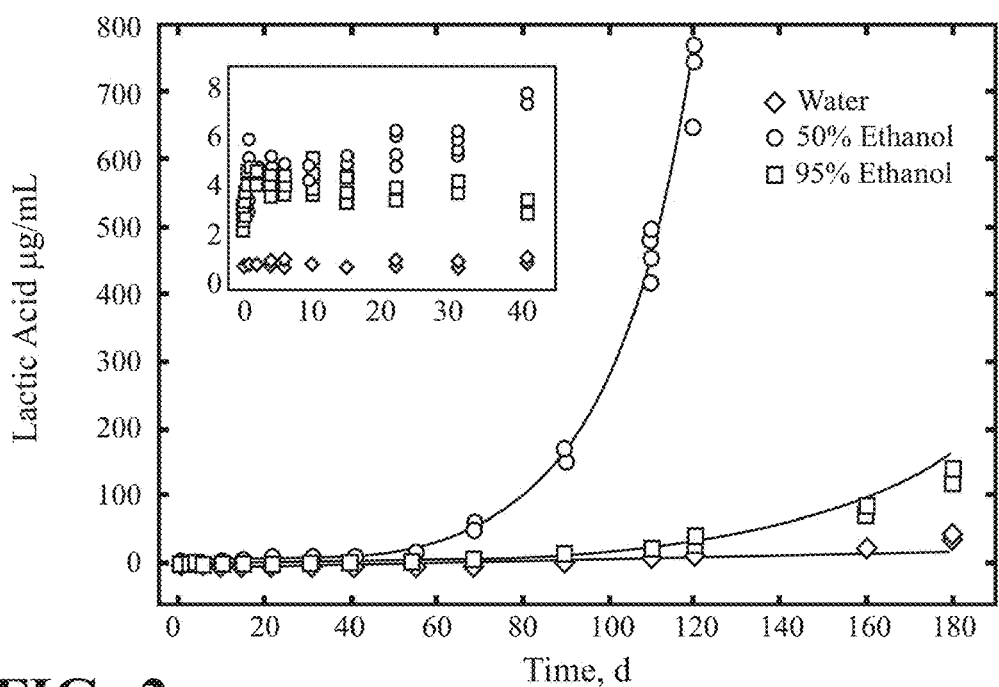
FIG. 2 is a graph illustrating an increasing release of lactic acid during hydrolytic degradation of PLA films in contact with water, a 50% water, and 50% ethanol solution, and with a 5% water and 95% ethanol solution at 40° C.
Figure 3:
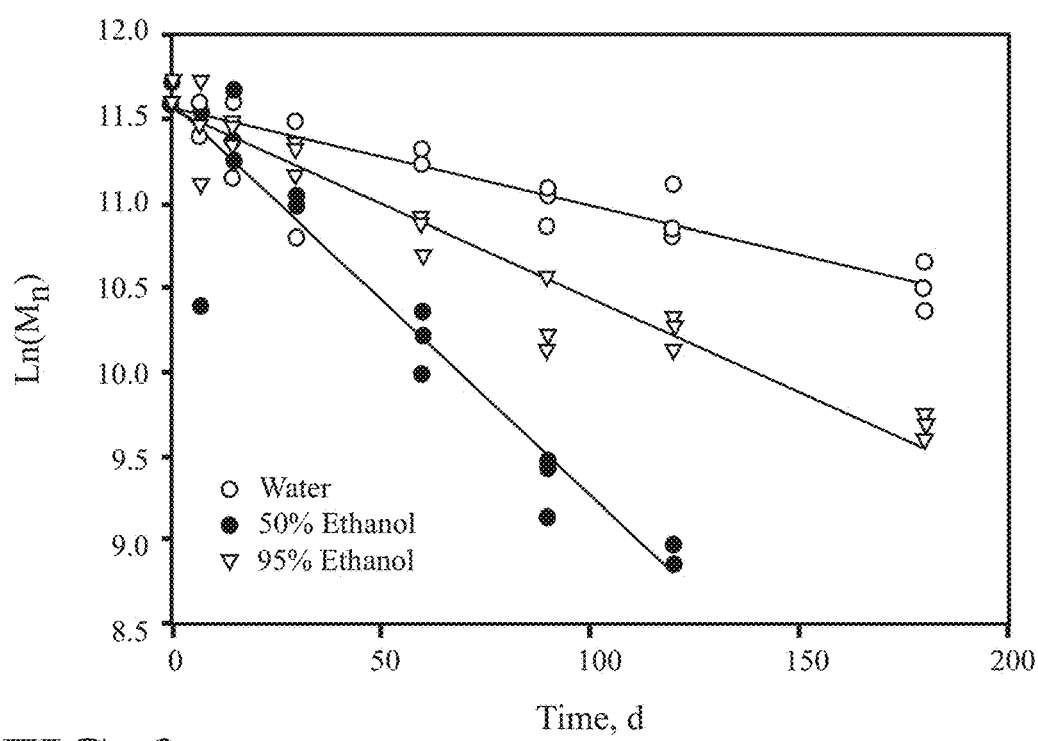
FIG. 3 is a graph illustrating a reduction of number average molecular weight ($M_n$) of PLA in solution containing 50% ethanol, 95% ethanol, and water in various experiments.

FIGS. 2 and 3 demonstrate the feasibility of this approach due to the fast water penetration after immediate swelling of the PLA matrix in a specific water-alcohol solution; accelerating the hydrolytic chain cleavage mechanics of PLA. In FIG. 2, the release of LA during hydrolytic degradation of PLA films in contact with water, 50% and 95% ethanol at 40° C. is shown. In FIG. 3, Ln ($M_n$) is shown as a function of time during hydrolysis of PLA films into water, 95% ethanol or 50% ethanol at 40° C.

Chemicals and reagents used include the following: PLA resin and/or pellets (3.8-4.2% D-LA) with a weight and number average molecular weight ($M_w$, $M_n$) of 2.35±0.07×$10^5$ Da and 1.21±0.08×$10^5$ Da, respectively. In addition, chemicals and reagents include: CAPS (3-(cyclohexylamino)-1-propanesulfonic acid), HEPES (N-(2-Hydroxyethyl)piperazine-N'-(2-ethanesulfonic acid)), sodium citrate, ethanol (HPLC grade), acetonitrile (HPLC grade), methanol (HPLC grade), 1-butanol (HPLC grade), 1-propanol (HPLC grade), formic acid, tetrahydrofuran (THF), water (HPLC grade), L(+) LA, malonic acid, deuterium oxide (D, 99.9%) ($D_2O$) chloroform-D (D, 99.8%) ($CDCl_3$), and N, N-Dimethylformamide (DMF).

The following process carried out the production of PLA film. PLA pellets were dried at 60° C. for 24 h under vacuum (85 kPa) and processed in a Randcastle cast film microextruder with a screw of 1.5875 cm diameter, 24/1 L/D ratio extruder, and 34 cc volume. The extrusion temperatures were 193, 212, 215, 215 and 210° C. for zone 1, 2, and 3 transfer tube and die, respectively, with a rotation speed of from 49-60 rpm. The film thickness was 27.9±9.9 µm.

The storage experiments were conducted as follows. Ten disks 2.0 cm in diameter separated by glass beads on a stainless-steel wire were placed in cells containing pure water, 50% ethanol, or 95% ethanol by volume, previously conditioned at 40° C. The total disk surface area to fluid volume was 1.79 cm$^2$/mL. Degradation and release experiments were conducted at 40° C. using a migration cell.

Preliminary experiments on hydrolytic degradation of PLA were performed in different water alcohol solutions: 50% ethanol, 50% methanol, 50% 1-propanol and 20% 1-butanol by volume at 70° C. All the solutions were preconditioned before testing. After determining 50% ethanol as the main solvent to be used in the study of the Ea of PLA hydrolytic degradation, migration cells containing 50% ethanol by volume were stored at 40, 60, 70 and 80° C. All cells were first conditioned at the set temperature. Cells that contained water were also conditioned and stored at 60, 70, 80 and 90° C. Experiments designed to control the pH of the 50% ethanol solution during the hydrolytic degradation of PLA were performed at 80° C. with pH values of 4, 7 and 11, using sodium citrate (0.1M), HEPES (0.3M) and CAPS (0.1M) as buffer solutions, respectively. Samples of film were retrieved periodically to assess number average molecular weight ($M_n$), weight average molecular weight (Mw) and polydispersity index (PDI). $M_n$ was assessed where 10 mg of film were dissolved in THF (2 mg/mL) and tested using size exclusion chromatography (SEC). The measurements were conducted in triplicate.

To study the hydrolytic degradation and SIC of PLA by water-ethanol solutions, the change in molecular weight of PLA was analyzed during exposure to determine the rate of hydrolysis caused by the cleavage of the ester bonds. The sorption of water in PLA was studied since hydrolysis depends on the presence of water molecules in the polymer matrix. However, the ethanol molecules in the solvent solutions influenced the water sorption in PLA due to the swelling effect. Swelling studies were carried out and the initial first order reaction equation for $M_n$ reduction was modified to account the effect of PLA swelling in the rate constant. Crystallinity studies of PLA were performed over the exposure time to assess the concurrent SIC by ethanol molecules along with the hydrolysis of amorphous regions in the polymer matrix by water molecules. Finally, LA release was assessed as the result of the concurrent SIC and hydrolysis of the polymer chains and a model was proposed to predict the LA release when PLA is exposed to water-ethanol solutions.

Figure 6A:
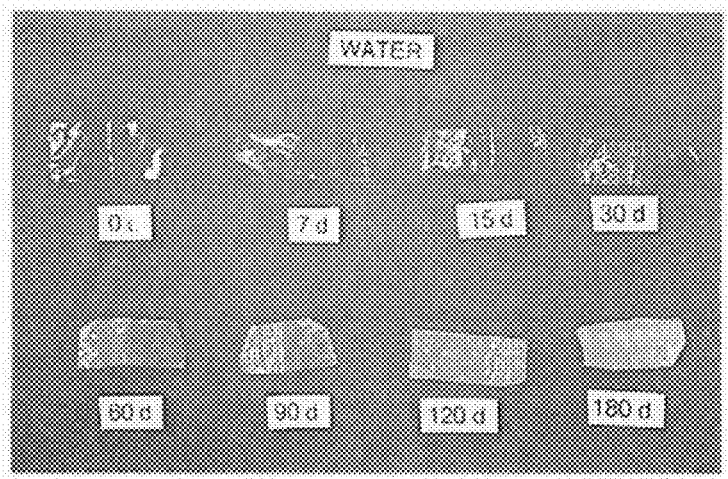
FIGS. 6A-6C are optical images of PLA samples immersed in water (FIG. 6A), a 50% ethanol solution (FIG. 6B), and a 95% ethanol solution (FIG. 6C) during the hydrolytic degradation in various experiments.
Figure 6B:
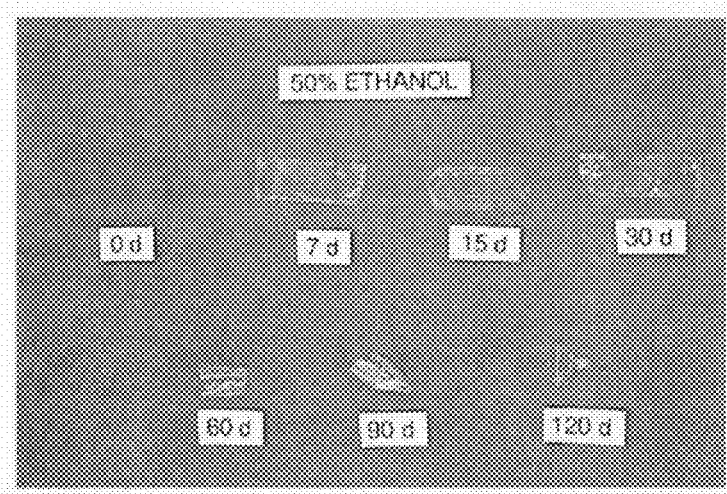
Figure 6C:
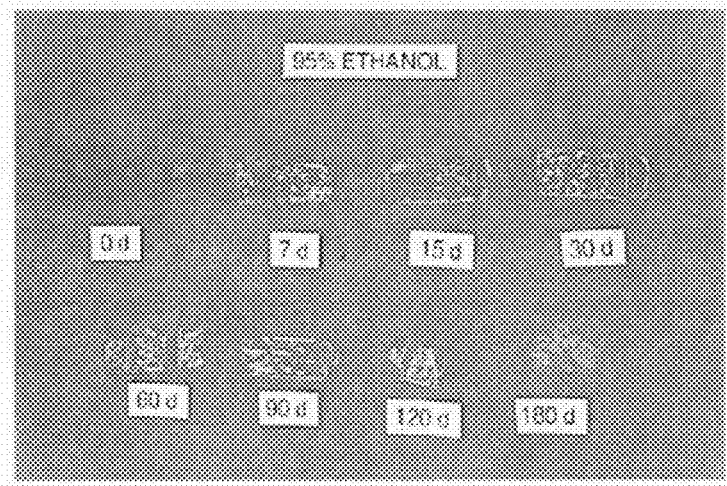

FIG. 4 shows $M_n$ as a function of time for PLA disks immersed in water, 50% ethanol and 95% ethanol at 40° C. Molecular weight decreased over time, indicating hydrolysis of PLA. However, the change in $M_n$ was different for PLA in the three solutions. A first order reaction relationship was fitted to the experimental data. FIG. 5 illustrates the rate constants k (gmol$^{-1}$ d$^{-1}$) for each system. The 50% ethanol solution caused the highest rate of decrease of $M_n$ at 0.0223 gmol gmol$^{-1}$ d$^{-1}$ (p<0.05), followed by 95% ethanol and water at 0.0133 (p<0.05) and 0.0059 gmol$^{-1}$ d$^{-1}$ (p<0.05), respectively. After 120 days, the films in 50% ethanol were no longer intact and dispersed as small fragments in the solvent. The reduction in $M_n$ during exposure is attributed to scission of the ester bond of the polymer chains by water molecules. Optical images of PLA samples immersed in the three different water-ethanol solutions during hydrolytic degradation are presented in FIGS. 6A-6C.

It has been evaluated that the effect of organic solvents like ethanol in contact with PLA swell the polymer matrix and increase chain mobility. The creation of free volume due to swelling allows more water molecules to diffuse in and get sorbed in the PLA matrix. This accelerates the hydrolysis rate. The diffusion and sorption of water and ethanol during hydrolytic degradation can help to describe the mechanism of solvent assisted hydrolysis.

The determination of water and ethanol sorption is as follows. Diffusion of $H_2O$ in PLA has been reported, D values of $3.53 \times 10^{-15}$ m$^2$/s at 80% relative humidity (RH) and $1.5 \times 10^{-11}$ m$^2$/s at 90% RH in vapor systems, and $2.92 \times 10^{-12}$ m$^2$/s in immersion conditions were reported for PLA at 40° C. In various experiment, to simultaneously measure the rate of diffusion and sorption of water in PLA in ethanol solutions created technical challenges since the $H_2O$ peaks overlap with PLA resonances in the $^1$H NMR spectrum.

Furthermore, excluding all extraneous sources of water from NMR measurements to ensure accurate measurements is extremely difficult. In contrast, $D_2O$ does not suffer the same issues and allows for the accurate measurement of sorption.

Figure 7A:
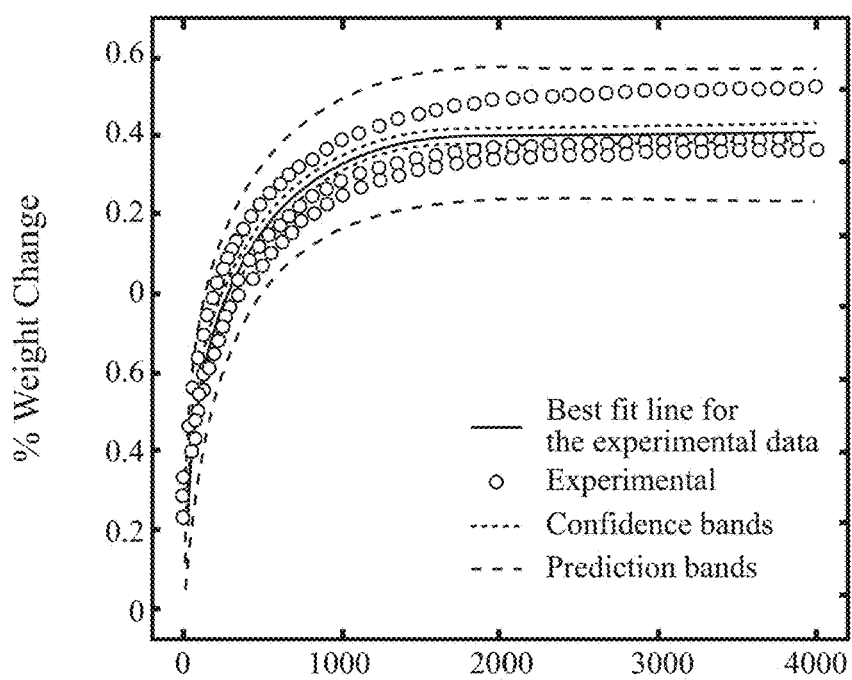
FIGS. 7A and 7B are graphs illustrating the diffusion of deuterium oxide ($D_2O$) (FIG. 7A) and water ($H_2O$) vapor (FIG. 7B) in PLA films at 75% relative humidity and 40° C. in various experiments.
Figure 7B:
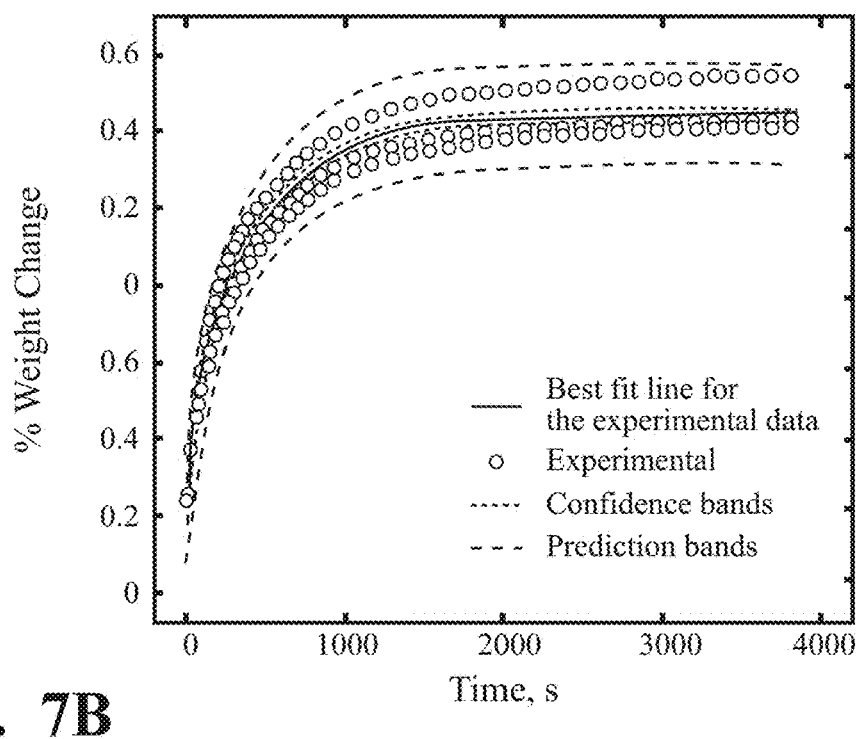

Therefore, $D_2O$ water was used to simulate the diffusion of $H_2O$ in PLA, but recognize that $D_2O$ will cause a different hydrolysis rate in PLA than $H_2O$ as is shown in FIG. 5. Even though $D_2O$ and $H_2O$ may have the same initial diffusion coefficient as shown in FIGS. 7A and 7B, which shows the rate of diffusion of $H_2O$ vapor and $D_2O$ vapor in PLA. The k values will decrease when $H_2O$ is replaced with $D_2O$ since hydrogen isotopes $^1$H in $H_2O$ have been replaced by deuterium isotopes $^2$H, reducing the number of hydroxide (deuteroxide) ions that start the cleavage of the ester bonds.

Figure 8:
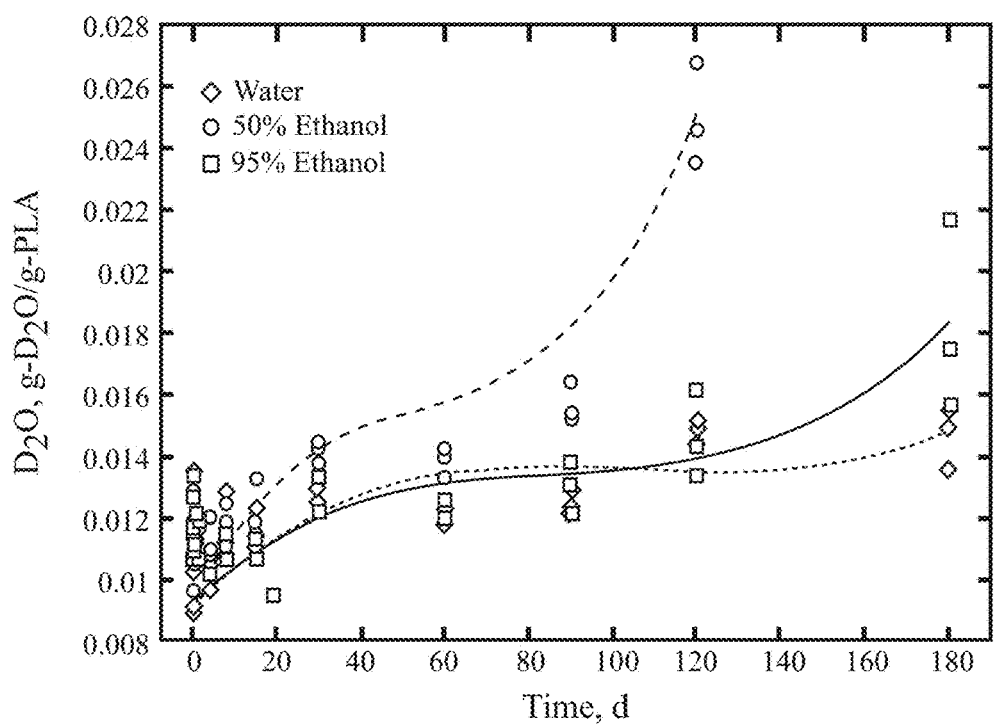
FIG. 8 is a graph illustrating $D_2O$ sorption into PLA films in contact with $D_2O$, 50% ethanol, and 95% ethanol at 40° C. in various experiments.
Figure 9:
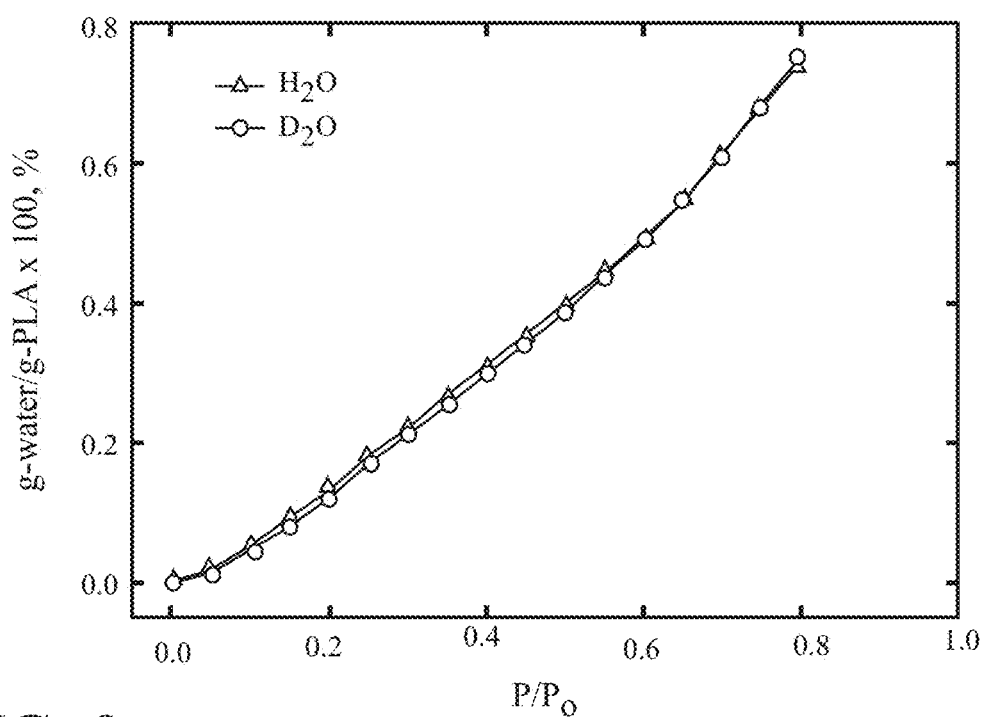
FIG. 9 is a graph illustrating the sorption isotherms for $H_2O$ and $D_2O$ vapor in PLA films at 40° C. in various experiments.

FIG. 8 shows the rate of $D_2O$ sorption by PLA. The concentration of $D_2O$ molecules in PLA was lowest when the films were immersed in $D_2O$ and highest when immersed in 50% ethanol. The higher the concentration of $D_2O$ in the PLA, the faster the hydrolysis by $D_2O$, since there are more molecules of $D_2O$ available to start the cleavage of ester bonds. However, faster cleavage can be expected if $H_2O$ were used due to the reactivity of hydroxyl groups, even though the sorption of $H_2O$ vapor and $D_2O$ vapor into PLA are similar (FIG. 9).

Figure 10A:
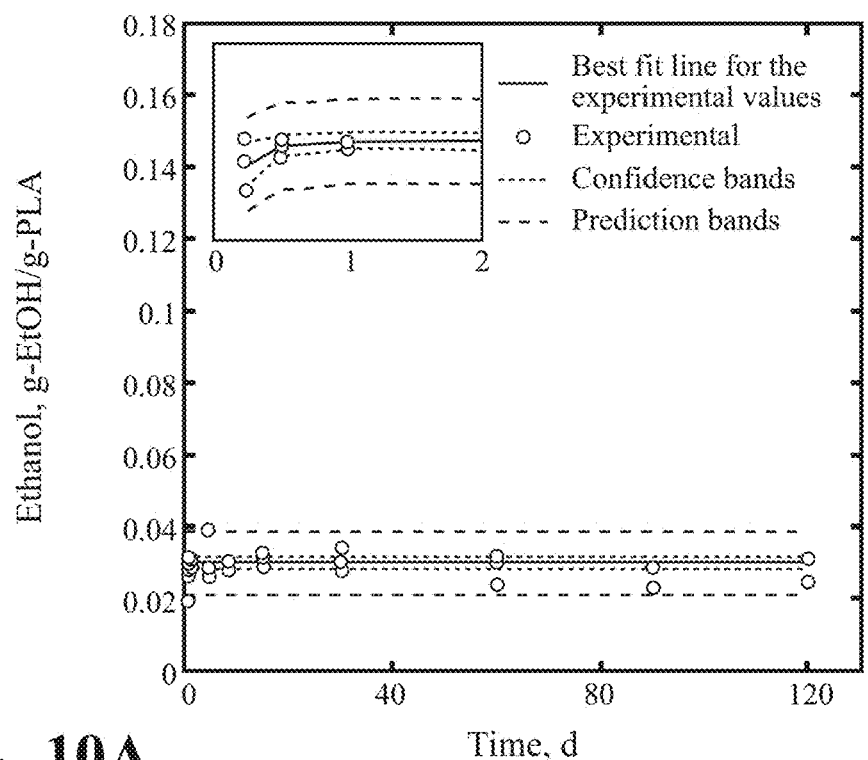
FIGS. 10A and 10B are graphs illustrating the immediate ethanol sorption into PLA films in contact with 50% ethanol (FIG. 10A) and 95% ethanol (FIG. 10B) at 40° C. during hydrolysis in various experiments.
Figure 10B:
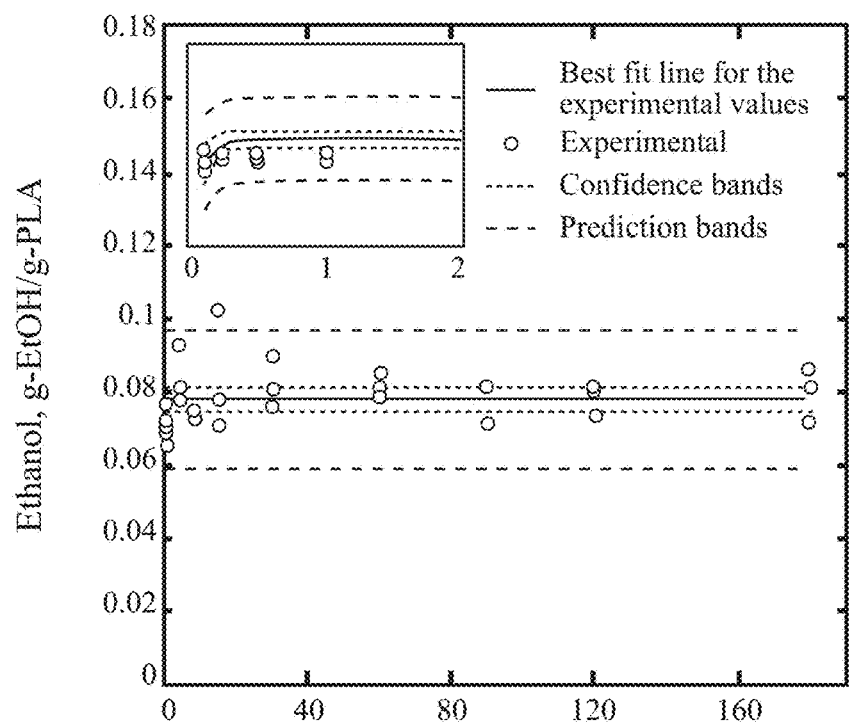
Figures 11, 12:
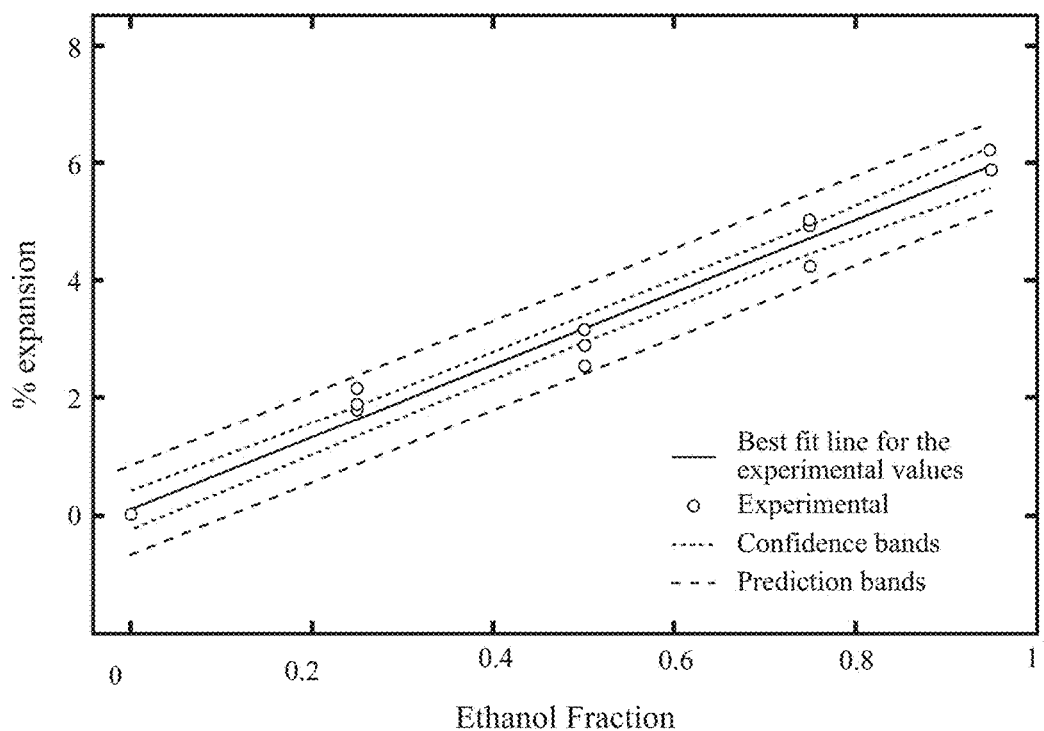
FIG. 11 is a table illustrating the diffusion coefficient (D) of $H_2O$ and $D_2O$ vapor in PLA films at 75% relative humidity and 40° C. in various embodiments.
FIG. 12 is a graph illustrating the expansion and/or swelling of PLA in contact with different volume fractions of ethanol in various experiments.

FIGS. 10A and 10B show immediate ethanol sorption in PLA during hydrolysis. Diffusion coefficients were estimated using Eq. (1) (set forth below) taking into account the swelled thickness of the PLA films at equilibrium (i.e., the initial thickness was 27.94 μm and the final estimated thicknesses based on expansion for 50% and 95% ethanol were 28.78 and 29.53 μm, respectively). Additionally, the estimated parameters, D for ethanol in disks immersed in 95% ethanol ($5.88 \times 10^{-14}$ m$^2$/s) was almost twice the D for ethanol in disks immersed in 50% ethanol ($2.55 \times 10^{-14}$ m$^2$/s). The amount of ethanol at equilibrium (Mm) was 160% higher in 95% ethanol than in 50% ethanol. FIG. 11 is a table illustrating the diffusion coefficient (D) of $H_2O$ and $D_2O$ vapor in PLA films at 75% relative humidity and 40° C.

Ethanol sorption appears to follow Fick's law of diffusion. The analytical solution with constant concentration assumed on both disk faces is:

$$\frac{M_t}{M_\infty} = 1 - \frac{8}{\pi^2} \sum_{n=0}^{\infty} \frac{1}{(2n+1)^2} \exp\left(\frac{-D(2N+1)^2 \pi^2 t}{t^2}\right) \quad \text{(Eq. 1)}$$

where $M_t$ is the amount of ethanol sorbed at time t (g-EtOH/g-PLA), $M_\infty$, is the amount of ethanol at equilibrium (g-EtOH/g-PLA), t is time(s), l is thickness of the expanded disk (m) and D is the diffusion coefficient (m²/s). The nonlinear regression (nlin-fit) function in MATLAB® 2011b (MathWorks, Natick, Mass.) was used to fit Eq. (1). This provides an estimate of $M_\infty$ and D.

Experiments were performed using the $^1$H NMR technique to study the relationship between ethanol concentration and polymer expansion when PLA films were exposed to different concentrations of ethanol over 24 h. FIG. 12 shows the relationship between % expansion of PLA and ethanol fraction (volume of ethanol divided by total volume).

The initial first order reaction $M_n = Mn_0 \exp(-kt)$, can be modified to account for the effect of PLA swelling. A model based on the assumption that the expansion of the polymer is due to an increase in void space, not expansion of the chains, predicts that the rate constant is:

$$k = \beta\left[\frac{V_o}{V_d} + \left(0.06 - \frac{V_o}{V_d}\right)p - 0.06p^2\right] \quad \text{(Eq. 2)}$$

where $V_o$ is the initial void space in the PLA matrix. $V_d$ is the volume of the disk, p is a constant, and p is the ethanol fraction (p=0, 0.5, 0.95). This model incorporates the effect of expansion due to ethanol in the rate constant. When p=0 (pure water), $k=\beta V_o/V_d$; and when p=1 (no water), k=0. Fitting $M_n = M_{no}\exp(-kt)$ to the experimental data in FIG. 4 with k defined in Eq. (2) gives $\beta=1.05$ and $V_o/V_d=0.0056$. Using $V_d=0.0088$ cm³, the initial void space ($V_o$) in one disk is predicted to be $4.93\times10^{-5}$ cm³. FIG. 5 illustrates the rate constants using Eq. (2).

Figure 13:
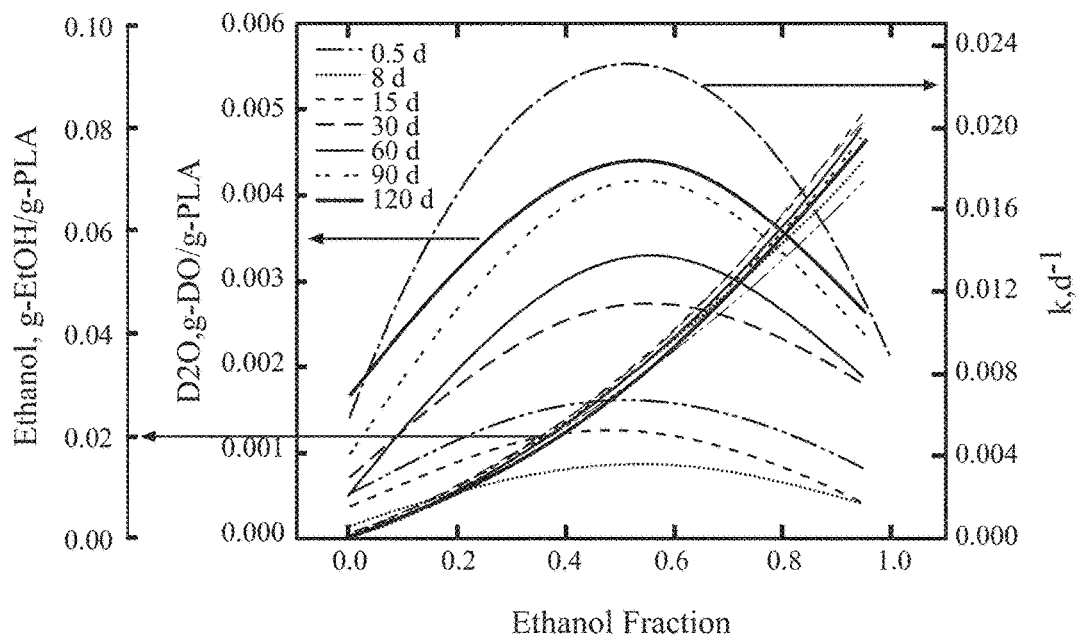
FIG. 13 is a graph illustrating the rate constant for hydrolytic degradation of PLA films fitting the first order reaction equation with k from Eq. (2) below where $D_2O$ and ethanol sorption lines were obtained from experimental data of PLA immersed in water, 50% ethanol, and 95% ethanol at different exposure times for various embodiments.

Setting the derivative of k with respect to p in Eq. (2) equal to zero gives the maximum rate of decay in $M_n$. This occurs when the volume fraction of ethanol reaches p≈0.45 (FIG. 13). At that concentration of ethanol, a competitive balance between swelling and hydrolysis is observed, where the molecules of ethanol swell the polymer and allow the maximum concentration of water into the polymer to start the cleavage of the ester bonds.

Hydrolytic degradation of PLA occurs in the amorphous regions since they have a larger void volume than the crystalline regions and water can penetrate amorphous regions more readily. Since hydrolysis reduces the amorphous regions, the degree of crystallinity increases, even though the crystalline regions remain unchanged. On the other hand, exposure of PLA to ethanol causes softening in the polymer, resulting in the movement and realignment of polymer chains, which induces crystallinity. Therefore, it is a combination of structural changes in PLA including swelling and induced crystallinity when exposed to different combined solvents that affects hydrolysis.

Figure 14:
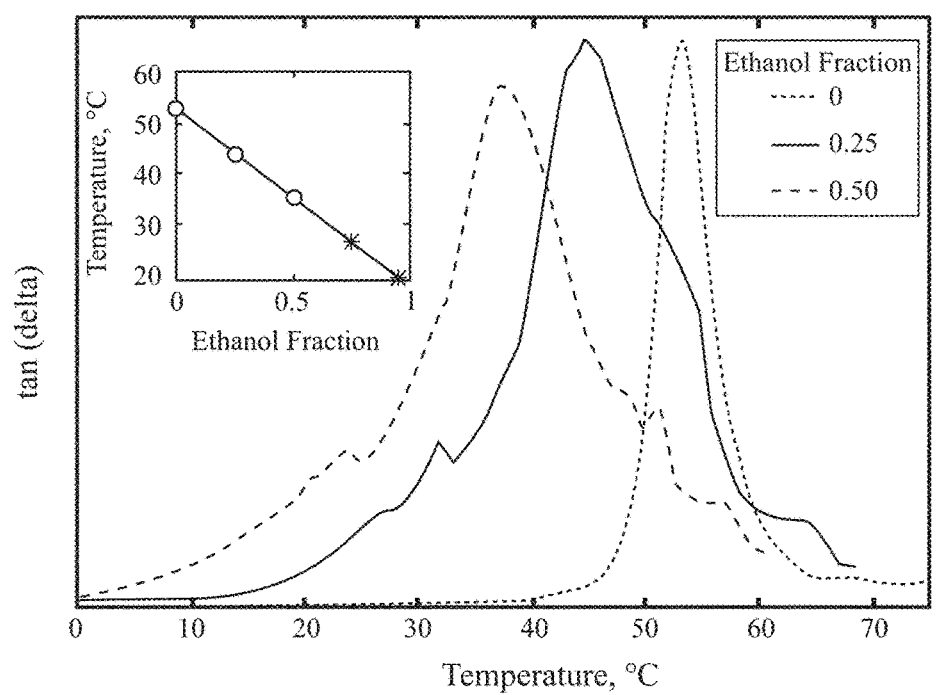
FIG. 14 is a graph illustrating the change in glass transition temperature ($T_g$) of PLA when immersed in different volume fractions of ethanol at 40° C. in various experiments.

FIG. 14 shows the change in $T_g$ of PLA when immersed in different volume fractions of ethanol at 40° C. The relationship is linear. The $T_g$ of the PLA films before being exposed to hydrolytic degradation was 59.8±0.5° C. according to the DSC results. PLA films immersed in 100% water had a $T_g$ of 53° C., but when PLA was immersed in 50% and 95% ethanol, $T_g$ was approximately 36 and 20° C., respectively. This means that the higher the concentration of ethanol in the solution, the lower the $T_g$ during solvent transport into PLA, where swelling occurs immediately according to FIGS. 10A and 10B. The plasticization effect of ethanol on PLA allows the movement of the polymer chains, inducing alignment so crystallinity can occur.

For assessing the crystallinity of PLA during hydrolytic degradation, DSC and XRD techniques were used. DSC was applied to calculate the percent crystallinity and identify changes in $T_m$, $T_C$, and $T_g$ using DSC thermograms. The identification of the type of crystals formed during PLA hydrolysis was performed by the XRD technique.

Figure 15:
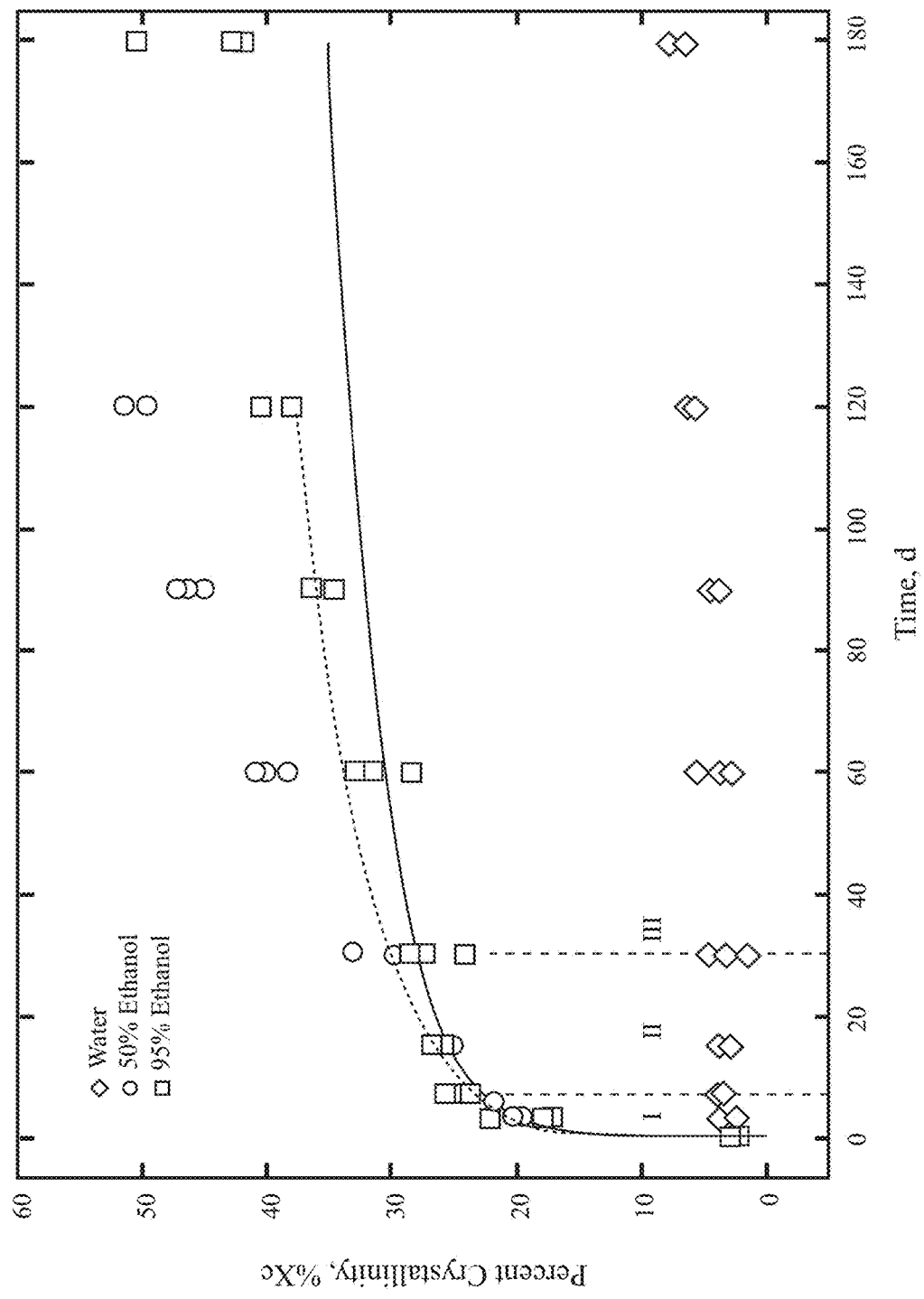
FIG. 15 is a graph illustrating the percent crystallinity (% $X_c$) as function of time obtained by differential scanning calorimetry (DSC) technique during hydrolytic degradation of PLA films immersed in water, 50% ethanol, and 95% ethanol at 40° C. in various experiments.

FIG. 15 shows the percent crystallinity (% $X_C$) obtained by the DSC technique during hydrolytic degradation of PLA as a function of time. The crystallinity of samples exposed to water increased from 2.8 to 7.3% after 6 months of immersion. For PLA films exposed to ethanol solutions, the crystallinity increased dramatically. After the first 15 days of immersion, the crystallinity of PLA in 50% and 95% ethanol was the same, around 26%. After one month, the 50% ethanol samples started showing higher crystallinity. In another embodiment, the increase on crystallinity during hydrolytic degradation has also been observed when PLA has been exposed to different environments and pH.

The increase in crystallinity can be explained by the depression of $T_g$ due to the process of SIC. If $T_g$ falls below the test temperature (40° C.), the polymer chains have sufficient mobility and tend to rearrange into a crystalline structure, which is a more stable configuration. It has been found that the transport of acetone in poly(ethylene terephthalate) (PET) induces crystallization in three stages. The first stage is the transport of the solvent by diffusion, which is controlled by the concentration gradient. The second stage involves swelling by the solvent and the third stage is secondary crystallization, in the case of PLA, the second stage present in PET is observed in FIG. 15 as the region marked with region I due to the dramatic increase in swelling by ethanol, as measured by the change in film thickness. In this region, primary crystallization takes place, where large amounts of crystallites are formed as a result of relaxation of constraints by the release of internal stress, where chains begin to fold and become crystals. When the system is in saturation (region II), the crystallization rate is slow and polymer chains can form small crystals dispersed in the amorphous region, corresponding to a secondary crystallization. After 30 days in 95% ethanol, the crystallinity started to increase (region III). This can be explained by the preferential hydrolysis of the amorphous regions left after secondary crystallization, which increases the net crystalline region as degradation proceeds. For PLA in contact with 50% ethanol, crystallization due to hydrolysis started after 15 days of exposure, resulting in a higher % $X_C$ than films immersed in 95% ethanol. The higher % $X_C$ can be explained by the higher solubility of water molecules in the amorphous regions, hydrolyzing them faster and therefore increasing the net crystalline regions.

In order to quantify the crystallization kinetics, the Avrami theory was applied according to:

$$X_c = 1 - \exp(-Kt^n) \quad \text{(Eq. 3)}$$

where $X_c$ is the relative crystallinity of the polymer, t is time, K is the crystallization rate constant, and n is the Avrami exponent. As observed in FIG. 15, the Avrami model fits regions I and II well. The deviation from the Avrami equation in region III is due to the hydrolysis of the amorphous region and not to the formation of new crystals. The Avrami kinetic parameters of crystallinity for 50% ethanol were K=0.018 s$^{-1}$ and n=0.20, and for 95% ethanol were K=0.031 s$^{-1}$ and n=0.16. Generally, the n values reported are around 2 and 4. The low values obtained are in accordance with recently reported values, where PLA was exposed to methanol and ethanol, giving values of 1 and 0.5, respectively. This is an indication of the uni-dimensional growth of crystals restricted by diffusion of the solvent.

Figure 16A:
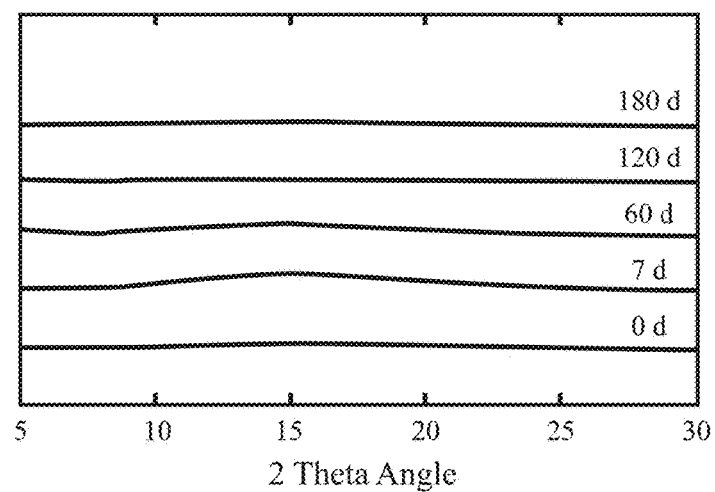
FIGS. 16A-16C are graphs illustrating the x-ray diffraction (XRD) profiles as a function of time of the PLA films during the hydrolytic degradation in various experiments.
Figure 16B:
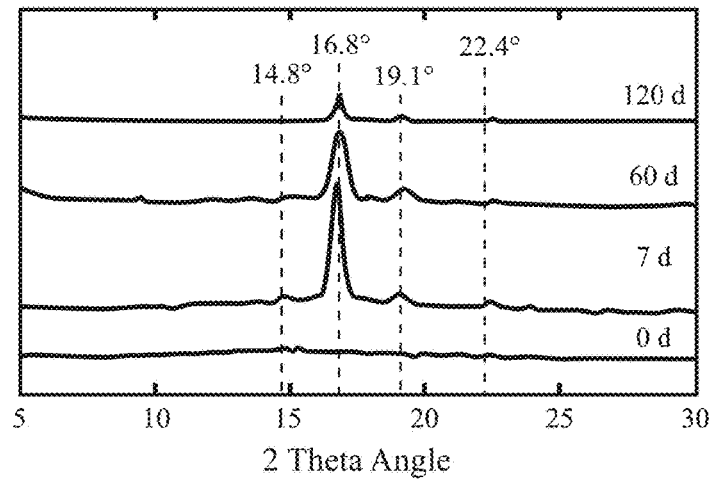
Figure 16C:
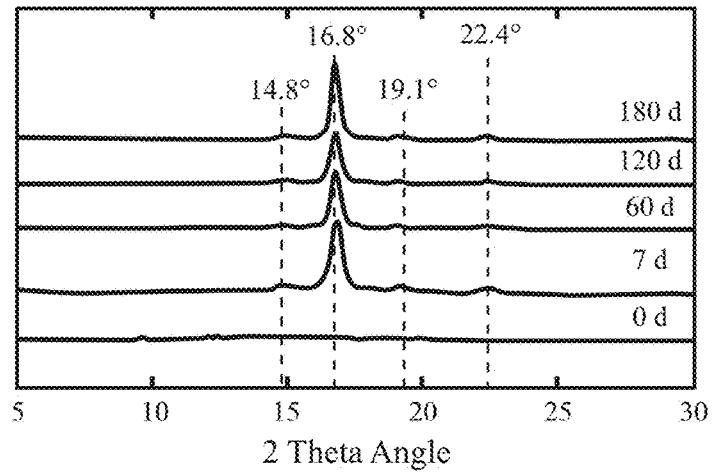

The XRD profiles of PLA films during hydrolytic degradation are shown in FIGS. 16A-16C. When PLA was immersed in pure water, the profiles showed broad peaks during hydrolysis. These results indicate that PLA immersed in pure water remained amorphous during hydrolysis. No formation of crystals took place, which is in agreement with the 3% increase in crystallinity during degradation.

Figure 16D:
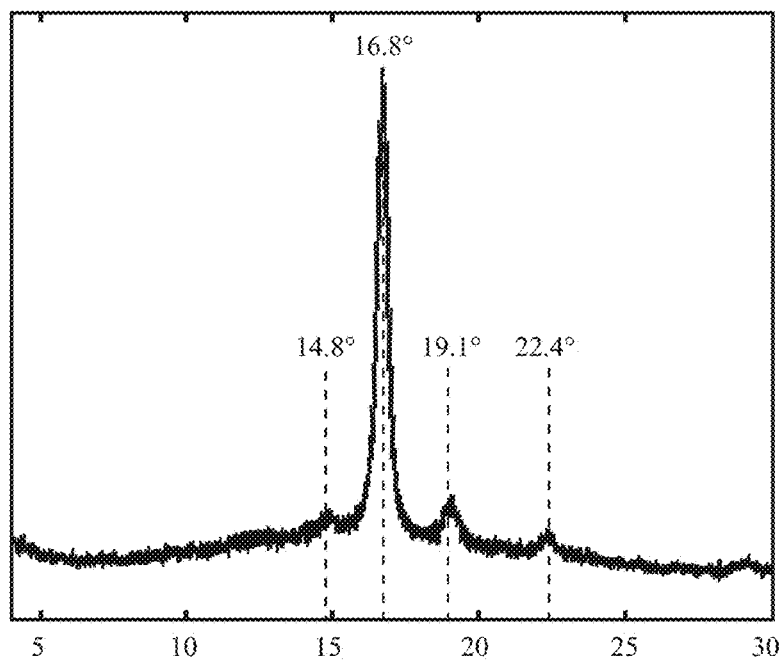
FIG. 16D is a graph illustrating the XRD profiles of PLA films during the hydrolytic degradation after three days exposure to 50% ethanol in various experiments.
Figure 16E:
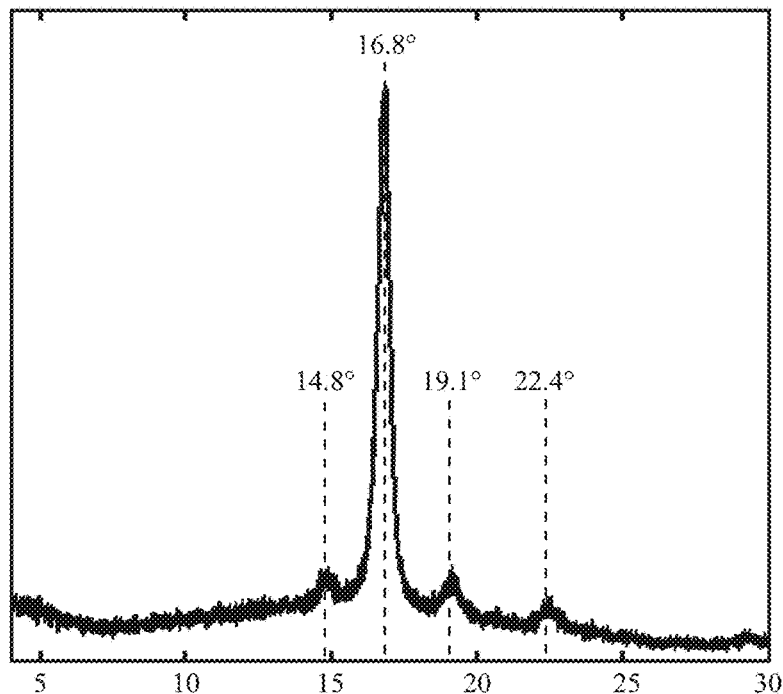
FIG. 16E is a graph illustrating the XRD profiles of PLA films during the hydrolytic degradation after three days exposure to 95% ethanol in various experiments.

In contrast, some sharp peaks began to appear after 3 days exposure to 50% and 95% ethanol (FIGS. 16D and 16E). The diffraction peaks observed in (FIGS. 16D and 16E) for ethanol solutions correspond to the formation of α-form crystals (orthorhombic unit cell with parameters a=1.06 nm, b=0.61 nm, and c=2.88 nm). In 50% ethanol, diffraction peaks at 14.8°, 16.8°. 19.1° and 22.4° were observed. In 95% ethanol, the diffraction peaks were in the same range as in 50% ethanol. They were 14.8°, 16.7°, 19.1° and 22.2°, corresponding to the 010, 110/200, 100/203 and 102/210 plane reflections, respectively. The appearance of crystals in PLA after 3 days exposure to ethanol solutions indicates that SIC took place in the early stages corresponding to primary crystallization (region I). At all times, the diffraction peaks were the same, meaning the same kind of crystals were formed during secondary crystallization (region II) and were present during the entire degradation of the amorphous regions (region III). It has been studied that the morphology behavior of amorphous PLA during hydrolysis in neutral conditions, and semicrystalline PLA in acid and alkaline environments where α-form crystals were mainly formed and remained during the degradation process.

Figure 17A:
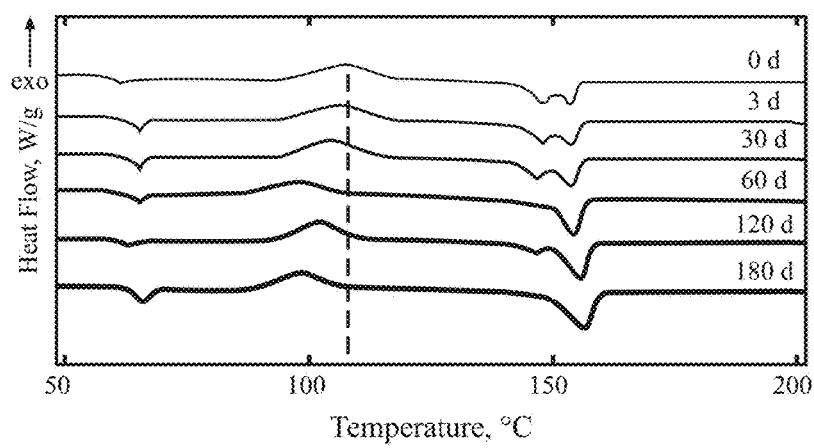
FIGS. 17A-17C are graphs illustrating the DSC thermograms as a function of time of PLA film during hydrolytic degradation in water (FIG. 17A), 50% ethanol (FIG. 17B), and 95% ethanol (FIG. 17C) at 40° C. in various experiments.
Figure 17B:
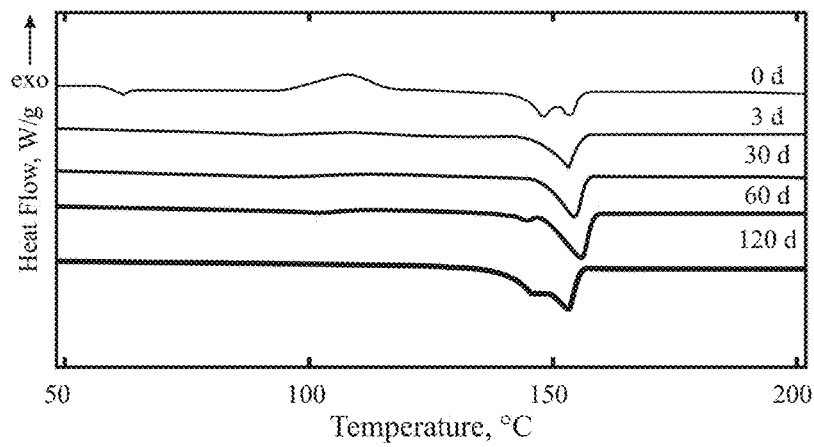
Figure 17C:
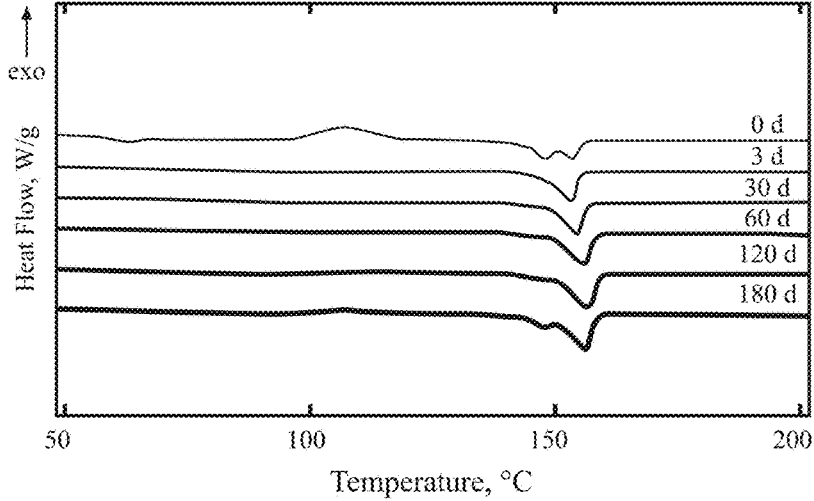

Crystallinity results can be correlated with DSC thermograms of PLA before and after being hydrolyzed by water-ethanol solutions for various times (FIGS. 17A-17C). Before exposure, amorphous PLA showed a cold-crystallization temperature peak ($T_{cc}$) due to the rearrangement of polymer chains inducing crystallization during the DSC heating process. When PLA was exposed to pure water (FIG. 17A), $T_{cc}$ shifted to a lower temperature. This can be attributed to chain scission and reduction in molecular weight of the PLA matrix, which facilitates nucleation and growth of PLA crystals, improving chain segment mobility.

Another explanation could be the production of locally ordered structures during hydrolysis, promoting the occurrence of cold crystallization at lower temperatures. The double melting peaks could be attributed to the formation of two different crystalline structures formed during the DSC heating process. Some crystals that could be formed during crystallization from melt are the α and β-forms that have approximately the same energy and therefore the possibility to coexist. The high $T_m$ corresponds to melting of the more stable structure, which is the α-crystal, while the low $T_m$ is ascribed to the less perfect crystal that is the β-form. The early peak could also be attributed to the devitrification of the rigid amorphous fraction (RAF).

For PLA exposed to ethanol solutions (FIGS. 17B and 17C), after the 3rd day, the samples did not show crystallization peaks, meaning that PLA had been crystallized in agreement with the XRD profiles, presenting α-form crystals (FIG. 16). The α-form crystals are reflected in thermograms displaying one melting peak over time.

Figure 18A:
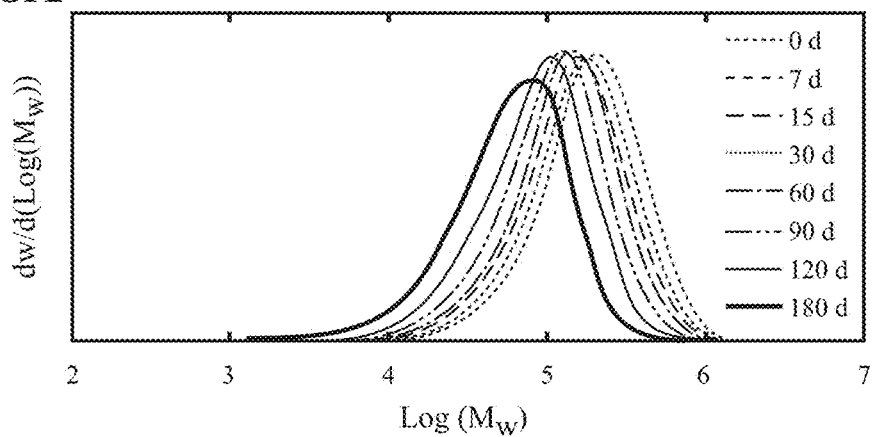
FIGS. 18A-18C are graphs illustrating the molecular weight distribution (MWD) as a function of time of PLA films during hydrolytic degradation when in contact with water (FIG. 18A), 50% ethanol (FIG. 18B), and 95% ethanol (FIG. 18C) at 40° C. in various experiments.
Figure 18B:
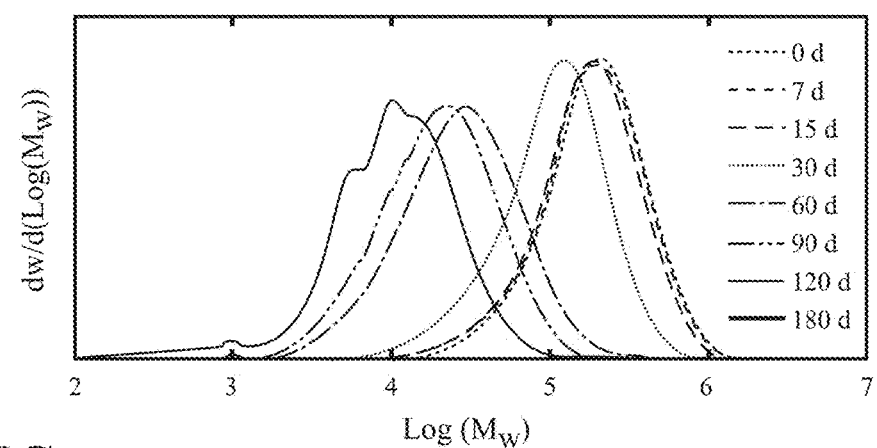
Figure 18C:
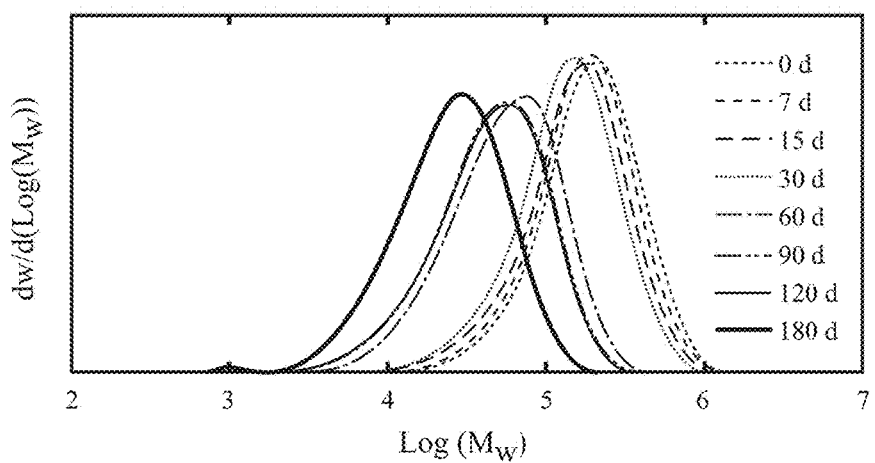

However, after 60 days of immersion, a small endothermal peak started to appear and became stronger over time. This phenomenon could be explained by hydrolysis process, which is reflected in the change of the molecular weight distribution (MWD) of PLA (FIGS. 18A-18C). After 60 days, the MWD of PLA became broader due to polymer chain scission, resulting in shorter polymer chains and the presence of LA oligomers with different $T_m$'s compared to α-form crystals originated by the SIC process (regions I and II, FIG. 15).

During hydrolysis of the amorphous regions of PLA, low molecular weight water-soluble oligomers and monomers are released. FIG. 2 shows the release of LA from PLA into water, 50% ethanol, and 95% ethanol at 40° C. During the first 40 days of exposure, the release of PLA monomers was higher when the polymer was in contact with 50% ethanol, followed by 95% ethanol and then by water (FIG. 2). After the second month of exposure, the release of LA increased exponentially for samples in contact with 50% ethanol. At 120 days, the concentration of LA in 50% ethanol was 700 pg/mL, meaning that approximately 30% of the PLA was hydrolyzed. Not long after that, the film disintegrated. Over the same period, the percentage of PLA hydrolyzed by water and 95% ethanol was 1.4 and 0.5%, respectively.

The highest release of LA in 50% ethanol concurs with the fastest reduction in $M_n$ (FIG. 4), since polymer chains in the amorphous regions are being hydrolyzed faster, as reflected by the increase in % $X_C$ in region III (FIG. 15).

A model that predicts LA release is proposed based on the process of chain scission into progressively lower molecular weights, followed by diffusion of LA-mers through the PLA matrix, followed by crossing the interface into the fluid, and finally dissolving into LA in the various water-ethanol solutions. The resulting concentration of LA in the solution is described by:

$$C_f = \frac{Q*A}{V_f}[(Rkt) - 1] \qquad \text{(Eq. 4)}$$

where $C_f$ is the concentration of LA in the solution, Q and R are constants, A is the disk surface area, $V_f$ is fluid volume, t is time, and k is the rate constant in Eq. (2). Fitting Eq. (4) to the experimental data gave Q=0.9 μg/cm² and R=2.232. The predicted LA release from PLA hydrolysis immersed in water, 50% and 95% ethanol are the curves in FIG. 2.

During LA release consider that the migration rate of molecules within the polymer matrix depends on several factors, including the size of the migrants, density and the $T_g$ of the polymer.

Therefore, changes in $T_g$ will affect the release of LA previously discussed since $T_g$ will determine the flexibility of polymer chains and the free volume within the matrix. When PLA was exposed to water ($T_g$=53° C.) (FIG. 14), the diffusion of LA and LA-mers took place in the glassy state because the experiments were conducted at 40° C. Below $T_g$ in the glassy state, the polymer is stiff and therefore less open to diffusion by LA molecules. For PLA immersed in ethanol solutions, diffusion of LA took place above $T_g$, in the rubbery state, where the polymer molecules are flexible and open to diffusion. The higher the ethanol content, the lower the $T_g$ and the higher the diffusion rates of LA and LA-mers.

Figure 19:
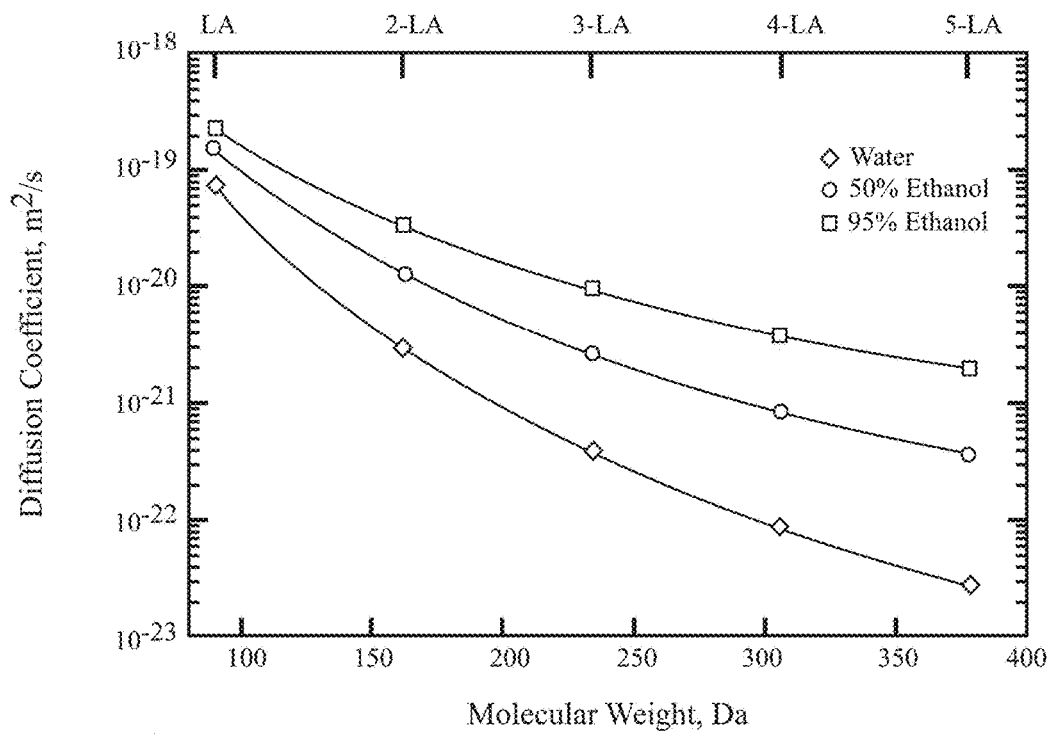
FIG. 19 is a graph illustrating the theoretical estimated diffusion coefficients of lactic acid (LA) and LA-mers in water, 50% ethanol, and 95% ethanol in various experiments.

The migrants from PLA are LA and LA-mers, which are degradation products from the hydrolysis of polymer chains. This disclosure carries out the quantification of alkali decomposition products based on the conversion of lactide and LA-mers to LA. A theoretical prediction for the rate of diffusion of oligomers up to 5 units was made based on the free volume theory as a function of the $T_g$ of the polymer during hydrolysis experiments (FIG. 19). Based on the predictions, the release of LA (90 g/mol) is faster when PLA is exposed to 95% ethanol.

Predicted values showed that the smaller the molecular weight of the oligomer, the faster the diffusion through PLA. Therefore, the LA quantified during release experiments can be identified as mostly LA released from the PLA matrix and not from the alkali hydrolysis of LA-mers released from PLA in the solution. It has been shown that the long-term migration of LA-mers in water at 40° C. show that until three months exposure to water, no LA-mers were detected. However, by six months, 3.46 µg/cm$^2$ of LA-mers up to 13 units were quantified. In the experiment, the initial presence of LA-mers in the PLA films were not detected by MALDI-TOF. Therefore, at the early stages the LA quantified during the experiments can be attributed to the hydrolytic degradation of PLA in contact with the water-ethanol solutions and released as mostly LA into solution.

The exposure of PLA disks to different water-ethanol solutions led to the hydrolytic degradation of the polymer with concurrent SIC. Hydrolysis was accelerated by the immersion of PLA in 50% ethanol, which showed a faster reduction in Mn than in 95% ethanol and pure water. Hydrolysis is related to the amount of water molecules available to start chain scission, so NMR techniques were applied to study water sorption in PLA. Higher sorption of D$_2$O was found when PLA was exposed to 50% ethanol, explaining the faster hydrolysis.

A new model was proposed to explain the rate of hydrolysis, accounting for the effect of PLA swelling due to ethanol sorption. The rate of degradation for 50% ethanol was 0.0230 gmol$^{-1}$ d$^{-1}$. This was the maximum rate of decay in Mn meaning that 50% concentration provides the optimal competitive balance between swelling and hydrolysis. During PLA hydrolysis the % $X_C$ increased, indicating that SIC occurred in PLA when exposed to 50% and 95% ethanol.

In the crystallization process of PLA, three different regions were identified. Regions I and II were due to SIC by ethanol. The Avrami equation was found to describe the crystallization process well. Region III was due to hydrolysis of the amorphous regions. XRD studies showed the formation of α-crystal during SIC. LA release was studied as an indication of hydrolysis of PLA. PLA immersed in 50% ethanol showed the highest release of LA, which is in accordance with the fastest decay in $M_n$ by hydrolysis. A model was proposed to predict LA release during hydrolysis when PLA is exposed to different ethanol-water solutions.

In addition, samples were retrieved at defined times during 6 months to assess $M_w$, $M_n$, water and ethanol sorption, thermal and physical properties, and LA release. The molecular weight of PLA was determined by the following process. At various times throughout the experiments, $M_w$ and $M_n$, were determined by weighing approximately 10 mg of film retrieved from the test cells and dissolved in THF (2 mg/mL).

A gel permeation chromatograph (GPC) (Waters 1515, Waters, Milford, Mass., USA) equipped with a refractive index detector (Waters 2414) and a series of three columns of HR Styragel® (HR4, HR3 and HR2) were used (each 7.8 mm×300 mm, Waters Styragel). An elution of THF at a flow rate of 1 mL/min was applied with a flow rate ramping time of 5 min and a total run time of 45 min. The temperature of the detector and column was 35° C. and the injection volume was 100 µL. A calibration curve was made from polystyrene standards-Shodex SM-105 (Waters, Milford, Mass.), which contained a molecular weight range of 1.37×10$^3$ to 2.48×10$^6$ Da. The Mark-Houwink constants for the correction were K=0.0164 mL/g and α=0.704 for PLA solutions in THF at 35° C. The measurements were conducted in triplicate.

The deconvolution of the molecular weight distribution (MWD) was carried out in Fityk using nonlinear least-squares curve fitting for a LogNormal function.

The process for water and ethanol sorption is as follows. Water and ethanol sorbed by PLA film were measured at 40° C. using migration cells. The water (H$_2$O) in the solvents (water, 50% ethanol, 95% ethanol) was replaced with D$_2$O to avoid contamination from environmental water and interference with measurements.

Ethanol sorbed was determined using the $^1$H NMR (proton nuclear magnetic resonance) technique and water sorbed using D-NMR (Deuterium NMR). Samples of film were taken periodically. For ethanol sorption, the samples were rinsed with D$_2$O and for water sorption with H$_2$O to remove the solvent from the surface. For ethanol sorption, samples were dissolved in CDCl$_3$ with DMF as the internal standard, and for water sorption, samples were dissolved in THF with CDCl$_3$ as the internal standard. For ethanol and D$_2$O sorption measurements, samples were analyzed using a Varian Inova 600 MHz superconducting NMR-Spectrometer equipped with a Nalorac 5 mm PFG switchable probe operating at 599.892 MHz and 92.069 MHz for $^1$H and $^2$H, respectively. Experiments were conducted in triplicate.

PLA samples, after hydrolysis in 50% ethanol at 80° C., were analyzed by 13 CNMR (carbon nuclear magnetic resonance) on a 500 MHz Varian DirectDrive 2 Spectrometer equipped with 5 mm PFG One NMR probe. The gHMBC (gradient heteronuclear multiple bond correlation) experiment was run on a Bruker Avance 900 MHz NMR spectrometer equipped with a 5 mm TCI triple-resonance cryoprobe operating at 898.76 and 226.02 MHz for 1H and 13 C, respectively. Samples were dissolved in CDCl3 and run at ambient temperature. 7,292 transients were collected for the carbon NMR with a 1.0 s recycle delay; data were zero-filled to 262144, and 0.5 Hz exponential multiplication was used. gHMBC data were collected with a 1.5 recycle delay, 96 scans per increment and 350 increments. Linear prediction and zero-filling were applied to the carbon dimension, and unshifted sine-bell squared windows were used in both dimensions.

A differential scanning calorimeter was used to determine the $T_g$, $T_m$, crystallization temperature ($T_c$) and % $X_C$ of the PLA samples. The samples where cooled from 25 to 5° C. and then run at a temperature range of 5–210° C., with a heating rate of 10° C./min using liquid nitrogen with a flow rate of 70 mL/min. The first heat scans of the samples are reported. The data obtained were analyzed using the Thermal Analysis Universal 2000 version 4.5A software. Percentage crystallinity was calculated using the heat of fusion of the 100% crystalline for PLA sample of 93.7 J/g.

The X-ray diffraction study (XRD) analyses were performed using a Bruker AXS D8 Advance X-ray diffractometer (Bruker Co., Billerica, Mass., USA) equipped with a Global Mirror filtered Cu Kα radiation source set at 40 kV and 100 mA. Samples were scanned in the 2θ range from 2° to 400 at a rate of 0.24°/min and an increment of 0.01°.

In dynamic mechanical analysis (DMA), to determine the $T_g$ of PLA, the loss factor (tan delta) was measured as a function of temperature when PLA samples were immersed between 4 and 7 days in the various ethanol-water solutions during testing. A TA RSA-G2 Solids Analyzer Immersion System (TA Instruments, New Castle, Del., USA) equipped with a tension geometry at a frequency of 1 Hz was used. The samples were cooled down from 25 to 10, −10, −10, −30, and −60° C. for 0, 25, 50, 75 and 95% ethanol volume and then heated to 60° C. at a heating constant rate of 5°

C./min using liquid nitrogen. The data obtained was analyzed using the TA Instruments TRIOS software.

Release of LA into the three different solvent systems (water, 50% ethanol and 95% ethanol) was determined using the migration cell at 40° C. Four replicates were performed for each of the solvent systems. LA quantification was carried out since lactide and oligomers are degradation products of PLA that are able to migrate and easily decompose to LA. Samples containing 0.5 mL of simulant were taken periodically and exposed to alkali hydrolysis. For ethanol solutions, the ethanol was evaporated using a Savant SCI 10 Speed Vac Concentrator System (Savant Instruments, Holbrook. N.Y. USA) and then reconstituted with 0.5 mL of water. Samples were then saponified with 50 µL of 0.2 M sodium hydroxide, followed by heating for 15 min in a water bath at 60° C. After cooling at room temperature, 50 µL of 0.2 M hydrochloric acid was added. LA was analyzed with an LC/MS/MS system with a triple quadrupole/linear ion trap (AB/Sciex QTRAP 3200. Framingham. Mass., USA). Separation was carried out on an Ascentis Express CI8, 2.7 µm, 100×2.1 mm reverse phase column (Sigma-Aldrich, St. Louis. Mo. USA.) with a flow rate of 0.2 mL/min. Solvents were A: 1% formic acid and B: methanol. Solvent programming was isocratic for 3 min with 1% B. then a linear gradient to 95% B up to 2 min. followed by the isocratic mode for 2 min. A linear gradient was then carried out in 0.01 min-1% B and held for 3 min in the isocratic mode. The oven temperature was 40° C.

Mass spectrometric analyses were performed in the negative-ion mode following the Ambient Pressure Chemical Ionization (APC1) method; the curtain gas was set to 20, gas-1 20 and gas-2 20, with a temperature of 650° C. The calibration curve was made from 0.25 to 15 µg/mL by treating the LA standard solutions in the same way as the samples and using malonic acid as the internal standard.

Figure 20:
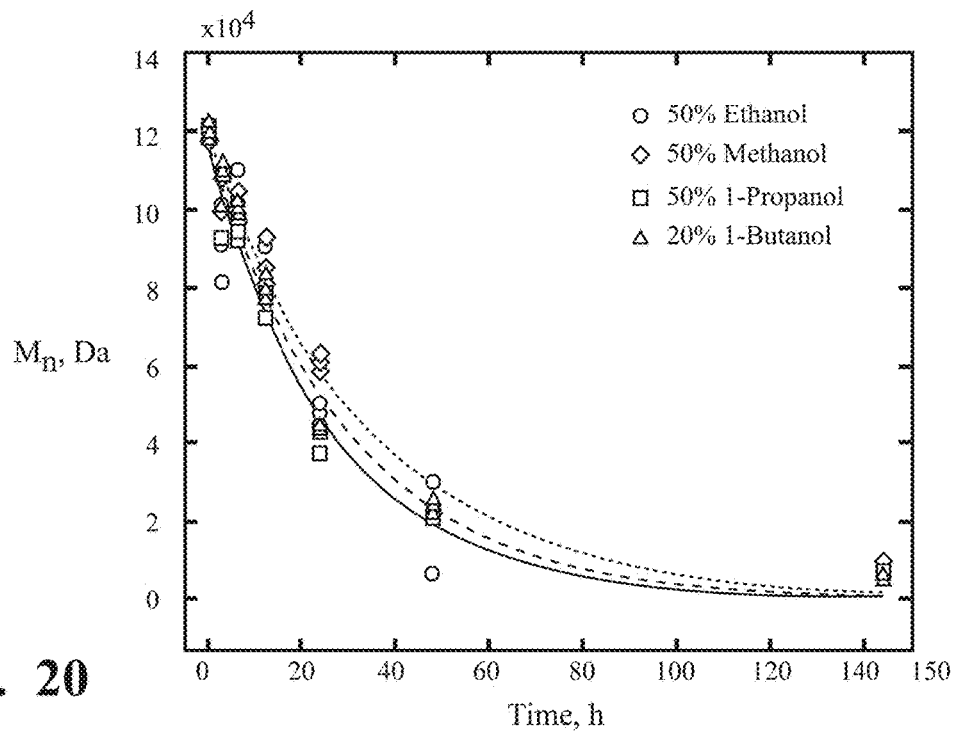
FIG. 20 is a graph illustrating the $M_n$ as a function of time during hydrolytic degradation of the PLA film while immersed in 50% ethanol, 50% methanol, 50% 1-propanol, and 20% 1-butanol at 70° C.
Figure 21A:
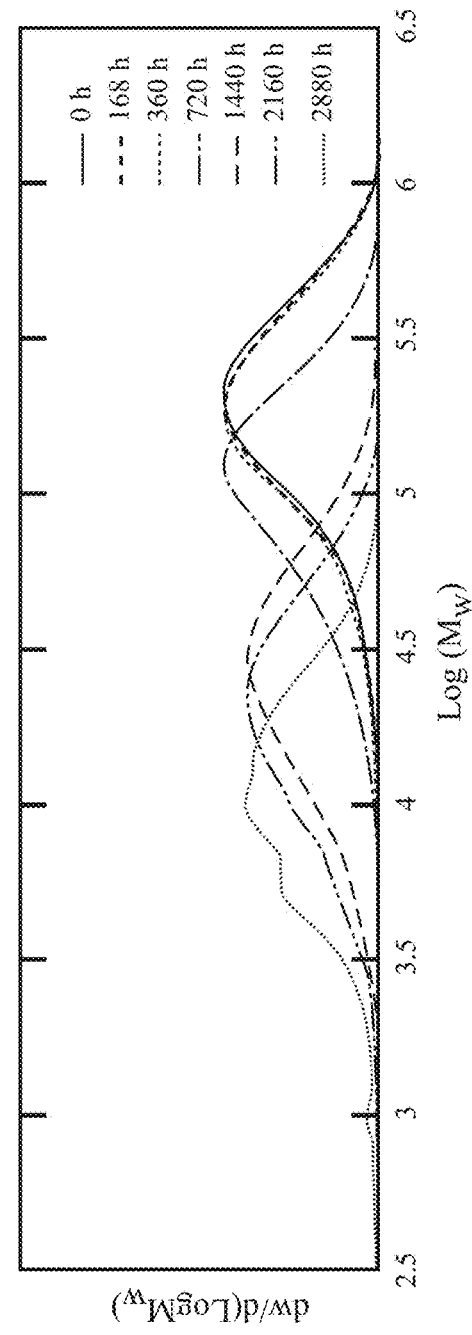
Figure 21B:
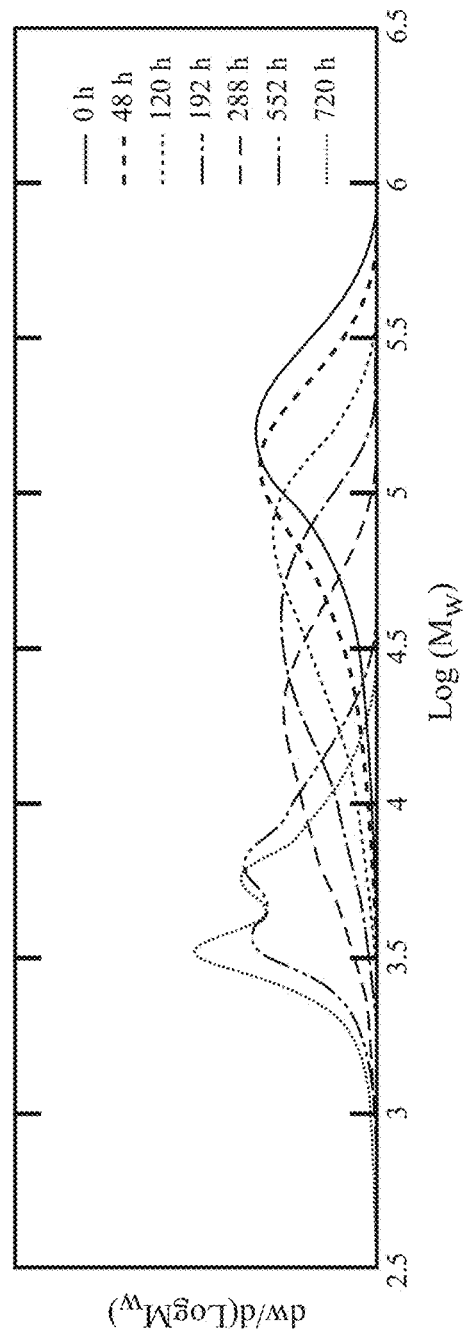
Figure 22A:
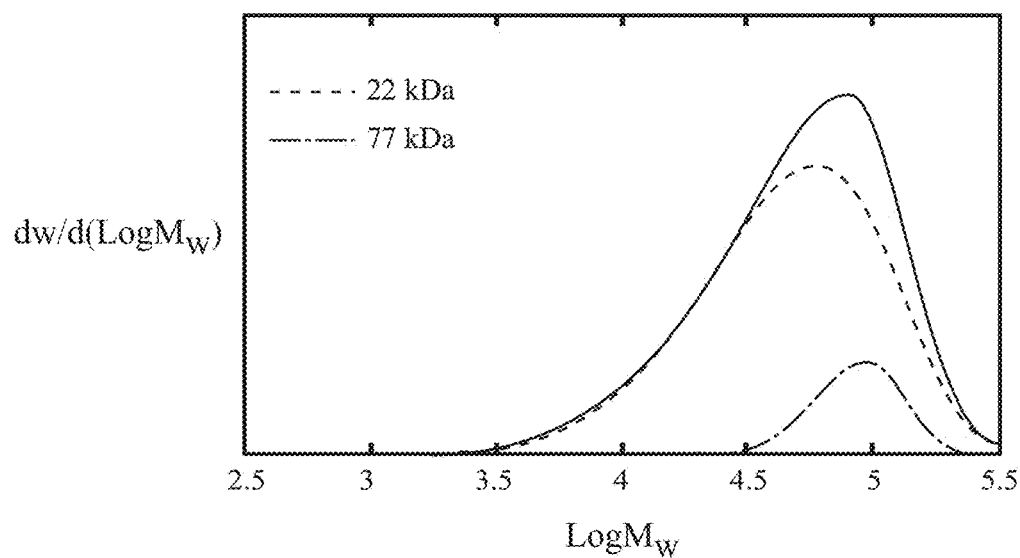
FIGS. 22A-22E are graphs illustrating the deconvolution of the MWD of PLA in 50% ethanol at 60° C. with hydrolysis taking place for 120 hours (FIG. 22A), 192 hours (FIG. 22B), 288 hours (FIG. 22C), 552 hours (FIG. 22D), and 720 hours (FIG. 22E).
Figure 22B:
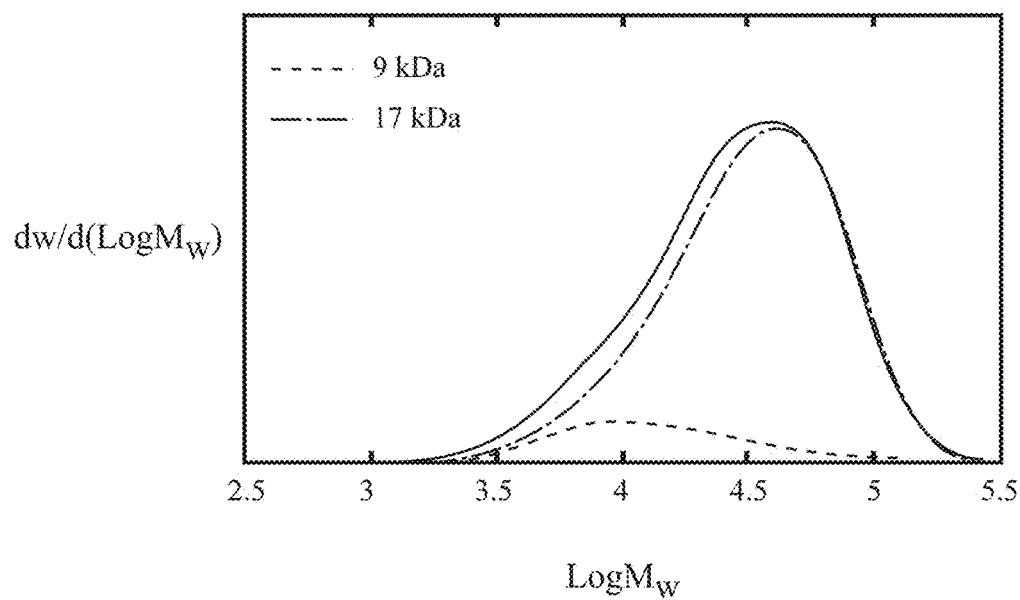
Figure 22C:
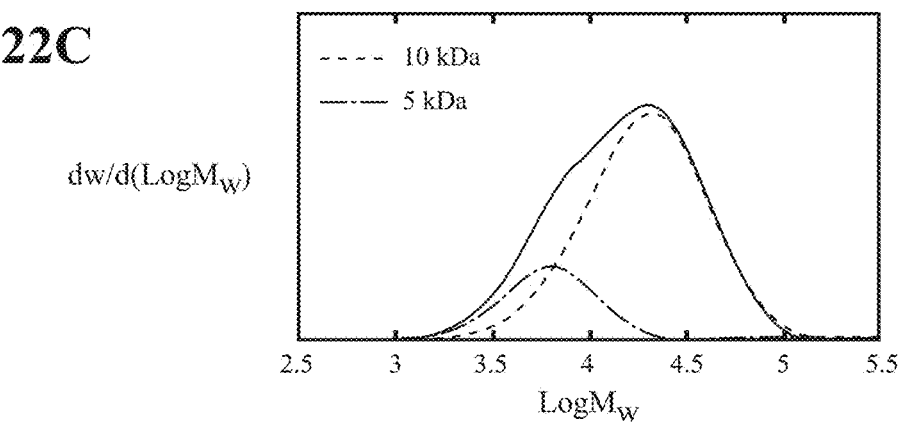
Figure 22D:
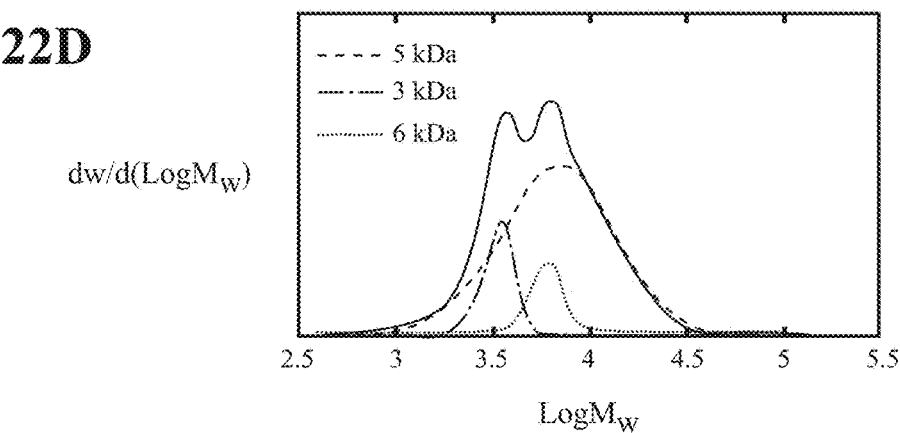
Figure 22E:
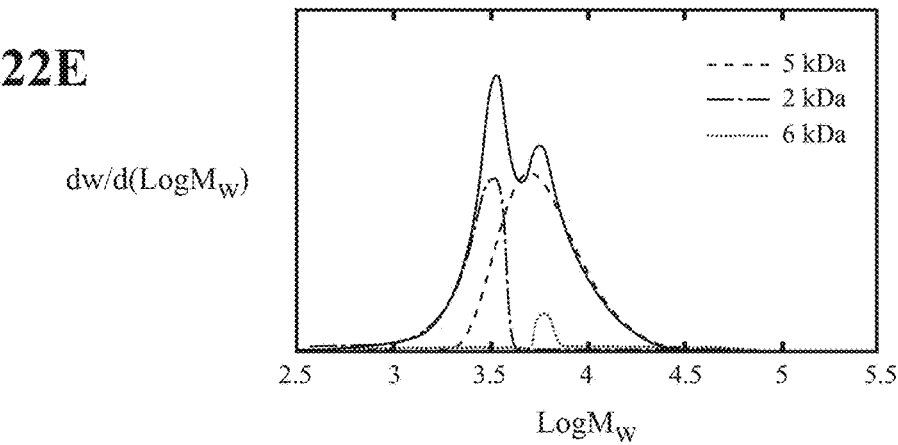

In one embodiment, the hydrolysis in different alcohol solutions was explored. The hydrolytic degradation of PLA in contact with water-ethanol solutions was evaluated. PLA showed faster hydrolytic degradation when it was in contact with 50% ethanol at 40° C. This is due to the competitive balance between the swelling effect of ethanol expanding the PLA network allowing the maximum sorption of water into the PLA matrix and the cleavage of the main chain of the polymer due to hydrolysis. To further explore the swelling effect of alcohol solutions, different alcohol solutions all at mostly 50% volume with water were used to evaluate the competitive balance between swelling and water sorption. FIG. 20 shows the change in $M_n$ with time when PLA was immersed in 50% ethanol, 50% methanol, 50% 1-propanol, and 20% 1-butanol at 70° C. A lower ratio of 1-butanol was selected due to the low miscibility between 1-butanol and water. Since the order of reaction for all the solvents was close to one, the approach to estimate the rate of reaction, k, was to assume as a first order behavior. The rate constants showed that the hydrolysis was slower when PLA was in contact with 50% methanol and no differences were found with 50% ethanol, 50% 1-propanol and 20% 1-butanol.

Since no differences were found among the alcohols except with methanol, which exhibited slower hydrolysis, 50% ethanol was used to assess the effect of temperature on the hydrolytic degradation of PLA and to calculate the Ea. Ethanol was also selected since it can be produced from renewable resources such as sugar cane or cornstarch, reducing the negative impact of using solvents derived from fossil resources for the recycling of PLA. Additionally, the boiling point of 50% ethanol solution is higher than 50% 1-propanol (92 and 88° C., respectively) and around the same as 20% 1-butanol (93° C.). Thus, the hydrolysis and recycling can be performed at higher temperatures without reaching the boiling point, which would create process complications. Lastly, ethanol is a more economical choice than that of 1-propanol and 1-butanol.

In another embodiment the hydrolytic degradation of PLA in 50% ethanol was determined. To study the effect of temperature on the hydrolytic degradation of PLA in 50% ethanol, PLA was exposed at different temperatures above the glass transition temperature (Tg) of the polymer immersed in 50% ethanol (Tg=36° C. [15]): 40, 60, 70 and 80° C. FIGS. 21A-21D show the MWD of PLA when it was exposed to hydrolysis in 50% ethanol. When the hydrolysis of PLA is via surface erosion the main peak of the MWD remains at the initial position with a reduced peak area. However, when PLA was exposed to hydrolysis at all temperatures, the MWD shifted away from its original position at time 0 h towards lower $M_n$. In addition, the same behavior was found indicating that degradation of PLA was preferentially carried out by chain scission in the bulk. At all temperatures, while the hydrolysis was progressing, the MWD peaks broaden and fragments of PLA chains were formed due to chain scission. Also, the MWD peaks at some point of the process changed from a monomodal distribution to double, triple or n-peaks distributions as seen in the MWD, indicating the formation of PLA oligomers. In other embodiments, the hydrolysis of different blends of crystalline and amorphous PLA were determined and it was found that the formation of another peak is mostly due to the crystalline regions of PLA in the blends. Also, in a comparative study on the hydrolytic degradation of PLA in the solid and in the melt found the formation of an additional peak during hydrolysis due to the degradation of the amorphous regions and presence of crystalline residues in the polymer matrix. So, the formation of additional peaks in the MWD during PLA degradation in 50% ethanol could be due to the crystalline residues from the hydrolysis process.

The crystallinity of PLA film immersed in 50% ethanol at 40° C. was analyzed during hydrolysis. The degree of crystallinity of the film increased from around 3%-25% after 168 h of immersion, and then between 360 h and 2880 h the crystallinity further increased to 50%. At the point that the MWD started to show more than one peak below 60 kDa, the crystallinity of the film was 40% corresponding to the region in which the crystallinity increases due to the hydrolysis of the amorphous regions of the PLA. This behavior could reflect complex kinetics where the ester bonds of PLA oligomer chain may have different susceptibility to cleavage. That means selective scission occurs where the degradation is not homogeneous and the accumulation of different low molecular weight fractions is more evident at prolonged hydrolysis time. In terms of chemical recycling of PLA, the crystalline residues could prolong the reaction period required for obtaining a high yield of LA.

In another embodiment, a deconvolution study of the MWD was performed to understand the reaction kinetics to study the effect of temperature on the hydrolytic degradation of PLA in 50% ethanol. Different deconvolution functions have been used such as Gaussian and Lorentzian functions. However, it has been shown that these functions are not appropriate since the curves for solid-state reactions are asymmetrical, whereas LogNormal can properly fit asymmetric functions. The LogNormal function was used to perform the deconvolution of the peaks followed by the kinetics analysis of the separated peaks to calculate the rate constants. The deconvolution of the peaks was carried out when skewness of the distribution was observed and when more than one peak was detected in the MWD. This occurred when Mn was below 60 kDa where the MWD distribution deviated from monomodal at all temperatures. FIGS. 22A-22E show an example of the deconvolution of the last 5 curves of the hydrolytic degradation of PLA in 50% ethanol at 80° C. from (FIGS. 21A-21D). Different MWD can be observed from 120 h to 720 h of hydrolysis. The longer the exposure of PLA in solution, the more different lengths of polymer chains are formed. This means that while the PLA is exposed to 50% ethanol, selective chain scission occurs during the hydrolysis reactions.

The hydrolytic degradation of PLA leads to random cleavage of the ester bonds where longer chains of the polymer are more susceptible to hydrolysis than the shorter chains. The hydrolysis products of PLA contain fragments of water-soluble products like oligomers and LA fragments. To understand the hydrolysis of PLA, the proposed $M_n$ from the deconvoluted portions of the original MWD were plotted as a function of time (FIGS. 23A-23D). The $M_n$ reduced to about 50 kDa when PLA was immersed for 720, 48, 24 and 12 h at 40, 60, 70, 80° C., respectively, which is marked with a crossed dotted line (-•-) in FIGS. 23A-23D. Before that time, the MWDs were monomodal. After this point, increased skewness of the distributions and more than one peak were observed where the individual Mn obtained from the deconvolution process were plotted.

Figure 23A:
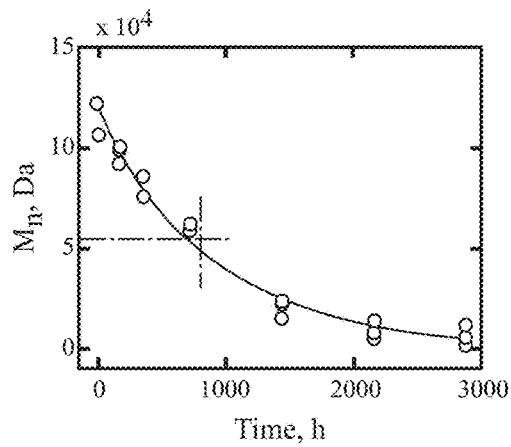
FIGS. 23A-23D are graphs illustrating the $M_n$ as a function of time during hydrolytic degradation of PLA films immersed in 50% ethanol at 40° C.
Figure 23B:
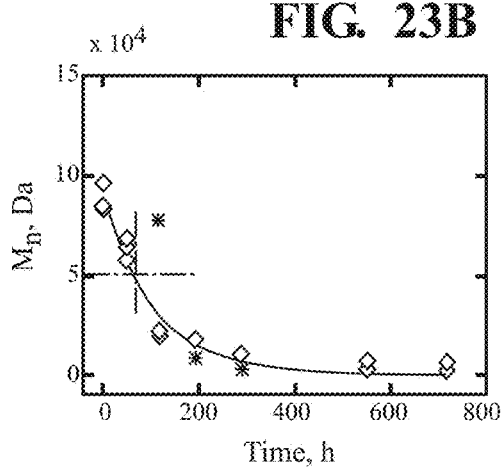
Figure 23C:
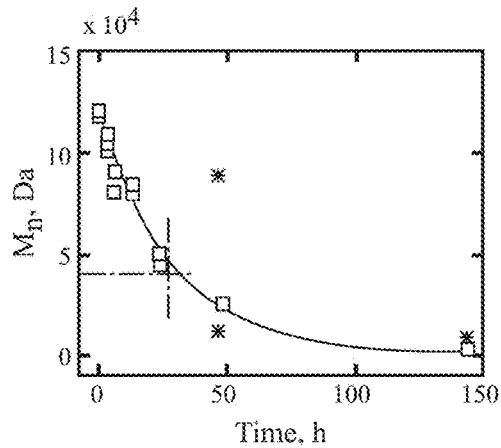
Figure 23D:
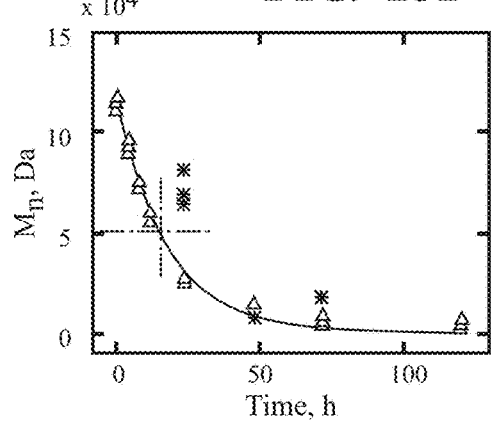

To further understand PLA degradation, recombination reactions, which may result in crosslinking were considered. Recombination reactions of PLA have been seen when the polymer has been exposed to thermal degradation or degradation by composting. They can also happen when cyclic oligomers recombine with linear molecules by ring opening reactions favoring the formation of longer chains. In another embodiment, cross linking was discarded as a side reaction after NMR experiments were carried out. In particular, gHMBC and 13CNMR were run on PLA exposed to 50% ethanol at 80° C. to probe for any new carbon resonances that may have formed that correspond to cross-linking (e.g., carbon resonances around 100 ppm due to orthoesters). Aside from peaks attributable to PLA, oligomers and lactide, there was no evidence of crosslinking. FIGS. 23B, 23C, and 23D showed a reduction in $M_n$ until 50 kDa with a subsequent increase in $M_n$ at 60, 70 and 80° C., which could be attributed to recombination reactions.

After the process of separating the individual data of the $M_n$ obtained by peak deconvolution, the kinetic analysis of selected $M_n$ is the most prevalent reaction was carried out for each temperature. FIG. 24 shows the order of reaction of the selected $M_n$ during hydrolysis of PLA immersed in 50% ethanol at 40, 60, 70 and 80° C. The order of reaction for each temperature was close to a first order kinetic reaction. Therefore, the rate constants were calculated using Eq. (37) below. It is well known that hydrolytic degradation depends on the temperature, so the rate of hydrolysis of PLA increases with temperature. When the temperature increases, the time in which PLA was degraded to ~5 k Da decreased from 4 months at 40° C. to about 5 days at 80° C. According to the scale sensitivity coefficient (SSC), which can be used to approximate the optimal time to accurately estimate the hydrolysis reaction rate, the hydrolytic degradation experiments should be run for 1000, 100, 33 and 16 h at 40, 60, 70 and 80° C., respectively. Therefore, the data for the decrease of $M_n$ before about 50 kDa, where the MWD does not exhibit skewness or multiple peaks, which is marked with a crossed dotted line (-•-) in FIGS. 23A-23D, should be sufficient to estimate the kinetic parameters for a first order reaction. At 60° C., more initial experimental points should be taken to further improve the estimates since only two points were taken before 100 h.

In various embodiments, the effect of temperature on the hydrolytic degradation of PLA in 50% ethanol was determined. To evaluate the effect of temperature on the hydrolytic degradation of PLA for chemical recycling, the activation energy as stated by the Arrhenius equation must be estimated. Commonly, the effect of temperature on the hydrolysis of PLA is estimated by linearizing the Arrhenius equation Eq. (38) set forth below by plotting the natural logarithm ln(k) from the equation as a function of the reciprocal temperature to avoid fitting a non-linear equation. However, when the Arrhenius equation is used for parameter estimation, high correlation is found when Ea and $k_o$ are simultaneously estimated, resulting in high relative error. FIG. 25 shows the correlation matrix for the hydrolytic degradation of PLA in 50% ethanol using the Arrhenius equation as expressed in Eq. (38). A large correlation of the Ea and $k_o$ for the hydrolysis reaction in 50% ethanol was found, with relative error for Ea and $k_o$ of about 15% and 328%, respectively.

During hydrolytic degradation of PLA, the number of carboxylic acid chain ends increases, making the hydrolysis a self-catalyzed reaction due to the accumulation of the acidic polymer fragments in the specimens. So, the pH decreases over time, for example from pH=8.7 to pH=4.6 at 40° C. after 2800 h. Besides temperature, the hydrolysis mechanism of PLA may depend on the pH of the media due to the different susceptibility of the ester groups in lactic acid oligomers. It is important to study the influence of the pH on the hydrolysis rate constant of PLA. A parameter estimation approach was used to estimate the parameters of Eqs. (35) and (36).

Figure 26:
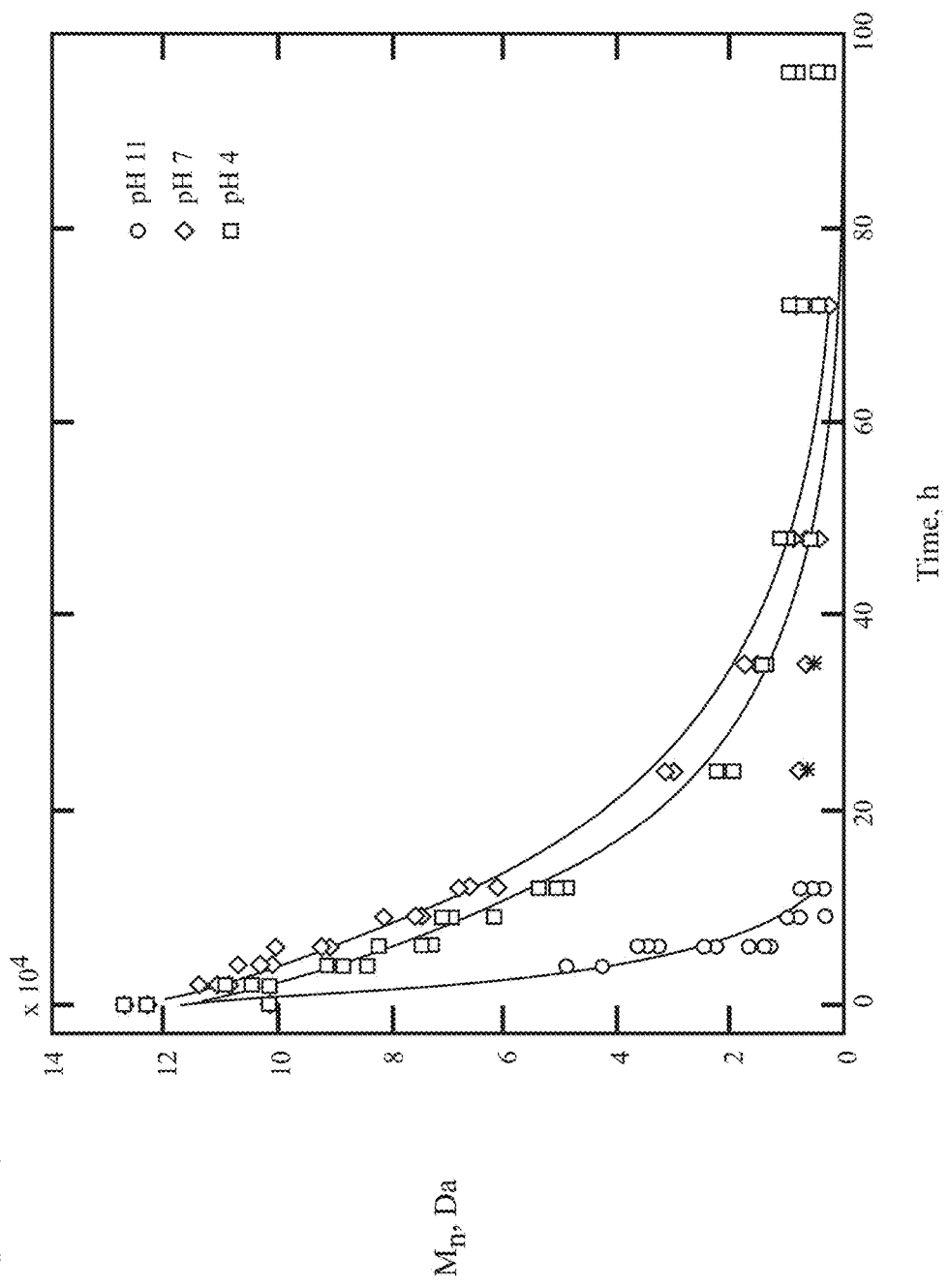
FIG. 26 is a graph illustrating $M_n$ as a function of time during hydrolytic degradation of PLA film immersed in 50% ethanol at 80° C. with different pH values.
Figure 30A:
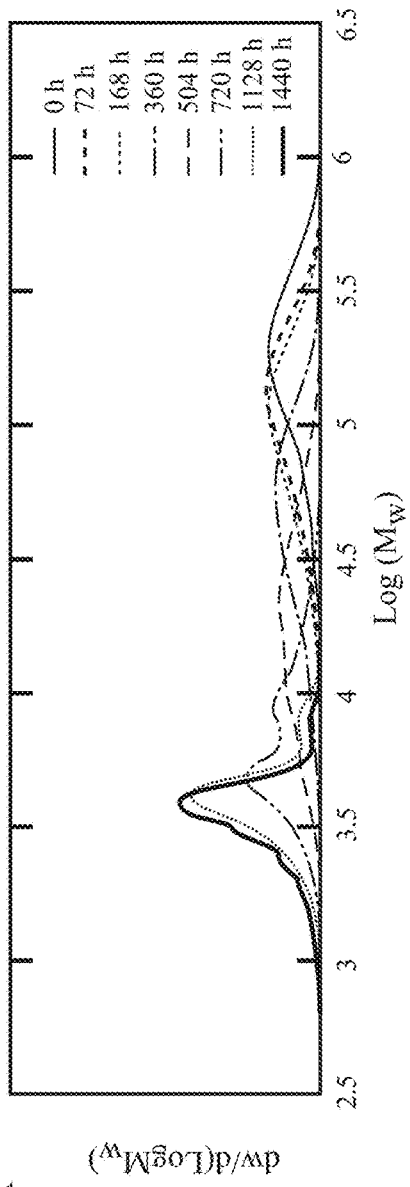
FIGS. 30A-30D are graphs illustrating the MWD of PLA films during hydrolytic degradation when in contact with water at 60° C.
Figure 30B:
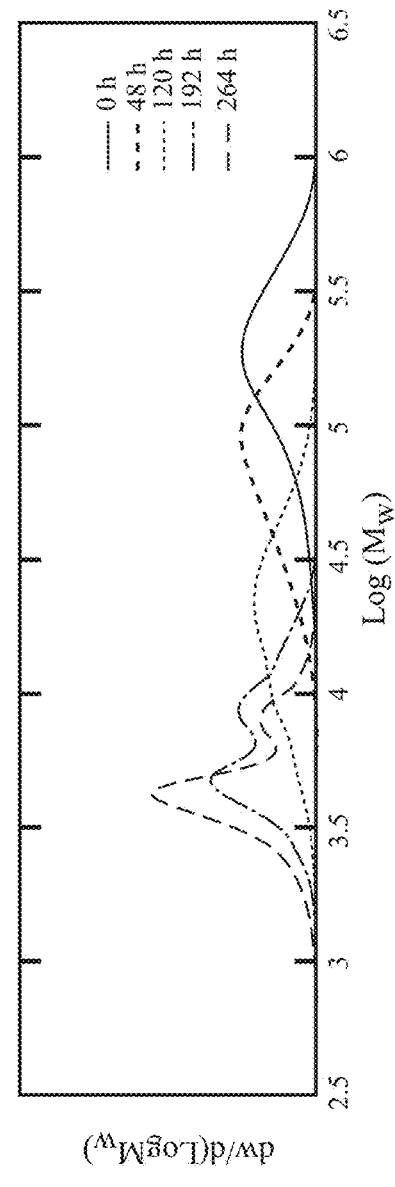
Figure 30C:
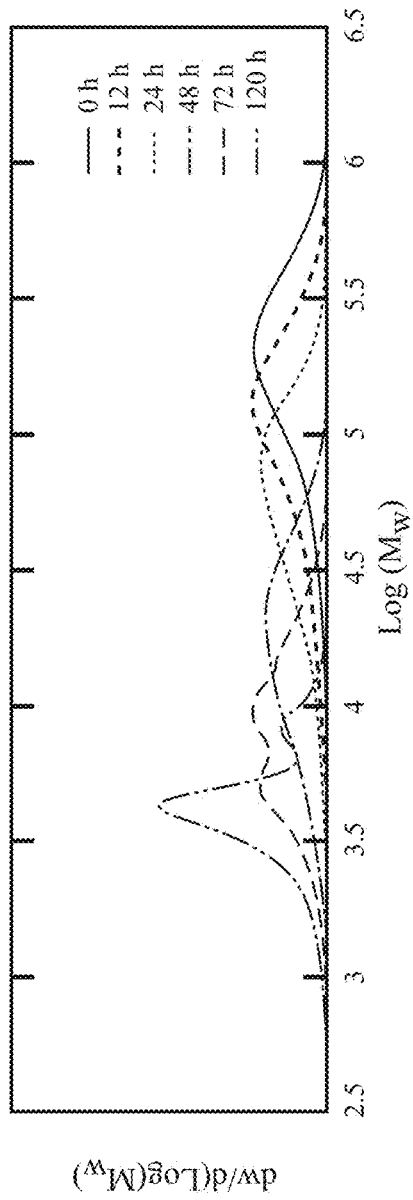
Figure 30D:
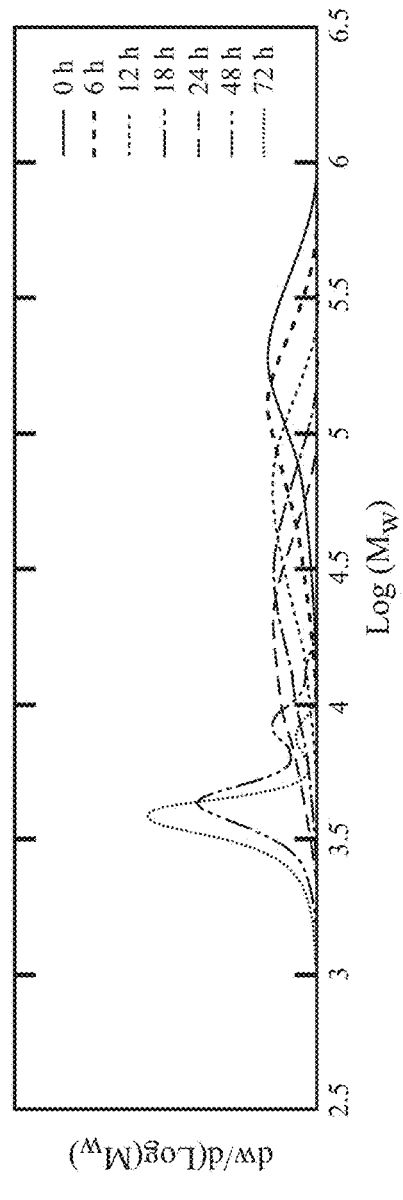

When PLA was immersed in 50% ethanol at 80° C. and different pH the MWD shifted towards lower molecular weight as hydrolysis proceeded. As in the hydrolysis of PLA in 50% ethanol without controlling the pH of the solution, the MWD at the latest stages of the degradation did not show a monomodal distribution. Therefore, for the analysis of the kinetics the same deconvolution procedure of the MWD was performed as in FIGS. 22A-22E, and then the analysis of the $M_n$ selecting the more likely side reactions to happen as in FIGS. 23A-23D. FIG. 26 shows the change in $M_n$ of PLA during hydrolytic degradation at different pH values after the deconvolution of the MWD. Illustrated in FIG. 27, the order of reaction was close to one for the hydrolysis of PLA at pH 4, 7 and 11. Therefore, Eq. (37) was applied to estimate the rate of hydrolysis. When the pH of the media was basic (pH 11) the hydrolysis was faster than at acid (pH 4) and neutral (pH 7) conditions (FIG. 27). When PLA is exposed to basic conditions, the carbonyl carbon atoms of the polymer are susceptible to attack by the hydroxide ions and hydrolytic degradation and molecular weight reduction are more significant than in acid solutions.

After the analysis of the hydrolytic degradation of PLA in 50% ethanol at different pH at 80° C., where the rate increased exponentially with pH, thereby supporting the proposed equation, the estimation of β using Eq. (38) was carried out to be able to estimate Ea from Eq. (37). For the estimation of β, it was necessary to find the optimum $pH_{ref}$ to have low correlation between parameters. Since there is no information on the $pH_{ref}$, the pH average was initially used ($pH_{ref}$=7.33). A final $pH_{ref}$=7.697 was determined. The optimum $pH_{ref}$ was used for the final estimation of the parameters presented in FIG. 28 where 3 was equal to 0.2153. The values of $\beta=0.2153$ and $pH_{ref}=7.697$ were used for the estimation of Ea as a function of pH and temperature (Eq. (37)).

To estimate the Ea as a function of pH using Eq. (37), it was necessary to find the optimum $T_{ref}$ to have low relative errors in the final estimation. The methodology to estimate the $T_{ref}$ is shown in the supporting information giving a $T_{ref}$ of 56.538° C. with a correlation coefficient of $4.1080\times10^{-5}$ between Ea and $k_{ref}$ and a relative error of 1.63 and 3.31%, respectively. FIG. 29 shows the final estimated parameters for Eq. (37) for the hydrolysis of PLA in 50% ethanol.

In one embodiment, the hydrolytic degradation of PLA depends on the pH of the media. However, it is important to study whether the pH correction previously applied would affect the Ea of hydrolysis. Eq. (36) was applied to estimate Ea without considering the change of pH during hydrolysis. For the non-linear regression estimation, the optimum $T_{ref}$ 57.688° C. with the lowest correlation was used for the final estimation of the parameters as presented in the supporting information giving a correlation coefficient of $1.2976\times10^5$ between Ea and $k_{ref}$ and a relative error of 1.79 and 3.52%, respectively. The activation energy of the hydrolytic degradation of PLA in 50% ethanol without considering the change of pH during hydrolysis was $9.341\times10^4$ J/mol (FIG. 29). After the reparameterization of the Arrhenius equation the Ea was estimated as $9.589\times10^4$ J/mol when dependence on pH was included. The difference between these values of Ea was not statistically significant ($p>0.05$).

In another embodiment, the hydrolytic degradation of PLA in water was determined. The understanding of how 50% ethanol solution contributes to the hydrolytic degradation of PLA for chemical recycling purposes and the effect of temperature on the hydrolysis of PLA was studied in water without ethanol. PLA films were immersed in water at different temperatures above the Tg: 60, 70, 80 and 90° C. FIGS. 30A-30D shows the MWD of PLA during hydrolysis at these different temperatures. As in the hydrolysis of PLA in contact with 50% ethanol (FIGS. 21A-21D), the MWD shifted to lower molecular weight as the hydrolysis reactions took place. At all degradation temperatures, the broadness of the MWD increased and at the last stages several peaks appeared in the distributions. Even though the MWD shifted to lower molecular weight as hydrolysis proceeded for PLA in water and in 50% ethanol, the evolution of the peaks was different. For example, during hydrolysis at 70° C. (FIG. 30B), a peak was observed after 192 h of immersion in water ($M_n \approx 4$ kDa). Then, the peak shifted to lower molecular weight ($M_n \approx 3.5$ kDa) and the height of the peak increased after 264 h being the more predominant peak. However, for 50% ethanol (FIGS. 21A-21D) this peak was not as predominant as in water, which may be attributed to the difference in the chain scission selectivity during PLA hydrolysis process due to the swelling effect of the ethanol molecules. The analysis of the effect on temperature on the hydrolysis of PLA in water was performed following the same procedure of deconvolution as in the hydrolysis of PLA in 50% ethanol to identify the side reactions and estimate the constant rates of the hydrolysis of PLA in water.

Figure 32:
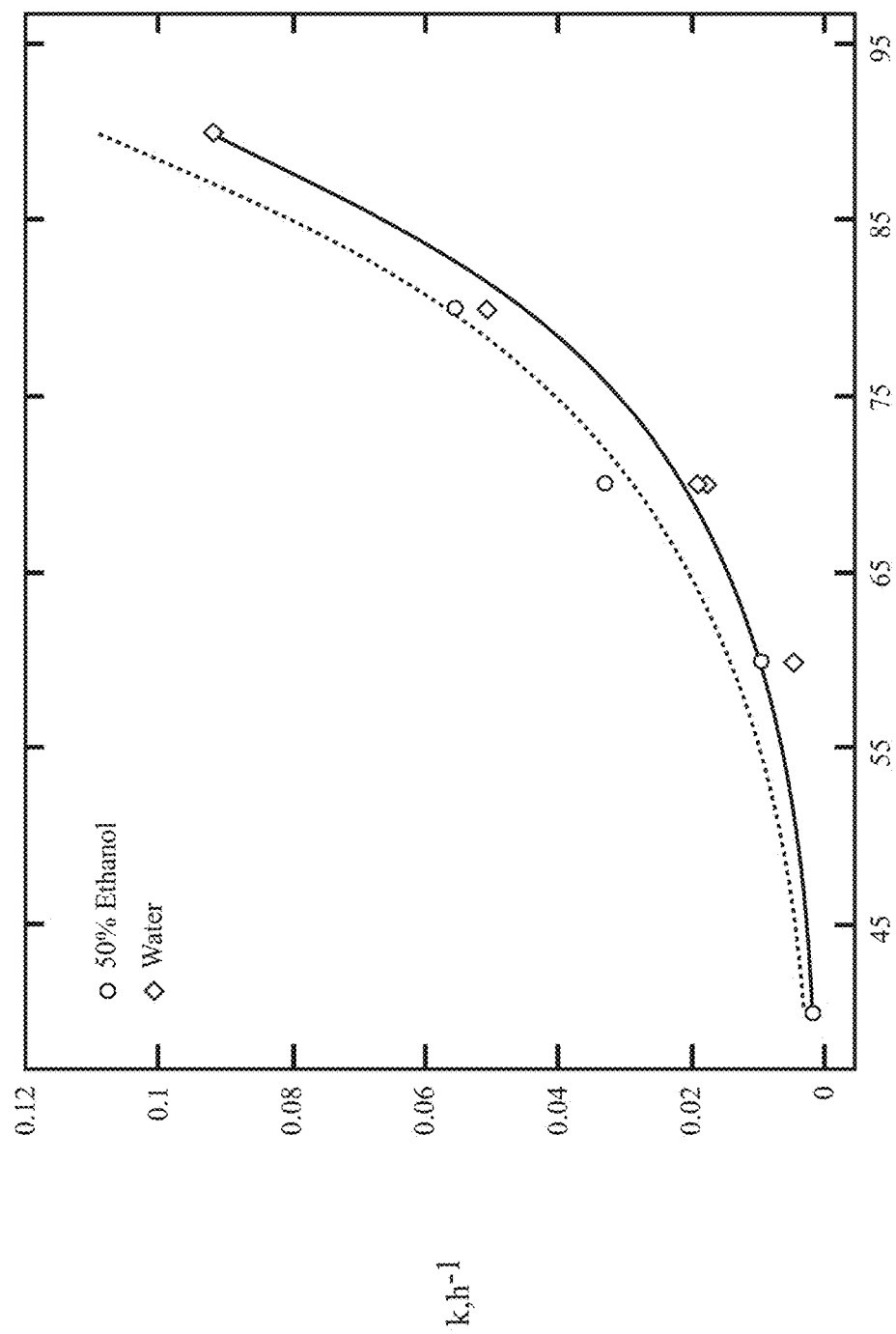
FIG. 32 is a graph illustrating the rate constants (k) of the hydrolytic degradation of PLA in 50% ethanol solution and water versus temperature.

In one embodiment, shown in FIGS. 31A-31D, the change in $M_n$ of PLA over time is shown when it was immersed in water at 60, 70, 80 and 90° C. After the deconvolution of the MWD, the more likely side reactions were selected following the same process as in 50% ethanol. The order of reaction of the selected $M_n$ for each temperature was close to 1 (FIG. 24). Therefore, the rate constants were estimated using the first order reaction (Eq. (32) below) as shown in FIG. 24. The higher the temperature the faster the hydrolysis. The hydrolytic degradation of PLA was faster when it was in contact with 50% ethanol than in water at 60 and 70° C. ($p<0.05$); however, no statistical difference was detected on the rate of hydrolysis between 50% ethanol and water when PLA was exposed at 80° C. ($p>0.05$). This can be rationalized by the increased movement of the PLA chains at 80° C. resulting in the same rate of penetration of water molecules as the swelling of the matrix that occurs when PLA is exposed to 50% ethanol solution. FIG. 32 shows the rate constants of hydrolysis in 50% ethanol and water at the various temperatures of the experiments performed. The trend lines indicate that the higher the temperatures of the hydrolytic degradation in 50% ethanol and in water the faster the hydrolysis, increasing exponentially.

In one embodiment, the effect of the temperature on the hydrolytic degradation of PLA in contact with water was determined. The activation energy was estimated using the reparameterization of the Arrhenius equation (Eq. (36) below) without considering the change of pH during hydrolysis since the pH did not have an effect on the Ea of PLA when it was hydrolyzed by a 50% ethanol solution. So, it was assumed that it would not have an effect on the Ea in water. The procedure for the estimation was the same as in 50% ethanol. For the final estimation of the parameters, the optimal $T_{ref}$ of 75.931° C. was used since it gave a correlation coefficient of $1.5516\times10^{-5}$ between Ea and $k_{ref}$ and a relative error of 2.48 and 2.20%, respectively, which are acceptable and very low. The final estimation of the Ea of the hydrolytic degradation of PLA in water was $10.143\times10^4$ J/mol (FIG. 29).

Even though the values of the Ea for the hydrolytic degradation of PLA in water and in 50% ethanol were different these values are within the range of values (from 4 to $10\times10^4$ J/mol) when PLA was exposed to different environments. These environments include 100% relative humidity (40-80° C.), steam high pressure (100-130° C.), water high pressure (180-350° C.; 140-180° C.), pH 7 buffer solution (37-70° C.; 50-75° C.), basic media of pH 10 (50-70° C.) and acidic media of pH 2 (40-120° C.). In another embodiment, some of the studies were performed using a range of temperatures below and above the Tg that could affect the final estimation. However, the Tg was not reported in solution, but of the initial PLA samples.

In yet another embodiment, the present invention provides an alternative method for chemical recycling of PLA. For that, it is important to consider the LA-oligomers yield during the hydrolysis reactions. Ea values have been reported within the range of this study in aqueous phase but at higher temperatures (120-250° C.), obtaining high yields (~95%) of LA when hydrolysis was close to the Tm. When PLA is hydrolyzed in the solid state, crystalline residues, as discussed for FIGS. 21A-21D, could prolong the reaction period required to obtain high yields of LA. However, when PLA containing the crystalline residues is hydrolyzed in the solid state in water, the LA yield was comparable with the hydrolysis in the molten state without any crystalline residues where the time to get 95% LA yield at 120° C. was 72 h and at 180° C. was 2 h. In this study according to the rate constant estimated in FIG. 24, the time needed for 95% yield of LA at 80° C. in 50% ethanol should be 128 h. If the temperature of hydrolysis increased to 91° C., below the boiling point of the 50% ethanol solution, the time would be reduced. Using the values estimated in FIG. 24, the rate of hydrolysis at 91° C. and the time needed to get the 95% LA yield can be estimated using Eq. (36) giving 0.1698 h−1 and 41 h, respectively. The time of 41 h is comparable with the values obtained in water at 120° C. In one embodiment, the time needed to get 95% yield of LA-oligomers of 10 units in 50% ethanol at 91° C. would be around 29 h. Thus, a feasible method to achieve low $M_n$ PLA with green solvents at moderate temperatures using low energy and in a reasonable amount of time is discussed.

Future studies should be conducted to estimate the yield of LA-oligomers when PLA is hydrolyzed in 50% ethanol to re-polymerize PLA. It is important to study the crystallization behavior of PLA at high temperatures when PLA is immersed in 50% ethanol and how it will affect the yield of LA oligomers for the chemical recycling of PLA and establish the separation process and purification of LA from the water-ethanol solution. It is expected that small increases in temperature can be translated into greater gain of LA-oligomers for recycling PLA.

The hydrolytic degradation of PLA by water-ethanol solutions for chemical recycling was studied. The hydrolysis of PLA at moderate temperatures above the Tg was carried out in 50% ethanol solution and in water to study the effect of temperature. The analysis of the MWD indicated that the hydrolysis in 50% ethanol and water was preferentially carried out by bulk erosion showing a multi-modal distribution at the latter stages of the hydrolysis. The deconvolution of MWD indicated that multiple reaction pathways followed first order kinetics. The Ea for the hydrolysis of PLA in water was around 9% higher than in 50% ethanol at moderate temperatures: $10.143 \times 10^4$ and $9.341 \times 10^4$ J/mol, respectively. These values were estimated after the reparameterization of the Arrhenius equation to obtain near zero correlation between parameters and therefore producing a better estimation. Also, the Ea for the hydrolytic degradation of PLA in 50% ethanol was estimated taking in consideration the change of pH, however; no differences were found in the estimations. In one embodiment, an alternative method of using 50% ethanol to hydrolyze PLA at moderate temperatures for PLA chemical recycling was performed.

NMR Analysis

Figure 33:
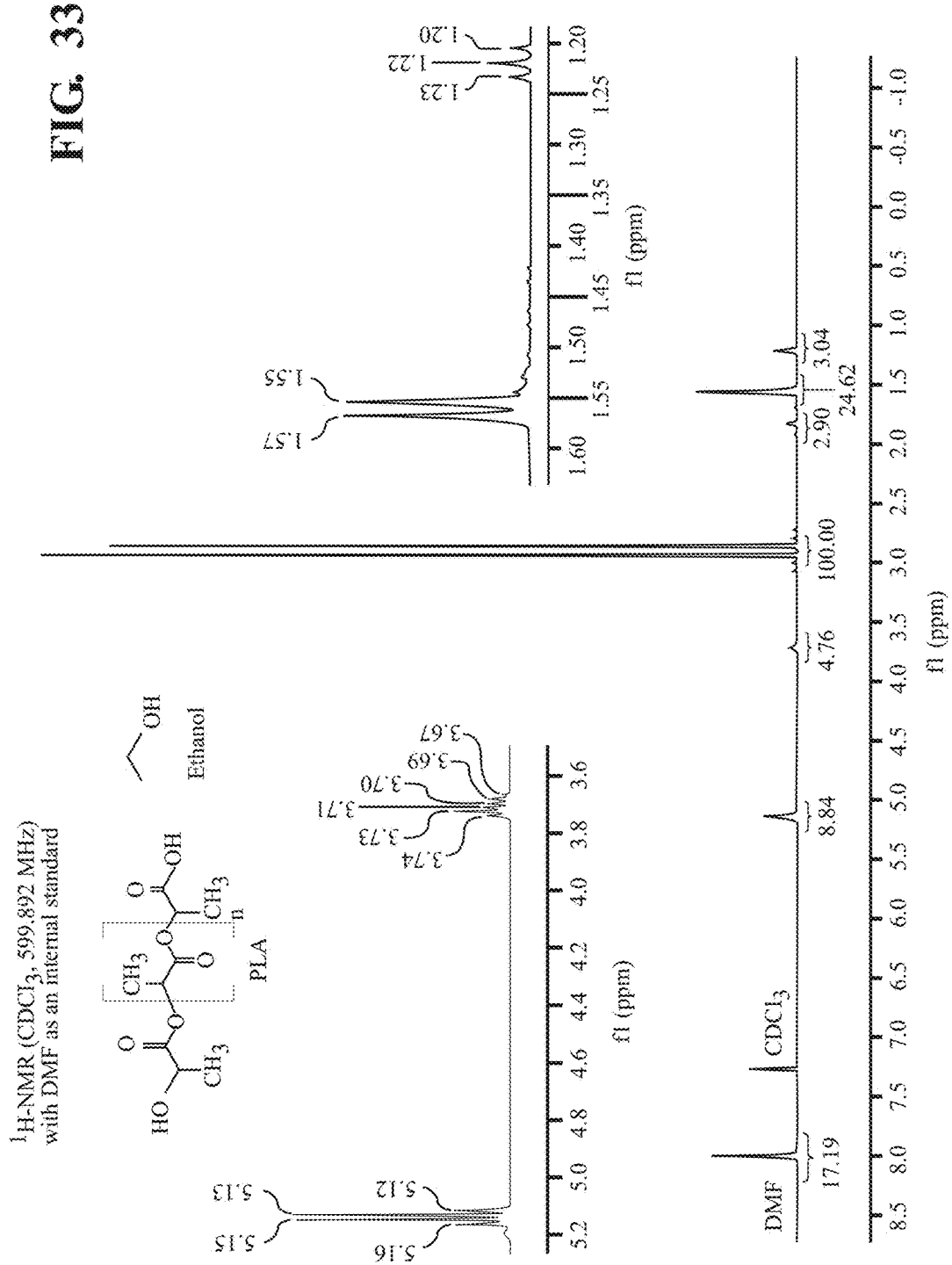
FIG. 33 is an $^1$H-NMR spectrum of PLA with ethanol in various experiments.

The $^1$H-NMR spectrum of PLA film with ethanol is shown in FIG. 33. The protons of ethanol $CH_3$ and $CH_2$ groups are located at 1.22 and 3.70 ppm, respectively. The $CH_2$ protons have some overlap with residual THF (3.72 ppm). These chemical shift values, however, demonstrate that ethanol does not overlap with the peaks of PLA protons. Based on these results, ethanol quantification in further experiments was carried out using the protons of the $CH_3$ group.

Water identification using the NMR technique led to some modifications in the media for quantification purposes. $^1$H-NMR spectra cannot provide direct evidence of the real amount of water sorbed in the experiments due to the inevitable contamination by environmental water, which would interfere with the actual concentration of water sorbed by the PLA film. If the sample is contaminated with water from the surroundings, it will show up around 1.56 ppm when PLA is dissolved in $CDCl_3$, where the chemical shift changes depending on the solvent used to dissolve the polymer under study.

Another issue is that the peaks of the water overlap with those of the $CH_3$ group of PLA at 1.56 ppm using $CDCl_3$ as the solvent according to FIG. 34. Therefore, to quantify the amount in the sorption experiments, deuterated water ($D_2O$) was used (hydrogen isotopes $^1$H of $H_2O$ have been replaced by the deuterium isotope $^2$H).

Figure 35:
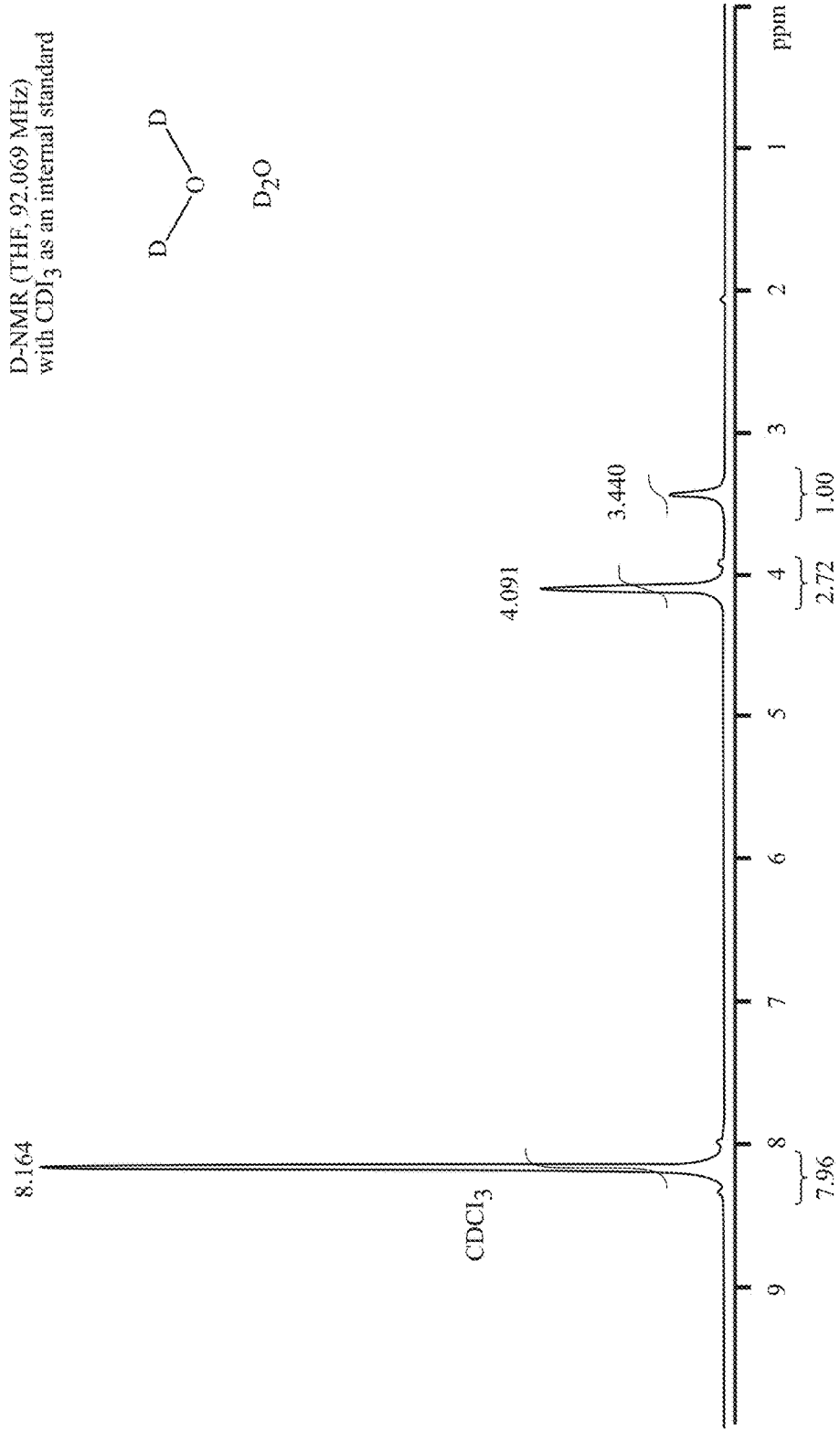
FIG. 35 is a D-NMR spectrum of PLA with $D_2O$ in various experiments.

FIG. 35 shows the D-NMR spectrum of PLA dissolved in THF when 50% ethanol was added. An additional peak in the spectrum at 3.44 ppm was observed. The $D_2O$ peak was tentatively assigned to 4.09 ppm. The reason for the presence of two peaks can be explained by the equilibrium between water and $D_2O$ with a proton transfer from the ethanol to $D_2O$ and an exchange of deuterium between the hydroxyl group of the ethanol and water according to the following reaction:

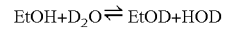

Typically, a single peak for the mixture is exhibited due to rapid exchange between $D_2O$ and ethanol. This is not the case for these measurements because of the low concentration of the $D_2O$/EtOH mixture in the NMR tube, with the lowest concentration detected in sorption experiments of 0.08 μL/mL and 0.24 μL/mL ($8.88 \times 10^{-5}$ and $1.89 \times 10^{-4}$ g/mL) for $D_2O$ and EtOH, respectively. It is worth mentioning that with sorption experiments using 100% $D_2O$, two peaks were seen in the spectrum. In this situation, it could be assumed that there was a proton transfer from the end groups of PLA in the presence of $D_2O$. EXSY NMR (Exchange Spectroscopy) was carried out to verify that both peaks belong to the $D_2O$ in the system. Indeed, cross-peaks were observed between the resonances. Hence, for quantitative purposes, the two peaks were taken into consideration for water sorption in PLA since they represent the water content in the solvent systems under study.

Model for Change in Molecular Weight, Including Polymer Expansion

Let N be the number of polymer chains in the disk at time t and $M_t$ be the number-average molecular weight ($M_n$). In time t+Δt, scission during hydrolytic degradation will cause n cuts in the polymer chains, leaving N−n chains uncut and 2 new chains. Since the total mass before and after scission is the same, the molecular weight at time t+Δt is:

$$M_{t+\Delta t} = M_t \frac{N}{(N-n)+(2n)} \quad \text{(Eq. 5)}$$

If Δt is small, n will be small compared to N. The equation above then reduces to $$M_{t+\Delta t} = M_t \left(1 - \frac{n}{N}\right) \quad \text{(Eq. 6)}$$

so that $$\frac{(M_{t+\Delta t} - M_t)}{M_t} = -\frac{n}{N} = -\frac{\left(\frac{n}{V_d}\right)}{\left(\frac{N}{V_d}\right)} \quad \text{(Eq. 7)}$$

where $V_d$ is the volume of the polymer disk. The quantity $N/V_d$ is related to the initial density of the PLA. The quantity $n/V_d$ is determined by the concentration c of the water in the disk and by the contact time Δt between the PLA and water. Then $$\frac{\Delta M}{M} = -\beta c \Delta t \quad \text{(Eq. 8)}$$

where c is the concentration of water and β is a rate constant. In the limit as Δt approaches zero, $$\frac{dM}{M} = -\beta c\, dt \quad \text{(Eq. 9)}$$

$$M = M_o e^{-\beta \int_0^t c\, dt} \quad \text{(Eq. 10)}$$

where $M_0$ is the initial $M_n$. If c is constant due to fast diffusion, $$M = M_o e^{-\beta ct} \quad \text{(Eq. 11)}$$

If diffusion of water and ethanol into the disk can be considered fast compared to the rate of scission, the mass of water occupying the voids inside the disk is:

$$c = \frac{\text{mass of water}}{V_d} = \frac{(1-p)(V_0 + \Delta V)}{V_d} \quad \text{(Eq. 12)}$$

where p is the volume fraction of water in the ethanol-water mix surrounding the disk, $V_0$ is the total volume of voids initially in the disk, and $\Delta V$ is the increase in this volume due to expansion by ethanol.

If the expansion of the disk found earlier (0.06p) is assumed to apply to only the voids, not the chains, then $$c = (1-p)\left(\frac{V_0}{V_d} + \frac{\Delta V}{V_d}\right) = \quad \text{(Eq. 13)}$$
$$(1-p)\left(\frac{V_0}{V_d} + 0.06p\right) = \left(\frac{V_0}{V_d}\right) + \left(0.06 - \frac{V_0}{V_d}\right)p - 0.06p^2$$

$$M = M_o \exp(-kt) \quad \text{(Eq. 14)}$$

$$k = \beta\left[\frac{V_0}{V_d} + \left(0.06 - \frac{V_0}{V_d}\right)p - 0.06p^2\right] \quad \text{(Eq. 15)}$$

Model for LA Release

From the model for change in molecular weight $$M = M_0 \exp(-kt) \text{ with } k = \beta\left[\frac{V_0}{V_d} + \left(0.06 - \frac{V_0}{V_d}\right)p - 0.06p^2\right],$$

fitting this model to the number molecular weight vs time data for all environments (water, 50% ethanol, 95% ethanol) gave $$B = 1.05 \text{ and } \frac{V_0}{V_d} = 0.0056.$$

With this information, a prediction for the release of LA can be proposed. The mechanism of LA release begins with chain scission inside the disk. This results in chains with very different molecular weights diffusing through the PLA matrix at the same time, crossing the interface some time later into the fluid, and further dissolving into LA monomers, mostly before leaving the PLA matrix. The increment of mass of PLA entering the fluid surrounding the disk in infinitesimal time dt appears to follow the relationship:

$$dm \sim \frac{dt}{M^R} \quad \text{(Eq. 16)}$$

where dm is the infinitesimal mass, M is the molecular weight at time t, which is $M = M_0 \exp(-kt)$, and R is a constant that accounts for all the above effects. When t is small, M is large and dm is small. When t is large, M is small and dm is large.

Since mass leaves the disk by diffusion, dm can be proportional to the disk surface area A. It then enters the surrounding fluid volume $V_f$, and increases the LA concentration. The above relationship therefore becomes:

$$dC_f = \frac{B * A * dt}{V_f * M^R} = \frac{B * A}{V_f * M_o^R} \exp(Rkt)\, dt \quad \text{(Eq. 17)}$$

where $C_f$ is the concentration of PLA in the fluid and B is another constant. Integrating and applying the boundary condition m=0 at t=0:

$$C_f = \frac{Q * A}{V_f}[\exp(Rkt) - 1] \quad \text{(Eq. 18)}$$

where Q is a constant. The $A/V_f$ ratio used in the experiments reported was 1.79 cm²/mL.

Theoretical Diffusion Coefficients of LA-Oligomers

To predict the diffusion coefficients of LA and LA-mers, the free volume model/theory proposed by Ventras and Ventras was applied. The diffusion coefficient ($D_1$) can be determined using the following equation, which depends on temperature, concentration, and the free-volume characteristics of the system:

$$D_1 = \overline{D}_o \exp\left[-\frac{E^*}{RT}\right]\exp\left[-\frac{\omega_1 \hat{V}_1^* + \omega_2 \imath \hat{V}_2^*}{\frac{\hat{V}_{FH}}{Y}}\right] \quad \text{(Eq. 19)}$$

where $\hat{V}_{FH}/y$ is the term where the free-volume characteristics of the system are included, with $\hat{V}_{FH}$ being the average hole free volume per gram of mixture and y the average overlap factor for the mixture introduced, since the same free-volume is available to more than one jumping unit. To calculate the trace diffusion coefficient of LA, the mass fraction of LA in PLA film, $\omega_1$, is assumed to approach 0. Accordingly, the weight fraction of PLA in PLA film, $\omega_2$, is close to 1. $\imath$ is the ratio of critical molar volume of LA jumping unit to critical molar volume of PLA jumping unit, and $\hat{V}_1^*$, and $\hat{V}_2^*$ are the specific hole free volume of LA and PLA required for a jump, respectively. $\hat{V}_{FH}/y$ was calculated using the following equation:

$$\frac{\hat{V}_{FH}}{Y} = \omega_1 \frac{K_{11}}{Y_1}(K_{21} + T - T_{g1}) + \omega_2 \frac{\hat{V}_{FH2}}{Y_2} \quad \text{(Eq. 20)}$$

where $$\frac{K_{11}}{Y_1}$$

and $K_{21}-T_{g1}$ are LA free volume parameters, T is temperature in K, $Y_2$ is the overlap factor for the free volume of pure PLA, and $\hat{V}_{FH2}$ is the specific hole free volume of the equilibrium liquid polymer at any temperature. $\hat{V}_{FH2}$ was calculated depending on the glass transition temperature of PLA ($T_{g2}$):

$$\hat{V}_{FH2}=\hat{V}_2^0(T_{g2})[f_{H2}^G+\alpha_2(T-T_{g2})] \quad T \geq T_{g2} \quad \text{(Eq. 21)}$$

$$\hat{V}_{FH2}=\hat{V}_2^0(T_{g2})[f_{H2}^G+(\alpha_2-\alpha_{c2})(T-T_{g2})] \quad T < T_{g2} \quad \text{(Eq. 22)}$$

where $\hat{V}_2^0(T_{g2})$ is the specific volume of the polymer at $T_{g2}$, $f_{H2}^G$ is the fractional hole free volume of PLA at $T_{g2}$, $\alpha_2$ is the thermal expansion coefficient for the equilibrium liquid polymer, and $\alpha_{c2}$ is the thermal expansion coefficient for the sum of the specific occupied volume and the specific interstitial free volume for the equilibrium liquid polymer. The following equations were used to calculate free volume parameters:

$$f_{H2}^G = \alpha_2 K_{22} \quad \text{(Eq. 23)}$$

$$\alpha_{c2} = \frac{\ln\left[\frac{\hat{V}_2^0(T_{g2})(1-f_{H2}^G)}{\hat{V}_2^0(0)}\right]}{T_{g2}} \quad \text{(Eq. 24)}$$

$$Y_2 = \frac{\hat{V}_2^0(T_{g2})\alpha_2}{K_{12}/Y_2} \quad \text{(Eq. 25)}$$

$$\hat{V}_1^* = \hat{V}_1^0(0) \quad \text{(Eq. 26)}$$

$$\hat{V}_2^* = \hat{V}_2^0(0) \quad \text{(Eq. 27)}$$

$$\frac{K_{12}}{Y_2} = \frac{\hat{V}_2^*}{2.303(C_1^g)_2(C_2^g)_2} \quad \text{(Eq. 28)}$$

$$K_{22} = (C_2^g)_2 \quad \text{(Eq. 29)}$$

where $$\frac{K_{12}}{Y_2}$$

and $K_{22}$ are PLA free volume parameters, $(C_1^g)_2$ and $(C_2^g)_2$ are the Williams-Landel-Ferry (WLF) constants, $\hat{V}_1^0(0)$ and $\hat{V}_2^0(0)$ are the specific volume of equilibrium liquid of LA and PLA at 0 K, respectively. Viscosity-temperature and density-temperature data for pure LA was used to determine $\overline{D}_o$, and $K_{21}-T_{g1}$, using the following equation:

$$\ln n_1 = \ln\left(\frac{0.124 \times 10^{-16}\hat{V}_C^{2/3}RT}{M_1\hat{V}_1^0}\right) - \ln\overline{D}_o + \frac{\hat{V}_1^*}{\left(\frac{K_{11}}{Y_1}\right)(K_{21}+T-T_{g1})} \quad \text{(Eq. 30)}$$

where $n_1$ is viscosity, $\hat{V}_c$ is the LA molar volume at the critical temperature, $M_1$ is the molecular weight of LA and $\hat{V}_1^0$ is the specific volume of the pure LA at T. The diffusion coefficient of oligomers up to five units of LA was predicted using the scaling law:

$$\frac{D(M,T)}{D(M_o,T)} = \left(\frac{M}{M_o}\right)^{-a(T-T_g)} \quad \text{(Eq. 31)}$$

where $M_0$ is the molecular weight of LA, M is the molecular weight of the oligomers, $\alpha$ is a scaling exponent deviation to the Rouse theory, which depends on the geometry of the solute, polymer type and the temperature difference, T and $T_g$.

Initial Amount of Lactic Acid Oligomers

Matrix-assisted laser desorption-ionization time-of-flight mass spectrometry (MALDI-TOF MS; Axima-CFR Plus, Shimadzu Europa, Duisburg, Germany) was used to analyze the presence of lactic acid oligomers in PLA film before hydrolysis through contact with water, 50% and 95% ethanol. a-cyano-4-hydroxycinnamic acid (10 mg/mL in 50/50 acetonitrile/water with 1 mg/mL diammonium hydrogen citrate) and dithranol (10 mg/mL in tetrahydrofuran) were used as MALDI matrix agents. Sample solutions of PLA in THF were prepared at concentrations of 0.1 and 0.01 mg/mL to be analyzed. The negative ion mode was used and the detector m/z range was 200-1500 Da.

The hydrolytic degradation of PLA film at different temperatures was studied using a migration cells as recommended by ASTM D475411. Shortly, the cells comprised disks of PLA film inserted in a stainless-steel wire and separated by glass beads having a total disk surface area fluid volume of 1.79 $cm^2 \cdot mL^{-1}$. Migration cells were stored in a chamber at different temperatures: 40, 60, 70, and 80° C., containing 50% ethanol solution previously conditioned. Experiments at 100° C. were performed using pressure vessels with an internal thread with polytetrafluoroethylene (PTFE) bushings as pressure seals, and the temperature was controlled in an oil bath. Experiments controlling the pH of 50% ethanol solution during the hydrolytic degradation of PLA were performed at 80 and 100° C. with a pH of 11 using a 3-(cyclohecylamino)-1-propanesulfonic acid as a buffer. Samples of film were retrieved periodically to assess number average molecular weight ($M_n$). $M_n$ was assessed as previously described where 10 mg of film were dissolved in tetrahydrofuran (2 mg. $mL^{-1}$) and tested using gel permeation chromatography (GPC) technique. The measurements were conducted in triplicate.

Parameter Estimation: Order of Reaction

To calculate the order of the reaction for the hydrolytic degradation of PLA, the general rate law was used:

$$-\frac{dM_n}{dt} = kM_n^\eta \quad \text{(Eq. 32)}$$

where k is the rate constant of hydrolysis ($h^{-1}$) and $\eta$ is the order of reaction. The parameters k and $\eta$ were estimated separately using the lowest root mean square error (RMSE).

After data analysis and to calculate the hydrolysis rate constant, the first order reaction equation was used:

$$M_n = M_{n_o}\exp(-kt) \quad \text{(Eq. 33)}$$

where $M_{n_o}$ is the initial $M_n$, and t is time.

Parameter Estimation: Activation Energy

Step 1: Re-Parameterization of the Arrhenius Equation

The effect of temperature on the hydrolytic degradation of PLA can be described using the Arrhenius equation:

$$k = k_o\exp\left(-\frac{E_a}{RT}\right) \quad \text{(Eq. 34)}$$

where $k_o(h^{-1})$ is the pre-exponential factor, R is the universal gas constant (8.314 J/mol·K), and T is temperature (K). A reparameterization of the Arrhenius equation is proposed in this study to estimate Ea and to avoid a high correlation between parameters $k_o$ and Ea as previously explained. This can be done by introducing the reference temperature ($T_{ref}$) that corresponds to the rate constant of hydrolysis ($k_{ref}$):

$$k = k_{ref} \exp\left[-\frac{E_a}{R}\left(\frac{1}{T} - \frac{1}{T_{ref}}\right)\right] \quad \text{(Eq. 35)}$$

The hydrolytic degradation of PLA can be described by the change of $M_n$ as a function of time (Eq. (37)). Then, to describe the effect of temperature on the hydrolysis of PLA, the following model is proposed by inserting Eq. (35) in Eq. (33), resulting in:

$$M_n = M_{n_o} \exp\left(-k_{ref} \exp\left[-\frac{E_a}{R}\left(\frac{1}{T} - \frac{1}{T_{ref}}\right)\right]t\right) \quad \text{(Eq. 36)}$$

The hydrolytic degradation can also be pH dependent; therefore, the dependence of pH was introduced in Eq. (36) as an empirical form of secondary model that has been applied similarly for water activity studies:

$$M_n = M_{n_o} \exp\left(-k_{ref} \exp\left[-\frac{E_a}{R}\left(\frac{1}{T} - \frac{1}{T_{ref}}\right) + \beta(\text{pH} - \text{pH}_{ref})\right]t\right) \quad \text{(Eq. 37)}$$

where $\beta$ is a constant which reflects the pH dependence of the hydrolytic degradation and $\text{pH}_{ref}$ is the reference pH.

To estimate $\beta$, experiments involving hydrolysis of PLA at one temperature and different pH's were performed 80° C. at pH 4, 7, and 11. The following equation was used to estimate $\beta$ and $\text{pH}_{ref}$:

$$M_n = M_{n_o} \exp(-k_{ref} \exp[\beta(\text{pH} - \text{pH}_{ref})]t) \quad \text{(Eq. 38)}$$

Step 2: Scaled Sensitivity Coefficient (X')

When parameter estimation is performed, two or more parameters may be involved. Therefore, it is essential to determine if those parameters can be estimated accurately, easily and simultaneously. The sensitivity coefficient (SC) indicates the magnitude of change of the response due to perturbation in parameters, and is an important tool to determine the correlation among parameters. The SC is obtained by taking the first derivative of the dependent variable ($\mu$) with respect to the parameter of interest (i.e. $X_{E_a} = \partial\mu/\partial E_a$). However, for comparing parameters on the same scale, a scaled sensitivity coefficient (SSC) (X') is often plotted. The SSC is provided by multiplying the SC with the parameter itself. For example, the X' of the activation energy can be obtained as follows:

$$X'_{E_a} = E_a \frac{\partial \mu}{\partial E_a} \quad \text{(Eq. 39)}$$

$E_a$ indicates the sensitivity of the rate to temperature. When temperature is constant, it is not possible to estimate $E_a$, or to plot its SSC. Therefore, a new concept was developed to show the temperature-dependent SSC when there are multiple isothermal experiments. So, a ($T_{sim}$) approach was proposed to plot X' of $E_a$ by inserting a linear increasing dynamic temperature function in the model:

$$T_{sim} = T_L + \frac{T_H - T_L}{t_{max}} t \quad \text{(Eq. 40)}$$

where $T_L$ is the lowest temperature (K), $T_H$ is the highest temperature (K), t is time and $t_{max}$ is the maximum time duration.

For the SSC of Eqs. (10) and (11) the same concept as $T_{sim}$ was applied since pH is changing during the hydrolysis reaction. So, a $\text{pH}_{sim}$ approach was proposed by inserting the following function in the models to plot X' when pH is changing over time:

$$P_{sim} = pH_L + \frac{pH_H - pH_L}{t_{max}} t \quad \text{(Eq. 41)}$$

where $\text{pH}_L$ is the lowest pH and $\text{pH}_H$ is the highest pH.

Step 3: Estimation of the Optimum $\text{pH}_{ref}$ and $T_{ref}$

The goal is to obtain near zero correlation among parameters for better estimation since by reducing the correlation, the relative errors will be reduced. To reach the goal it was important to find the optimum $\text{pH}_{ref}$ and $T_{ref}$ as explained in the supporting information provided online.

To estimate Ea in Eq. (37), assuming it is constant over all temperatures and over all pH, it was necessary to estimate $\beta$ from Eq. (38) for later use as a fixed value in Eq. (37). In order to estimate $\beta$, the optimum $\text{pH}_{ref}$ was obtained from Eq. (38) by plotting the correlation between $k_{ref}$ and $\beta$ versus a possible range of $\text{pH}_{ref}$. The optimum $\text{pH}_{ref}$ was used to estimate the parameters $k_{ref}$, $M_{no}$ and $\beta$. Once $\beta$ was estimated, the value was applied as a constant in Eq. (37) and $\text{pH}_{ref}$ used was the optimum $\text{pH}_{ref}$ previously estimated.

The optimum $T_{ref}$ was obtained from a plot of the correlation between $k_{ref}$ and Ea as a function of the possible range of $T_{ref}$ using Eq. (37) and Eq. (36). For the final estimation the optimum $T_{ref}$ value was used to estimate the parameters $k_{ref}$, $M_{no}$ and Ea.

The nonlinear regression (nlinfit) function in MATLAB® 2016a (MathWorks, Natick, Mass., USA) was used to estimate all the parameters. Mean comparisons of the studied parameters among treatments were done using the Tukey HSD test (p<0.05) with JMP® 9.0 (Cary, N.C., USA) statistical software.

Figures 36, 37:
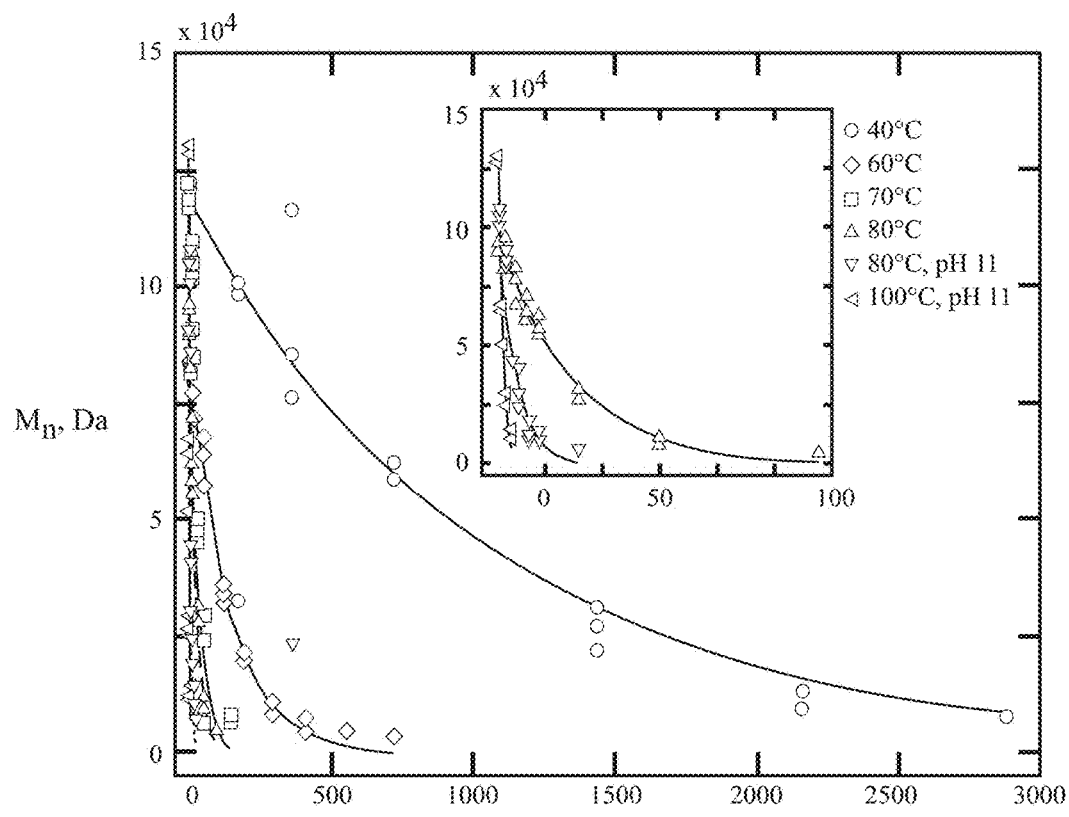
FIG. 36 is a graph illustrating $M_n$ of PLA as a function of time during hydrolytic degradation of PLA film immersed in 50% ethanol at 40, 60, 70, 80, and 100° C. at a pH of 11 in various experiments.
FIG. 37 is a table illustrating the rate constants (k) for PLA films at different temperatures in 50% ethanol solution and the amount of time to reach full hydrolysis of the PLA films to lactic acid at different temperatures in various experiments.

FIG. 36 shows the change on $M_n$ of PLA film as a function of time immersed in 50% ethanol at different temperatures: 40, 60, 70 and 80° C. FIG. 37 presents the rates of hydrolysis, where the hydrolysis rate increased with temperature. Previously, results of hydrolysis at 80° C. controlling the pH 11 was presented making faster the hydrolytic degradation of PLA. At strong basic media, the hydroxide ions catalyze the hydrolysis reactions, in which the molecular weight reduction of PLA is more significant than in acid solutions.

Therefore, the results of increasing the reaction temperature at 100° C., pH 11 to accelerate hydrolysis reaction. FIG. 36 inset shows the faster reduction of $M_n$ at 100° C., pH 11, where PLA film was fragmented by the solvent in around 4 hours. FIG. 37 shows that when the hydrolysis temperature increased from 80 to 100° C. at pH 11, the reaction was around 3.8× faster. Furthermore, FIG. 37 shows the time required to reduce PLA to its monomer lactic acid (LA). The higher the temperature the less time required to hydrolyze PLA to LA maintaining basic conditions. So far, 10 hours would be required to fully hydrolyze PLA to monomeric LA where a much lower time for n-mers of LA would be required. FIG. 38 illustrates the diffusion coefficient (D) and amount of ethanol at equilibrium ($M_\infty$) in PLA films at 40° C. in various embodiments. In addition, FIG. 39 illustrates the boiling point and swelling ration of different ethanol solutions to be used to hydrolyze PLA to LA in various embodiments. FIG. 40 illustrates the parameters to predict the diffusion coefficient of LA and up to 5 LA-mers in PLA in various embodiments.

All combinations of the aforementioned embodiments throughout the entire disclosure are hereby expressly contemplated in one or more non-limiting embodiments even if such a disclosure is not described verbatim in a single paragraph or section above. In other words, an expressly contemplated embodiment may include any one or more elements described above selected and combined from any portion of the disclosure. In various non-limiting embodiments, all values and ranges of values between and including the aforementioned values are hereby expressly contemplated.

One or more of the values described above may vary by ±5%, ±10%, ±15%, ±20%, ±25%, etc. Unexpected results may be obtained from each member of a Markush group independent from all other members. Each member may be relied upon individually and or in combination and provides adequate support for specific embodiments within the scope of the appended claims. The subject matter of all combinations of independent and dependent claims, both singly and multiply dependent, is herein expressly contemplated. The disclosure is illustrative including words of description rather than of limitation. Many modifications and variations of the present disclosure are possible in light of the above teachings, and the disclosure may be practiced otherwise than as specifically described herein.

It is also to be understood that any ranges and subranges relied upon in describing various embodiments of the present disclosure independently and collectively fall within the scope of the appended claims, and are understood to describe and contemplate all ranges including whole and/or fractional values therein, even if such values are not expressly written herein. One of skill in the art readily recognizes that the enumerated ranges and subranges sufficiently describe and enable various embodiments of the present disclosure, and such ranges and subranges may be further delineated into relevant halves, thirds, quarters, fifths, and so on. As just one example, a range "of from 0.1 to 0.9" may be further delineated into a lower third, i.e. from 0.1 to 0.3, a middle third, i.e. from 0.4 to 0.6, and an upper third, i.e. from 0.7 to 0.9, which individually and collectively are within the scope of the appended claims, and may be relied upon individually and/or collectively and provide adequate support for specific embodiments within the scope of the appended claims. In addition, with respect to the language which defines or modifies a range, such as "at least," "greater than," "less than," "no more than," and the like, it is to be understood that such language includes subranges and/or an upper or lower limit. As another example, a range of "at least 10" inherently includes a subrange of from at least 10 to 35, a subrange of from at least 10 to 25, a subrange of from 25 to 35, and so on, and each subrange may be relied upon individually and/or collectively and provides adequate support for specific embodiments within the scope of the appended claims. Finally, an individual number within a disclosed range may be relied upon and provides adequate support for specific embodiments within the scope of the appended claims. For example, a range "of from 1 to 9" includes various individual integers, such as 3, as well as individual numbers including a decimal point (or fraction), such as 4.1, which may be relied upon and provide adequate support for specific embodiments within the scope of the appended claims.

What is claimed is:

1. A method of recycling a polyester, with said method comprising the steps of:
   preparing a solution containing water and an alcohol;
   submerging a poly(lactic acid) in the solution; and
   hydrolytically depolymerizing the poly(lactic acid) while the poly(lactic acid) is submerged in the solution.

2. The method according to claim 1 wherein the step of preparing the solution is further defined as preparing the solution containing from 20 to 70 percent by volume of the alcohol and the balance being the water, based on a total of 100 percent by volume of the solution.

3. The method according to claim 1 wherein the step of preparing the solution is further defined as preparing the solution containing from 40 to 50 percent by volume of the alcohol and the balance being water, based on a total of 100 percent by volume of the solution.

4. The method according to claim 1 wherein the step of preparing the solution is further defined as preparing the solution containing 50 percent by volume of the alcohol and 50 percent by volume of water.

5. The method according to claim 1 wherein the step of preparing a solution is further defined as preparing a solution of water and an alcohol selected from ethanol, methanol, 1-butanol, and 1-propanol.

6. The method according to claim 1 wherein the alcohol is further defined as ethanol and the step of preparing the solution is further defined as preparing the solution containing the ethanol and the water.

7. The method according to claim 6 wherein the step of preparing the solution is further defined as preparing the solution containing from 40 to 50 percent by volume of ethanol and the balance being water, based on a total of 100 percent by volume of the solution.

8. The method according to claim 1 wherein the alcohol is further defined as 1-butanol and the step of preparing the solution is further defined as preparing the solution containing from 20 to 30 percent by volume of 1-butanol and the balance being water, based on a total of 100 percent by volume of the solution.

9. The method according to claim 1 wherein the step of preparing a solution is further defined as preparing a solution of water and an alcohol with the solution having a pH of from 10 to 14.

10. The method according to claim 1 wherein the step of hydrolytically depolymerizing the poly(lactic acid) is further defined as hydrolytically depolymerizing the poly(lactic acid) while submerged in the solution at a temperature of from 40 to 90° C.

11. The method according to claim 1 wherein the water is further defined as heavy water and the step of preparing the solution is further defined as preparing the solution containing the heavy water and the alcohol.

12. The method according to claim 1 wherein the method further comprises the step of forming the poly(lactic acid) into a film having a thickness of from 18 to 38 micrometers.

13. The method according to claim 12 further comprising the step of cutting the film into a plurality of pieces prior to the step of submerging the poly(lactic acid) in the solution.

14. The method according to claim 12 wherein the step of preparing the solution is performed independent of the step of forming the film.

15. The method according to claim 1 wherein the step of submerging the poly(lactic acid) includes submerging the poly(lactic acid) in the solution for a time period of from 6 to 3000 hours.

16. The method according to claim 1 wherein the poly(lactic acid) has at least 100,000 monomer units.

17. The method according to claim 1 wherein the poly(lactic acid) has a number average molecular weight of from $1.21 \times 10^3$ to $1.21 \times 10^6$ Daltons.

18. A method of recycling a polyester, with said method comprising the steps of:
    preparing a solution containing water and an alcohol;
    submerging a polyglycolic acid in the solution; and
    hydrolytically depolymerizing the polyglycolic acid while the polyglycolic acid is submerged in the solution.

* * * * *